US012724097B2

(12) United States Patent
Du et al.

(10) Patent No.: US 12,724,097 B2
(45) Date of Patent: Sep. 1, 2026

(54) SYSTEMS, DEVICES AND METHODS FOR IMAGING CORTICAL AND TRABECULAR BONE

(71) Applicant: The Regents of the University of California, Oakland, CA (US)

(72) Inventors: Jiang Du, San Diego, CA (US); Yajun Ma, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 928 days.

(21) Appl. No.: 17/599,548

(22) PCT Filed: Mar. 30, 2020

(86) PCT No.: PCT/US2020/025817

§ 371 (c)(1),
(2) Date: Sep. 28, 2021

(87) PCT Pub. No.: WO2020/205788

PCT Pub. Date: Oct. 8, 2020

(65) Prior Publication Data

US 2022/0196768 A1 Jun. 23, 2022

Related U.S. Application Data

(60) Provisional application No. 62/826,458, filed on Mar. 29, 2019.

(51) Int. Cl.
*G01R 33/48* (2006.01)
*A61B 5/00* (2006.01)
(Continued)

(52) U.S. Cl.
CPC .......... *G01R 33/4816* (2013.01); *A61B 5/055* (2013.01); *A61B 5/4509* (2013.01);
(Continued)

(58) Field of Classification Search
None
See application file for complete search history.

(56) References Cited

U.S. PATENT DOCUMENTS 8,148,979 B1 * 4/2012 Du .................... G01R 33/5602 324/307
2020/0166596 A1 * 5/2020 Sommer ............. A61B 5/7257

FOREIGN PATENT DOCUMENTS

WO 2012122462 A2 9/2012

OTHER PUBLICATIONS

Water suppression using a combination of hard and soft pulses, J. of Mag. Resonance, 75, 352-357, 1987 (Year: 1987).*

(Continued)

*Primary Examiner* — Michael J Carey
*Assistant Examiner* — Marjan Saboktakin
(74) *Attorney, Agent, or Firm* — Ashurst Perkins Coie US LLP

(57) ABSTRACT

Devices, systems and methods for imaging cortical and trabecular bone are described. An example method for imaging cortical and trabecular bone is provided to include applying one or more adiabatic inversion recovery pulses to a cortical and trabecular bone, wherein the one or more adiabatic inversion recovery pulses are provided with multiple spokes in a three dimensional adiabatic ultrashort TE cones sequence (3D UTE-Cones sequence) that has a TR/TI combination, TR and TI corresponding to repetition time and inversion time, respectively; and performing data acquisition, by using the multiple spokes, on a target signal obtained after the applying of the one or more adiabatic inversion recovery pulses.

14 Claims, 32 Drawing Sheets

(51) Int. Cl.
*A61B 5/055* (2006.01)
*G01R 33/50* (2006.01)
*G01R 33/56* (2006.01)

(52) U.S. Cl.
CPC .......... *A61B 5/4566* (2013.01); *A61B 5/4571* (2013.01); *G01R 33/4826* (2013.01); *G01R 33/50* (2013.01); *G01R 33/5607* (2013.01)

(56) References Cited

OTHER PUBLICATIONS

Short T2 imaging using a 3D double adiabatic inversion recovery prepared ultrashort echo time cones (3D DIR-UTE-Cones) sequence, Mag. Res. Med. 2018 (Year: 2018).*

Carl et al. ("UTE Imaging with simultaneous water and fat signal suppression using a time-efficient multi-spoke inversion recovery pulse sequence" Mag. Res. In Med. 2016) (Year: 2016).*

ISA, International Search Report and Written Opinion for International Application No. PCT/US2020/025817. Mail Date: Sep. 10, 2020. 11 pages.

Ma et al. "Short T2 Imaging Using a 3D Double Adiabatic Inversion Recovery Prepared Ultrashort Echo Time Cones (3D DIR-UTE-Cones) Sequence" Magnetic Resonance in Medicine, 2018, 79, 2555-2563.

Du et al. "Dual inversion recover, ultrashort echo time (DIR UTE) imaging: creating high contrast for short-T2 species" Magnetic Resonance in Medicine, 2010, 63, 447-455.

Abbasi-Rad, S. et al., "Quantification of Human Cortical Bone Bound and Free Water in Vivo with Ultrashort Echo Time MR Imaging: A Model-based Approach," Radiology, vol. 283, No. 3, Jun. 2017, 862-872.

Alem, A. et al., "Increased risk of hip fracture among patients with end-stage renal disease," Kidney International, vol. 58, 2000, 396-399.

Bae, W. C. et al., "Quantitative ultrashort echo time (UTE) MRI of human cortical bone: correlation with porosity and biomechanical properties," Journal of Bone and Mineral Research, vol. 27, No. 4, Apr. 2012, 848-857.

Biswas R. et al., "Ultrashort echo time (UTE) imaging with bi-component analysis: bound and free water evaluation of bovine cortical bone subject to sequential drying," Bone vol. 50, 2012, 749-755.

Boskey A. et al., "Collagen and bone strength," Journal of Bone and Mineral Research, vol. 14, No. 3, 1999, 330-335.

Brandi M., "Microarchitecture, the key to bone quality," Rheumatology, vol. 48, 2009; 3-8.

Burr D., "The contribution of the organic matrix to bone's material properties," Bone, vol. 31, No. 1, Jul. 2002, 8-11.

Cao H, et al., "Quantitative $^{31}$P NMR spectroscopy and 1H MRI measurements of bone mineral and matrix density differentiate metabolic bone diseases in rat models," Bone, vol. 46, 2010, 1582-1590.

Cao H, et al., "Quantitative bone matrix density measurement by water- and fat-suppressed proton projection MRI (WASPI) with polymer calibration phantoms," Magn Reson Med, vol. 60, 2008, 1433- 1443.

Carl, M. et al., "UTE Imaging with Simultaneous Water and Fat Signal Suppression Using a Time-Efficient Multispoke Inversion Recovery Pulse Sequence," Magn. Reson. Med., vol. 76, 2016, 577-582.

Chang, E.Y. et al., "Effects of Achilles tendon immersion in saline and perfluorochemicals on T2 and T2*," J. Magn. Reson. Imaging, vol. 40, 2014, 496-500.

Chang, E.Y. et al., "Ultrashort echo time magnetization transfer (UTE-MT) imaging of cortical bone," NMR Biomed., vol. 28, 2015, 873-880.

Chang, E.Y., et al., "UTE imaging in the musculoskeletal system," J. Magn. Reson. Imaging, vol. 41, 2015, 870-883.

Chen, J. et al., "Evaluation of bound and pore water in cortical bone using ultrashort-TE MRI," NMR Biomed., 28 (2015) 1754-1762.

Chen, J. et al., "Measurement of bound and pore water $T_1$ relaxation times in cortical bone using three-dimensional ultrashort echo time cones sequences," Magn. Reson. Med., 77 (2016) 2136-2145.

Cowin, C., "Bone poroelasticity," J Biomechanics, vol. 32, 1999, 217-238.

Cummings S., et al., "Risk factors for hip fracture in white women," Study of osteoporotic fractures research group, The New England Journal of Medicine, vol. 332, No. 12, 1995, 767-773.

De Lact C, et al., "Bone density and the risk of hip fracture in men and women: cross sectional analysis," Br Med J, vol. 315, 1997, 221-225.

Du, J. et al., "Assessment of cortical bone with clinical and ultrashort echo time sequences," Magn. Reson. Med., vol. 70, 2013, 697-704.

Du, J. et al., "Orientational analysis of the Achilles tendon and enthesis using an ultrashort echo time spectroscopic imaging sequence," Magn. Reson. Imaging. 28 (2010) 178-184.

Du, J. et al., "Qualitative and quantitative ultrashort echo time (UTE) imaging of cortical bone," J Magn Reson 2010; 207:304-311.

Du, J. et al., "Qualitative and quantitative ultrashort-TE MRI of cortical bone," NMR Biomed. 26 (2013) 489-506.

Du, J. et al., "Two dimensional ultrashort echo time imaging using a spiral trajectory," Magn. Reson. Imaging 2008; 26:304-312.

Du, J. et al., "Ultrashort echo time imaging with bicomponent analysis," Magn Reson Med 2012; 67:645-649.

Du, J. et al., "Ultrashort TE imaging with off-resonance saturation contrast (UTE-OSC)," Magn. Reson. Med 2009; 62: 527-531.

Du, J. et al., "Ultrashort TE spectroscopic imaging (UTESI) of cortical bone," Magn. Reson. Med. 2007; 5:1001-1009.

Elliott SR, et al., "The water content of bone. I. The mass of water, inorganic crystals, organic matrix, and CO2 space components in a unit vol. of the dog bone," J Bone Joint Surg Am 1957; 39(A):167-188.

Faulkner K., "Bone matters: are density increases necessary to reduce fracture risk?," J Bone Miner Res 2000; 15:183-187.

Gee, C.S. et al., "Validation of bone marrow fat quantification in the presence of trabecular bone using Mri," J. Magn. Reson. Imaging. 42 (2015) 539-44.

Granke, M. et al., "Identifying Novel Clinical Surrogates to Assess Human Bone Fracture Toughness," J. Bone Miner. Res. 30 (2015) 1290-1300.

Gurney, P. et al., "Design and analysis of a practical 3D cones trajectory," Magn. Reson. Med. 55 (2006) 575-582.

Horch R., et al., "Clinically-compatible MRI strategies for discriminating bound and pore water in cortical bone," Magn Reson Med 2012; 68:1774-1784.

Horch R. et al., "Characterization of $^{1}$H NMR signal in human cortical bone for magnetization resonance imaging," Magn Reson Med 2010; 64:680-687.

Horch, R. et al., "Non-invasive predictors of human cortical bone mechanical properties: $T_2$-Discriminated 1H NMR compared with high resolution X-ray," PLoS One. 6 (2011) 1-5.

Jang, H. et al., "Fat Suppression for Ultrashort Echo Time Imaging Using a Single Point Dixon Method," NMR in Biomedicine, vol. 32, 2019, 1-9.

Jerban, S. et al., "Collagen proton fraction from ultrashort echo time magnetization transfer (UTE-MT) MRI modelling correlates significantly with cortical bone porosity measured with micro-computed tomography (uCT)," NMR Biomed. 32 (2019) 1-10.

Jerban, S. et al., "Detecting stress injury (fatigue fracture) in fibular cortical bone using quantitative ultrashort echo time-magnetization transfer (UTE-MT): An ex vivo study," NMR Biomed. 31 (2018) 1-11.

Larson P. et al., "Using adiabatic inversion pulses for long-T2 suppression in ultrashort echo time (UTE) imaging," Magn Reson Med 2007; 58:952-961.

Law, M. R. et al., "Regular review: strategies for prevention of osteoporosis and hip fracture," BMJ 1991; 303:453-459.

Lees S., "A mixed pacing model for bone collagen," Calcif Tissue Int 1981; 33:591-602.

(56) References Cited

OTHER PUBLICATIONS

Li, C. et al., "Cortical Bone Water Concentration: Dependence of MR Imaging Measures on Age and Pore Volume Fraction," Radiology, 272 (2014) 796-806.
Lu, X. et al., "Three Dimensional Ultrashort Echo Time Imaging with Tri-component Analysis for Human Cortical Bone," Magn. Reson. Med., vol. 82, 2019, 348-355.
Ma, Y. et al., "Accurate $T_1$ mapping of short $T_2$ tissues using a three-dimensional ultrashort echo time cones actual flip angle imaging-variable repetition time (3D UTE-Cones AFI-VTR) method," Magn. Reson. Med., vol. 80, (2018) 598-608.
Ma, Y. et al., "Quantitative magnetization transfer ultrashort echo time imaging using a time-efficient 3D multispoke cones sequence," Magn. Reson. Med., vol. 79, (2018) 692-700.
Ma, Y. et al., "Quantitative two-dimensional ultrashort echo time magnetization transfer (2D UTE-MT) imaging of cortical bone," Magn. Reson. Med., vol. 79, 2018, 1941-1949.
Ma, Y. et al., "Ultrashort echo time magnetization transfer (UTE-MT) imaging and modeling: magic angle independent biomarkers of tissue properties," NMR Biomed. 29 (2016) 1546-1552.
Manhard, M. et al., "30-Second bound and pore water concentration mapping of cortical bone using 2D UTE with optimized half-pulses," Magn. Reson. Med. 77 (2017) 945-950.
Manhard, M. et al., "In Vivo Quantitative MR Imaging of Bound and Pore Water in cortical bone," Radiology, vol. 277, No. 1, (2015) 221-230.
Manhard, M. et al., "MRI-derived bound and pore water concentrations as predictors of fracture resistance," Bone, 87 (2016) 1-10.
Martin, R. B. et al., "The relative effects of collagen fiber orientation, porosity, density, and mineralization on bone strength," J Biomech 1989; 22:419-426.
Miller PD, et al., Clinical utility of bone mass measurements in adults: consensus of an international panel. Semin Arthritis Rheum 1996; 25:361-372.
Morris, M. et al., "Fluid spaces in canine bone and marrow," Microvascular Research, 1982; 23(2): 188-200.
Mueller K. et al., "Bone density and composition: age-related and pathological changes in water and mineral content," J Bone Joint Surg Am 1966; 48:140-148.
Neuman W. F. et al., "The chemical dynamics of bone mineral," Chicago: Univ of Chicago Press 1958, 220 pages.
Ni, Q. et al., "Assessment of water distribution changes in human cortical bone by nuclear magnetic resonance," Meas Sci Technol 2007; 18:715-723.
Nickolas T. L. et al., "Relationship between moderate to severe kidney disease and hip fracture in the United States," J Am Soc Nephrol 2006; 17:3223-3232.
Nyman J.s. et al., "Measurements of mobile and bound water by nuclear magnetic resonance correlate with mechanical properties of bone," Bone, 2008; 42(1): 193-199.
Nyman J. et al., "The influence of water removal on the strength and toughness of cortical bone," J Biochem, 2006; 39(5): 931-938.
Rad, H. S. et al., "Quantifying cortical bone water in vivo by three-dimensional ultra-short echo-time MRI," Nmr Biomed. 24 (2011) 855-864.
Rajapakse, C. et al., "Volumetric Cortical Bone Porosity Assessment with MR Imaging: Validation and Clinical Feasibility," Radiology, vol. 276, No. 2, (2015) 526-535.
Reichert, I.L.H. et al., "Magnetic resonance imaging of cortical bone with ultrashort TE pulse sequences," Magn. Reson. Imaging, 23 (2005) 611-618.
Riggs B. et al., "The prevention and treatment of osteoporosis," N Engl J Med 1992; 327:620-627.
Ritchie R. et al., "Plasticity and toughness in bone," Phys Today 2009; 62:41-47.
Robinson R. et al., "The water content of bone," J Bone Joint Surg 1957; 39:167-188.
Robson M. et al., "Magnetic resonance: an introduction to ultrashort TE (UTE) imaging," J Comput Assist Tomogr 2003; 27:825-846.
Schneider E. L., et al. The aging of America. Impact on health care costs. JAMA 1990; 263:2335-2340.
Schuit S.C.E. et al., "Fracture incidence and association with bone mineral density in elderly men and women: the Rotterdam study," Bone 2004; 34:195-202.
Seeman E. et al., "Bone quality: the material and structural basis of bone strength," J Bone Miner Metab (2008) 26:1-8.
Seifert, A. et al., "Solid-State Quantitative $^1H$ and $^{31}P$ MRI of Cortical Bone in Humans," Curr. Osteoporos. Rep. (2016) 14:77-86.
Snyder S. et al., "Estimation of mechanical properties of cortical bone by computed tomography," J Orthop Res 1991; 9:422-431.
Springer, F. et al., "Magnetization transfer contrast imaging in bovine and human cortical bone applying an ultrashort echo time sequence at 3 Tesla," Magn Reson Med. 61 (2009) 1040-1048.
Techawiboonwong A. et al., "Cortial bone water: in vivo quantification with ultrashort echo-time MR imaging," Radiology, vol. 248, No. 3, 2008, 824-833.
Techawiboonwong A. et al. "In vivo MRI of submillisecond $T_2$ species with two-dimensional and three-dimensional radial sequences and applications to the measurement of cortical bone water," NMR Biomed 2008; 21:59-70.
Timmins, P. et al., "Bone water," Calcif Tissue Res 1977; 23:1-5.
Trajanoskka K. et al., "Fracture incidence and secular trends between 1989 and 2013 in a population based cohort: The Rotterdam Study," Bone 2018; 114:116-124.
Turner C., "Bone strength: current concepts," Ann NY Acad Sci 2006; 1068:429-446.
Viquet-Carrin S. et al., "The role of collagen in bone strength," Osteoporosis Int 2006; 17:319-336.
Wan, L. et al., "Fast quantitative three-dimensional ultrashort echo time (UTE) magnetic resonance imaging of cortical bone using extended cones sampling," Magn. Reson. Med., vol. 82, No. 1, Jul. 2019, 225-236.
Wang, X. et al., "Age-related changes in the collagen network and toughness of bone," Bone, vol. 31, No. 1, Jul. 2022, 1-7.
Wang X. et al., "Determination of cortical bone porosity and pore size distribution using a low field pulsed NMR approach," Journal of Orthopaedic Research 2003; 21:312-319.
Wehrli F. et al., "Quantitative MRI for the assessment of bone structure and function," NMR Biomed 2006; 19:731-764.
Wehrli F. et al., "Nuclear magnetic resonance studies of bone water," Ann Biomed Eng, vol. 33, No. 1, Jan. 2005, 79-86.
Winner S. J. et al., "Perimenopausal risk of falling and incidence of distal forearm fracture," Br Med J 1989; 298:1486-1488.
World Health Organization, "Assessment of fracture risk and its application to screening for postmenopausal osteoporosis," WHO Technical Report Series 843. Geneva: WHO 1994, 136 pages.
Wu Y. et al. "Bone matrix imaged in vivo by water- and fat-suppressed proton projection MRI (WASPI) of animal and human subjects," J Magn Reson Imaging 2010; 31:954-963.
Wu Y. et al., "Density of organic matrix of native mineralized bone measured by water- and fat-suppressed proton projection MRI," Magn Reson Med 2003; 50:59-68.
Zhao, X. et al., "Feasibility of assessing bone matrix and mineral properties in vivo by combined solid-state $^1H$ and $^{31P}$ MRI," PLoS One, 12 (2017) 1-16.
Zioupos P. et al., "The role of collagen in the declining mechanical properties of aging human cortical bone," J Biomed Mater Res 1999; 45:108-116.

* cited by examiner

SYSTEMS, DEVICES AND METHODS FOR IMAGING CORTICAL AND TRABECULAR BONE

CROSS REFERENCE TO RELATED APPLICATIONS

This patent document is a U.S.C. § 371 National Stage application of International Application No. PCT/US2020/025817 entitled "SYSTEMS, DEVICES AND METHODS FOR IMAGING CORTICAL AND TRABECULAR BONE" filed on Mar. 30, 2020 which claims priority to and benefits of U.S. provisional Patent Application No. 62/826,458, entitled "SYSTEMS, DEVICES AND METHODS FOR IMAGING CORTICAL AND TRABECULAR BONE," filed on Mar. 29, 2019. The entire contents of the above patent applications are incorporated by reference as part of the disclosure of this patent document.

TECHNICAL FIELD

This patent document relates to systems, devices, and processes for imaging cortical and trabecular bone.

BACKGROUND

The cortical and trabecular bone is both functionally and biomechanically important for human. Evaluation of cortical and trabecular bone provides important information about risk of both osteoporosis and bone fracture. Areal bone mineral density (BMD) of trabecular bone in the spine and/or hip is the most commonly used clinical diagnostic test for assessing skeletal status and fracture risk. More recently computed tomography (CT) and dual energy X-ray absorptiometry (DEXA) have provided quantitative analysis through measurement of volumetric BMD.

Osteoporosis (OP) is a disease characterized by low bone mass and microarchitectural deterioration of bone tissue which lead to increased bone fragility and an increase in fracture risk. There are more than 40 million people with OP or low bone mass in the United States alone. This results in more than 1.5 million fractures with an annual cost estimated at about $17 billion. The number of fractures is projected to double, or triple over the next 30-50 years. The need for focused preventive strategies has become a major public health priority.

Routine clinical evaluation of OP has been limited to the assessment of bone mineral density (BMD) using dual energy X-ray absorptiometry (DEXA). DEXA can only assess bone mineral. Bone is a composite material consisting of, by volume, mineral (~43%), organic matrix (~35%) and water (~22%). Bone mineral provides stiffness and strength. Collagen provides ductility and the ability to absorb energy before fracturing. Water contributes to viscoelasticity and poroelasticity. Bone includes all of these components in a complex hierarchical structure. Both material composition and physical structure contribute to the unique strength of bone. The contribution of mineral to bone's mechanical properties has dominated scientific thinking, however, accurate evaluation of bone quality requires information about all of its major constituents. Because of the limitations (only bone mineral being assessed), DEXA is only moderately successful at identifying patients who subsequently experience fractures and is of limited value in accounting for changes in fracture risk that result from treatment.

SUMMARY

Disclosed are devices, systems and methods for imaging cortical and trabecular bone.

In one aspect, a method for imaging cortical and trabecular bone is provided. The method comprises: applying one or more adiabatic inversion recovery pulses to the cortical and trabecular bone, wherein the one or more adiabatic inversion recovery pulses are provided with multiple spokes in a three dimensional adiabatic ultrashort TE cones sequence (3D UTE-Cones sequence) that has a TR/TI combination, TR and TI corresponding to repetition time and inversion time, respectively; and performing data acquisition, by using the multiple spokes, on a target signal obtained after the applying of the one or more adiabatic inversion recovery pulses.

In some implementations, the applying the one or more adiabatic inversion recovery pulses causes an unwanted signal from a tissue in the cortical and trabecular bone to be suppressed, the tissue having a relatively longer transverse relaxation time than that of the cortical and trabecular bone. In some implementations, the TR/TI combination is preselected to sufficiently suppress the unwanted signal from the tissue in the cortical and trabecular bone. In some implementations, the one or more adiabatic inversion recovery pulses include at least one of a single adiabatic inversion recovery pulse or a double adiabatic inversion recovery pulse. In some implementations, the tissue corresponds to at least one of marrow fat or muscle. In some implementations, the method further comprises, after the applying of the one or more adiabatic inversion recovery pulses, applying a soft-hard composite pulse to the cortical and trabecular bone to further suppress the unwanted signal from the tissue in the cortical and trabecular bone. In some implementations, the soft-hard composite pulse includes a soft pulse centered on fat on-resonance frequency with a negative flip angle to flip and a hard pulse with a positive flip angle. In some implementations, the method further comprises: exciting the target signal by applying a short rectangular pulse having a duration less than 100 μs. In some implementations, the multiple spokes are obtained after each of the one or more adiabatic inversion recovery pulse.

In another aspect, a method for imaging cortical and trabecular bone is provided to comprise: rotating a magnetization of a tissue in the cortical and trabecular bone in a first direction by applying a first pulse with a negative angle to the cortical and trabecular bone; further rotating the magnetization of the tissue in the cortical and trabecular bone in a second, opposite direction to the first direction by applying a second pulse with a positive angle to the cortical and trabecular bone; and obtaining an image of the cortical and trabecular bone by performing data acquisition within a time interval after the second pulse is applied.

In some implementations, the negative flip angle and the positive flip angle have a same absolute value. In some implementations, the first pulse is configured to be centered on on-resonance frequency of the tissue to flip the magnetization of the tissue. In some implementations, the second pulse has a duration shorter than that of the first pulse. In some implementations, the tissue corresponds to fat tissue. In some implementations, a magnetization of water content in the cortical and trabecular bone is rotated by applying the second pulse.

In another aspect, a system for imaging cortical and trabecular bone is provided. The system comprises: a pulse application device structured to include a channel operable to apply, to the cortical and trabecular bone, one or more adiabatic inversion recovery pulses; a data acquisition device interfaced with the pulse application device and operable to obtain image data associated with the cortical and trabecular bone and perform data acquisition on the obtained image data; and a data processing and control device in communication with the data acquisition device, the data processing and control device including a processor configured to process the image data obtained by the data acquisition device to provide, based on the processed image data, mapping information of one or more properties associated with the cortical and trabecular bone.

In some implementations, the data processing and control device is configured to provide the mapping information on at least one of total water, bound water, pore water, or collagen proton. In some implementations, the one or more adiabatic inversion recovery pulses include at least one of a single adiabatic inversion recovery pulse or a double adiabatic inversion recovery pulse. In some implementations, the pulse application device is further configured to further apply a soft-hard composite pulse to the cortical and trabecular bone, the soft-hard composite pulse including a soft pulse centered on fat on-resonance frequency with a negative flip angle and a hard pulse with a positive flip angle. In some implementations, the channel of the pulse application device is configured to apply the one or more adiabatic inversion recovery pulses toward the cortical and trabecular bone in a hip or a spine. In some implementations, the data acquisition device is configured to perform data acquisition using multiple spokes. In some implementations, the one or more adiabatic inversion recovery pulses and the multiple spokes are provided during a three-dimensional adiabatic ultrashort TE cones sequence (3D UTE-Cones sequence) that has a TR/TI combination to sufficiently suppress an unwanted signal from a tissue in the cortical and trabecular bone, TR and TI corresponding to repetition time and inversion time, respectively. In some implementations, the one or more adiabatic inversion recovery pulses are configured to suppress an unwanted signal from a tissue in the cortical and trabecular bone, the tissue having a relatively longer transverse relaxation time than that of the cortical and trabecular bone.

DETAILED DESCRIPTION

Figures 1A, 1B, 1C, 1D, 1E, 1F, 1G:
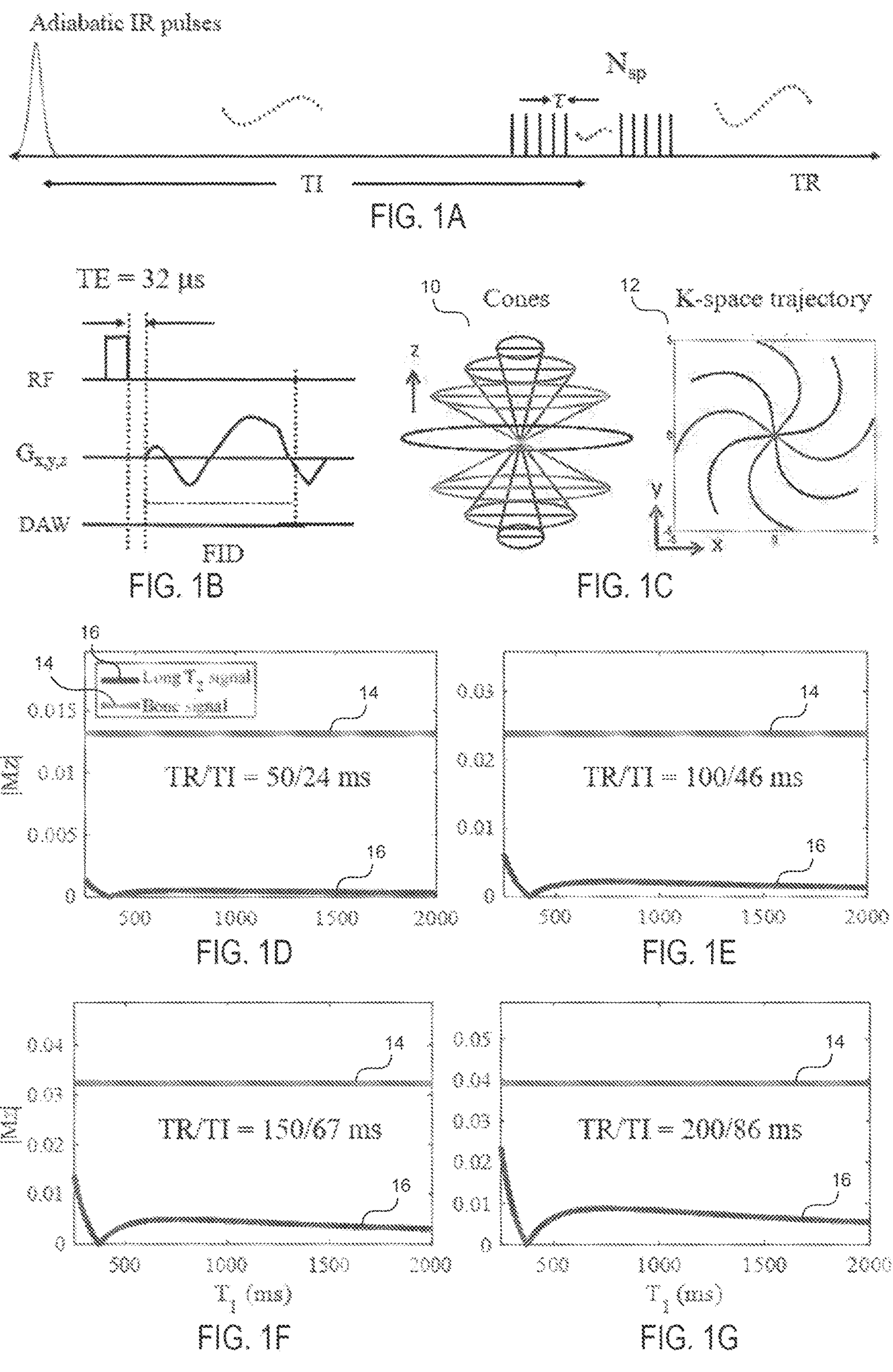
FIGS. 1A to 1C show examples of pulses employed in a 3D SIR-UTE sequence used for cortical and trabecular bone imaging in accordance with some implementations of the disclosed technology.
FIGS. 1D to 1G show examples of simulation results of cortical and trabecular bone imaging using the 3D SIR-UTE sequence in accordance with some implementations of the disclosed technology.

Disclosed are devices, systems and methods for providing 3D high contrast imaging of cortical and trabecular bone.

Some implementations of the disclosed technology provide a 3D adiabatic inversion recovery prepared UTE Cones (3D IR-UTE) sequence for high contrast direct imaging of cortical and trabecular bone with full suppression of surrounding long T2 tissues including the bone marrow and muscle on a clinical scanning device. Some implementations of the disclosed technology develop and evaluate a 3D IR-UTE sequence for volumetric imaging of cortical and trabecular bone ex vivo and in vivo on a clinical scanning device in clinically acceptable scan times.

Trabecular bone is highly responsive to metabolic stimuli and has a turnover rate about eight times higher than that of cortical bone, making it a prime target for detecting bone loss in early osteoporosis (OP). Areal bone mineral density (BMD) of trabecular bone in the spine and/or hip using dual energy X-ray absorptiometry (DEXA) is the most commonly used clinical diagnostic test for assessing skeletal status and fracture risk. However, a number of clinical studies have demonstrated the limitations of BMD measurements. It has been recognized that BMD can only account for about 60% of bone strength.

For the last two decades, quantitative magnetic resonance imaging (MM) has been used to assess the properties of trabecular bone, including $T_2$* or $T_2$' of bone marrow and high resolution imaging of bone microstructure, which are helpful in predicting osteoporotic fracture risk. Quantification of $T_2$* or $T_2$' takes advantage of the fact that local field is perturbed due to the difference in susceptibility between trabecular bone and marrow, which is affected by the density and structure of trabecular bone. High resolution imaging can directly visualize dark trabecular bone due to its low water content and short $T_2$ relaxation. With image postprocessing, it is possible to obtain 3D architecture and corresponding structural parameters of the trabecular bone, which are highly related to the bone strength.

The implementations of the disclosed technology can be utilized to provide imaging of cortical and trabecular bone at various sites such as the spine, femoral head and neck, shoulder, wrist, ankle, tibial midshaft, femoral midshaft, etc. In some implementations, the 3D high contrast imaging of cortical and trabecular bone can be provided using three-dimensional single adiabatic inversion recovery prepared Ultrashort Echo Time (3D SIR-UTE) and double adiabatic inversion recovery prepared UTE (3D DIR-UTE) techniques. A soft-hard composite pulse can also be used for water excitation with fat signals greatly suppressed, when compared with a regular short hard pulse used for non-selective excitation in UTE imaging of bone. The combination of the soft-hard composite pulse with 3D SIR-UTE and DIR-UTE techniques can further improve the robustness of cortical and trabecular bone imaging. Moreover, various implementation of the disclosed technology can quantify longitudinal relaxation time (T1) and apparent transverse relaxation time (T2*) to evaluate cortical and trabecular bone quality, and bound water content to evaluate bone quantify, as bound water content can be used as a biomarker of organic matrix density. For cortical bone, it is possible to measure total water, bound water, pore water and collagen backbone proton density.

In the below, various implementations of the disclosed technology will be discussed with reference to drawings. Section headings are used in the present document only to facilitate ease of understanding and scope of the embodiments and techniques described in each section are not only limited to that section.

3D Adiabatic Inversion Recovery Prepared UTE Cones

In some implementations of the disclosed technology, the longitudinal magnetizations of marrow fat and pore water are inverted and suppressed through either a single adiabatic inversion recovery (SIR) pulse or a double adiabatic inversion recovery (DIR) preparation pulse. The 3D IR-UTE sequence can be used for high contrast direct imaging of trabecular bone with excellent suppression of long T2 tissues. This technique is likely to provide more information on bone quality and risk of bone fracture and osteoporosis. In some implementations, water bound to the organic matrix of bone has extremely short apparent transfer relaxation time T2* (of the order of ~0.3 ms). Its longitudinal magnetization cannot be inverted by the relatively long single or double adiabatic inversion pulses (pulse duration much longer than bound water T2*), leading to nearly full saturation of bound water signal. Meanwhile, the longitudinal magnetizations of long T2 marrow fat and pore water can be uniformly inverted and nulled by the SIR or DIR preparation pulses, when an appropriate time to inversion (TI) is chosen. Bound water has short T2*, as well as short T1. Its longitudinal magnetization recoveries quickly during TI and can be selectively detected by the 3D UTE data acquisition.

As a result, the 3D SIR-UTE and DIR-UTE techniques can be used for volumetric imaging of bound water in both cortical and trabecular bone, which will be further discussed later in this specification. Furthermore, some implementations of the disclosed technology propose a soft-hard composite pulse for water excitation, which is expected to minimize fat signal while not saturate bone water signal due to the use of the off-resonance soft pulse with a very small flip angle (e.g., 2°). The soft-hard composite pulse may be used together with the 3D SIR-UTE and DIR-UTE sequences for further suppression of residual fat signal, providing more robust imaging of bound water in cortical and trabecular bone. Some implementations of the disclosed technology can quantify bound water T2* by repeating 3D SIR-UTE/DIR-UTE acquisitions with a series of echo times (TEs). Some implementations of the disclosed technology can quantify bound water T1 by repeating 3D SIR-UTE/DIR-UTE acquisitions with a series of TR/TI combinations. Some implementations of the disclosed technology can quantify bound water content by comparing bone signal with that of a reference phantom with known proton density (e.g., a rubber band which has similar T1 and T2* relaxation times as bound water in bone). The combination of a soft-hard composite pulse with the 3D SIR-UTE and DIR-UTE acquisitions may further improve the quantification of T1, T2* and bound water concentrations in cortical and trabecular bone, as well as total water, bound water, pore water and collagen backbone proton density for cortical bone.

The 3D SIR-UTE and DIR-UTE techniques, especially together with a soft-hard composite pulse, provide volumetric assessment of cortical and trabecular bone relaxation times (T1, T2*) and bound water content. Marrow fat and pore water signals are suppressed through single or double adiabatic inversion recovery preparation pulses. Therefore, the 3D SIR-UTE and DIR-UTE techniques are likely significantly better or an important supplemental technique when compared with the current gold standard, DEXA, which is based on 2D x-ray projection data without any 3D structural information. DEXA cannot provide any information about bone quality. Therefore, the 3D SIR-UTE and DIR-UTE assessment of cortical and trabecular bone relaxation times (T1 and T2*) and bound water concentration (a biomarker of organic matrix density), as well as total water, bound water, pore water and collagen backbone proton density for cortical bone, are technically novel, and can provide unique information about bone quantity and quality.

Some implementations of the disclosed technology provide 3D high contrast imaging of cortical and trabecular bone (cortical and trabecular bone at various sites such as the spine, femoral head and neck, shoulder, wrist, ankle, tibial midshaft, femoral midshaft, etc.) using three-dimensional single adiabatic inversion recovery prepared Ultrashort Echo Time (3D SIR-UTE) and double adiabatic inversion recovery prepared UTE (3D DIR-UTE) techniques. A soft-hard composite pulse can also be used for water excitation with fat signals greatly suppressed, when compared with a regular short hard pulse used for non-selective excitation in UTE imaging of bone. The combination of the soft-hard composite pulse with 3D SIR-UTE and DIR-UTE techniques may further improve the robustness of cortical and trabecular bone imaging. Moreover, we can quantify longitudinal relaxation time (T1) and apparent transverse relaxation time (T2*) to evaluate cortical and trabecular bone quality, and bound water content to evaluate bone quantify, as bound water content can be used as a biomarker of organic matrix density. For cortical bone, we can measure total water, bound water, pore water and collagen backbone proton density.

In this technique, the longitudinal magnetizations of marrow fat and pore water are inverted and suppressed through either a single adiabatic inversion recovery (SIR) pulse or a double adiabatic inversion recovery (DIR) preparation pulse. Water bound to the organic matrix of bone has extremely short apparent transfer relaxation time T2* (of the order of ~0.3 ms). Its longitudinal magnetization cannot be inverted by the relatively long single or double adiabatic inversion pulses (pulse duration much longer than bound water T2*), leading to nearly full saturation of bound water signal. Meanwhile, the longitudinal magnetizations of long T2 marrow fat and pore water can be uniformly inverted and nulled by the SIR or DIR preparation pulses, when an appropriate time to inversion (TI) is chosen. Bound water has short T2*, as well as short T1. Its longitudinal magnetization recoveries quickly during TI, and can be selectively detected by the 3D UTE data acquisition. As a result, the 3D SIR-UTE and DIR-UTE techniques can be used for volumetric imaging of bound water in both cortical and trabecular bone.

In some implementations, a soft-hard composite pulse for water excitation is proposed, which is expected to minimize fat signal while not saturate bone water signal due to the use of the off-resonance soft pulse with a very small flip angle (e.g., 2°). The soft-hard composite pulse may be used together with the 3D SIR-UTE and DIR-UTE sequences for further suppression of residual fat signal, providing more robust imaging of bound water in cortical and trabecular bone. In some implementations, bound water T2* by repeating 3D SIR-UTE/DIR-UTE acquisitions with a series of echo times (TEs) can be quantified. Bound water T1 can be quantified by repeating 3D SIR-UTE/DIR-UTE acquisitions with a series of TR/TI combinations. Bound water content can be quantified by comparing bone signal with that of a reference phantom with known proton density (e.g., a rubber band which has similar T1 and T2* relaxation times as bound water in bone). The combination of a soft-hard composite pulse with the 3D SIR-UTE and DIR-UTE acquisitions may further improve the quantification of T1, T2* and bound water concentrations in cortical and trabecular bone, as well as total water, bound water, pore water and collagen backbone proton density for cortical bone.

Osteoporosis (OP) is a disease characterized by low bone mass and microarchitectural deterioration of bone tissue which lead to increased bone fragility and an increase in fracture risk. There are more than 40 million people with OP or low bone mass in the United States alone. This results in more than 1.5 million fractures with an annual cost estimated at about $17 billion. The number of fractures is projected to double, or triple over the next 30-50 years. The need for focused preventive strategies has become a major public health priority.

Routine clinical evaluation of OP has been limited to the assessment of bone mineral density (BMD) using dual energy X-ray absorptiometry (DEXA). DEXA can only assess bone mineral. Bone is a composite material consisting of, by volume, mineral (~43%), organic matrix (~35%) and water (~22%). Bone mineral provides stiffness and strength. Collagen provides ductility and the ability to absorb energy before fracturing. Water contributes to viscoelasticity and poroelasticity. Bone includes all of these components in a complex hierarchical structure. Both material composition and physical structure contribute to the unique strength of bone. The contribution of mineral to bone's mechanical properties has dominated scientific thinking, however, accurate evaluation of bone quality requires information about all of its major constituents. Because of the limitations (only bone mineral being assessed), DEXA (dual energy X-ray absorptiometry), which is the existing art and will be further discussed in the below, is only moderately successful at identifying patients who subsequently experience fractures and is of limited value in accounting for changes in fracture risk that result from treatment.

A DEXA scan is a non-invasive test that measures bone mineral density (BMD) to assess if a person is at risk of osteoporosis or fracture. DEXA stands for dual energy x-ray absorptiometry—a mouthful of a term that actually tells a lot about this procedure, in which two X-ray beams are aimed at the bones. DEXA is today's established standard for measuring bone mineral density (BMD). A DEXA scan detects weak or brittle bones to help predict the odds of a future fracture and, sometimes, to determine if someone should be taking medication (such as a bisphosphonate) to slow bone loss. After an initial DEXA scan, subsequent scans can be done to compare the progression of bone loss, for example, comparing a baseline scan with a second scan can show if bone density is improving, worsening, or staying the same. A DEXA scan also can be used to assess how well osteoporosis treatment is working. And after a fracture, a DEXA scan can assess if the break was likely due to osteoporosis.

The results of a bone density measurement (DEXA scan) are reported in two ways: as T-scores and as Z-scores. A T-score compares your bone density to the optimal peak bone density for your gender. It is reported as the number of standard deviations below the average, which is based on the bone density of a healthy 30-year-old adult.

A T-score of greater than −1 is considered normal.

A T-score of −1 to −2.5 is considered osteopenia and indicates a risk of developing osteoporosis.

A T-score of less than −2.5 is diagnostic of osteoporosis.

A Z-score is used to compare your results to others of your same age, weight, ethnicity, and gender. This is useful to determine if there is something unusual contributing to your bone loss. A Z-score over 2.0 is considered normal for the person's age, while one below 2.0 is regarded as below the expected range for the person's age. Specifically, a Z-score of less than −1.5 raises a concern that factors other than aging are contributing to osteoporosis. These factors may include thyroid abnormalities, malnutrition, medication interactions, tobacco use, and others.

As mentioned above, DEXA is the diagnostic gold standard used in clinical practice, measuring bone mineral density or BMD. However, the majority of bone, including the organic matrix and water, which together occupy ~60% of bone by volume, are inaccessible using x-ray based techniques. These components make important contributions to the mechanical properties of bone, partially explaining why DEXA is only moderately successful at identifying patients who subsequently experience fractures, and is of limited value in accounting for changes in fracture risk that result from treatment. BMD by itself only predicts fractures with an accuracy of 30-50%. The overall fracture risk increases 13-fold from ages 60 to 80, but BMD alone only predicts a doubling of the fracture risk. A recent study of over 7806 patients found that only 44% of all non-vertebral fractures occurred in women with a T-score below −2.5 (WHO definition of OP). This percentage dropped to 21% in men. Another study of over 14,613 participants found that ~80% of all non-vertebral fractures occurred among individuals with a T-score below −2.5. There is a clear need for more sensitive risk assessment tools, which include information such as bone microstructure, organic matrix and water.

The 3D SIR-UTE and DIR-UTE techniques, especially together with a soft-hard composite pulse, provide volumetric assessment of cortical and trabecular bone relaxation times (T1, T2*) and bound water content. Marrow fat and pore water signals are suppressed through single or double adiabatic inversion recovery preparation pulses. Therefore, the 3D SIR-UTE and DIR-UTE techniques are likely significantly better or an important supplemental technique when compared with the current gold standard, DEXA, which is based on 2D x-ray projection data without any 3D structural information. DEXA cannot provide any information about bone quality. The 3D SIR-UTE and DIR-UTE assessment of cortical and trabecular bone relaxation times (T1 and T2*) and bound water concentration (a biomarker of organic matrix density), as well as total water, bound water, pore water and collagen backbone proton density for cortical bone, are technically novel, and may provide unique information about bone quantity and quality. The 3D SIR-UTE and DIR-UTE techniques, especially together with a soft-hard composite pulse, can be an important tool for more accurate assessment of cortical and trabecular bone quantity and quality than the current gold standard, DEXA.

Ultrashort Echo Time (UTE) sequences have been proposed to image short T2 tissues such as cortical bone, calcified cartilage, menisci, ligaments and tendons. Since marrow fat is abundant in trabecular bone, direct imaging of trabecular bone requires efficient suppression of signals from marrow fat. Adiabatic inversion pulses provide uniform inversion of long T2 tissues such as marrow fat and muscle, while saturating ultrashort T2 tissues such as cortical and trabecular bone which can be subsequently detected with UTE acquisitions. Meanwhile, marrow fat in trabecular bone is subject to strong susceptibility and has a broad range of resonance frequencies. For more robust suppression of marrow fat, some implementations employ an adiabatic inversion pulse with a relatively broad spectral bandwidth (i.e. 1.6 kHz) to robustly invert and null the longitudinal magnetizations of marrow fat, followed by highly time-efficient 3D UTE Cones sampling.

The example of the simulation using the suggested bone imaging is discussed with reference to FIGS. 1A to 1G. FIG. 1A shows the 3D SIR-UTE sequences that uses an adiabatic inversion pulses for long T2 suppression, followed by 3D UTE-Cones data acquisition. A series of spokes ($N_{sp}$) can be acquired after each IR pulse to improve the acquisition efficiency. In FIG. 1B, for each spoke, a short rectangular pulse is used for non-selective signal excitation followed by 3D spiral sampling with a nominal TE of 32μ. In the simulation, the time between the excitation and acquisition is reduced and thus a very short pulse is used to excite the signal. An implementation uses a very short pulse to excite the signal, then the acquisition quickly starts. The echo time here is shown in FIG. 1B. Shortly after the short rectangular pulse excitation, then the acquisition with 3D spiral acquisition is performed, which is called cones trajectory. In FIG. 1C, the spiral trajectories are arranged with conical view ordering 10. The k-space trajectory 12 is also shown. More efficient long T2 (i.e. marrow fat and muscle) suppression can be achieved with a shorter TR. In the example, Bloch simulation was performed for four different TRs (i.e. 50, 100, 150 and 200 ms) with corresponding best TIs to evaluate the effectiveness of long T2 suppression. The optimal TI was determined with nulling T1 set from 350-400 ms. The T1 of trabecular bone was set to 150 ms and water proton density was set to 10% in simulation.

Trabecular bone imaging using the 3D SIR-UTE sequence is simulated with different TRs. In FIGS. 1D to 1G, the simulation results of signal suppression for the long T2 tissues with a broad range of T1s (e.g., from 250 to 2000 ms) using the IR sequence are illustrated. The results demonstrate that a shorter TR leads to better long T2 suppression. Even with a relatively long TR of 200 ms it still shows that bone signal is at least four times higher than that of long T2 tissues. While the bone signal 14 and the long $T_2$ signal 16 are indicated, a shorter TR demonstrates more robust long T2 suppression and better bone contrast.

Pore water resides in the macroscopic pores of bone. Pore water relaxation is complicated due to the surface relaxation mechanism. Pore water near the surface of pores may have fast relaxation, while pore water away from the surface may have much slower relaxation. As a result, pore water may have a broad range of T1 relaxation times. It will be difficult to completely invert and null pore water magnetizations with a broad range of T1s using a single adiabatic inversion recovery pulse. Furthermore, the majority of the signal in trabecular bone imaging is from marrow fat, and muscle surrounding the tissue (e.g., hip and spine imaging). T1s for muscle and fat are very different, and they are very different from T1s of pore water. A double adiabatic inversion recovery preparation pulse, or DIR pulse, is proposed for more robust imaging of bound water in both cortical and trabecular bone. In DIR, two identical adiabatic inversion pulses with the same center frequency are used to invert the longitudinal magnetizations of long $T_2$ tissues. With specific inversion times, tissues with a broad range of $T_1$s, such as fat and muscle, can be well suppressed or nulled simultaneously. It is also insensitive to $B_1$ inhomogeneity because of the adiabatic properties, and $B_0$ inhomogeneity because of the relatively wide inversion pulse bandwidth. Furthermore, multi-spoke acquisition per DIR preparation can be incorporated, allowing for time-efficient volumetric imaging and T2* quantification of short $T_2$ tissues ex vivo and in vivo on a clinical 3T scanner.

Figures 2A, 2B, 2C:
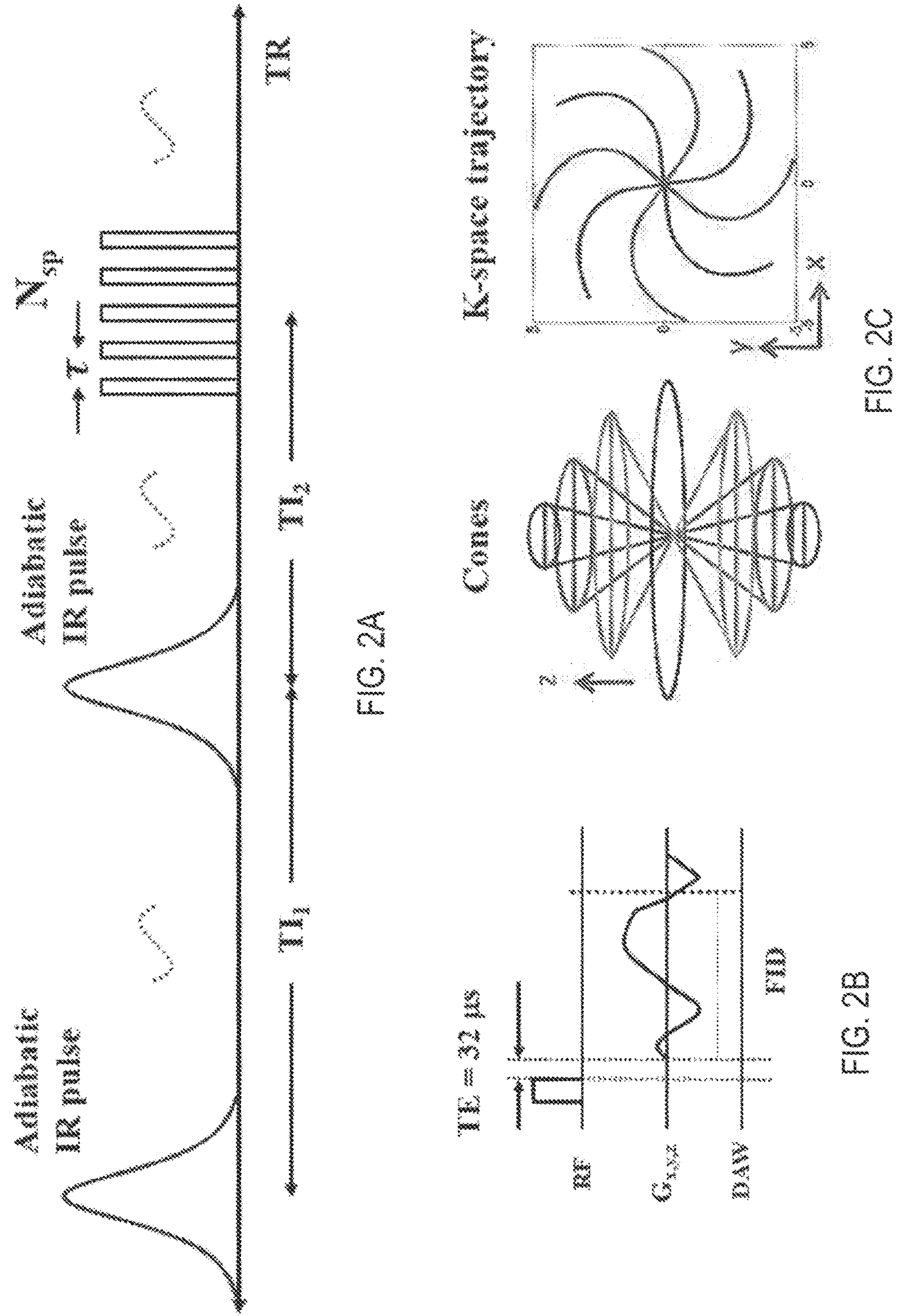
FIGS. 2A to 2C show examples of pulses employed in a 3D DIR-UTE sequence used for cortical and trabecular bone imaging in accordance with some implementations of the disclosed technology.

FIGS. 2A to 2C show another example of the 3D DIR-UTE pulse used for cortical and trabecular bone imaging. In FIG. 2A, the two adiabatic inversion pulses (duration of ~6 ms) with specific inversion recovery times of $TI_1$ and $TI_2$ are repeated every TR period. The double adiabatic inversion recovery pulses are implemented to cover broad bandwidth.

The broad bandwidth DIR pulse allows more robust suppression of long T2 tissues or tissue components due to the broad range of T1s.

To speed up data acquisition, multiple spokes can be sampled after each long $T_2$ preparation. Following the two adiabatic inversion pulses are $N_{sp}$ separate k-space spokes or acquisitions with an equal time interval i for fast data acquisition. $T1_1$ is defined as the time between the centers of the two adiabatic inversion pulses. $TI_2$ is defined as the time from the center of the second adiabatic inversion pulse to the center spoke of the multispoke acquisition. The relatively long T2 suppression time can be secured. In FIG. 2B, a short rectangular pulse (duration of 26 to 52 μs) is used for non-selective signal excitation, followed by 3D spiral trajectories with conical view ordering as shown in FIG. 2C. FIG. 2C shows the cones 22 and K-space trajectory 24. Adiabatic inversion pulses can effectively invert the longitudinal magnetizations of long $T_2$ tissues such as muscle and fat. They are also relatively immune to spatial $B_1$ inhomogeneity because of the adiabatic properties (21). However, the longitudinal magnetizations of short T2 tissues (T2* in the range of 0.1 to 2 ms) are typically not inverted but saturated by the relatively long adiabatic inversion pulses.

Numerical simulation was performed to investigate the efficiency of the DIR preparation scheme in simultaneous suppression of signals from tissues with a range of $T_1$s (200 to 2000 ms). The $T_1$ values of fat, muscle and bone are assumed to be 340, 1400 and 250 ms, respectively, and the proton density of bone is assumed to be 10 times less than fat and muscle. TR, α, τ and $N_{sp}$ were 200 ms, 20°, 5 ms and 5, respectively. Optimal $TI_1$ and $TI_2$ could be determined based on the T1s. The signal suppression efficiency of the DIR preparation scheme against $T_1$ was investigated.

Figure 3A:
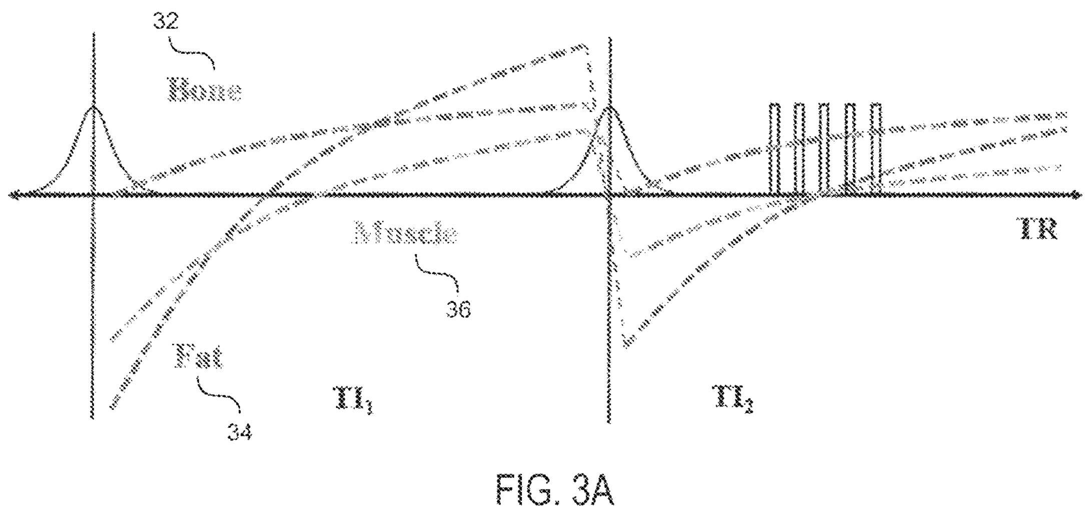
FIGS. 3A and 3B show examples of DIR-UTE simulation results of cortical and trabecular bone imaging in accordance with some implementations of the disclosed technology.
Figure 3B:
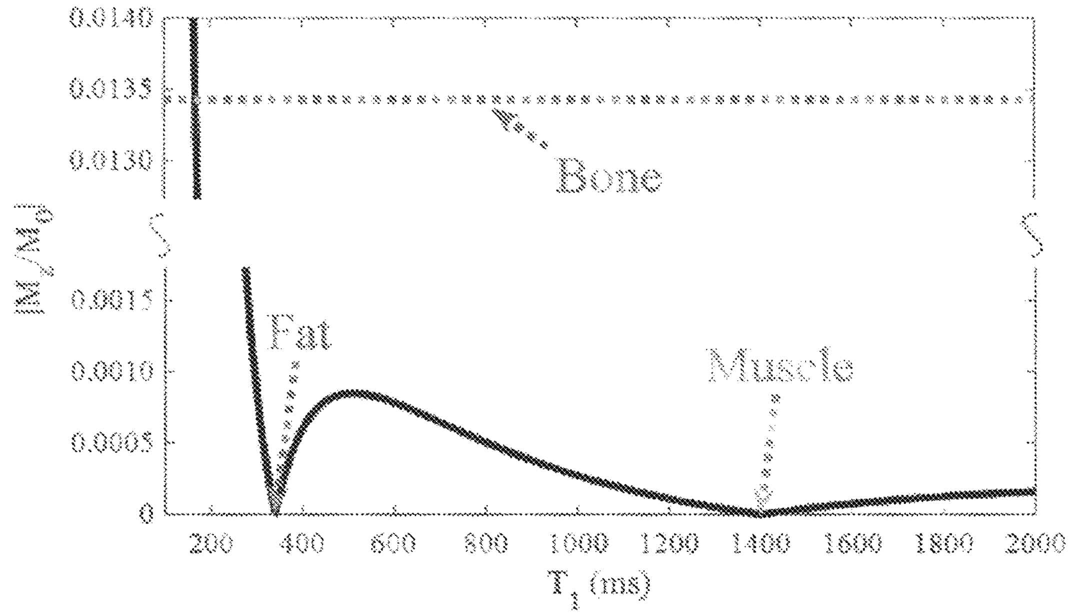

FIGS. 3A and 3B show example of pulses and simulation results of cortical and trabecular bone imaging in accordance with some implementations of the disclosed technology. In FIG. 3A, with DIR preparation, two adiabatic inversion pulses are applied sequentially using two different inversion times of $TI_1$ and $TI_2$ to invert and null the longitudinal magnetizations of long $T_2$ muscle and fat, followed by multispoke 3D UTE-Cones data acquisition. In FIG. 3A, the magnetizations of bone, fat, muscle are indicated as 32, 34, and 36. In the example of simulation, $TI_1$ and $TI_2$ were 99.7 and 45.1 ms, respectively, for optimal fat and muscle suppression with a TR of 200 ms. The simulation results in FIG. 3B shows high contrast imaging of bone with excellent suppression of tissues with a broad range of T1s including muscle and fat. As can be seen from FIG. 3B, both fat and muscle signals are nulled. Tissues with $T_1$s below or above $T_1$ of bone are also well suppressed, suggesting that the DIR preparation scheme can provide efficient long $T_2$ suppression with reduced $T_1$ dependency. The bone signal curve is also plotted together with fat and muscle for comparison. It is necessary to mention that the x-axis is only applied to fat and muscle, but not to bone whose signal is purely determined by $TI_2$.

Soft-Hard Composite Pulse

Figures 4A, 4B:
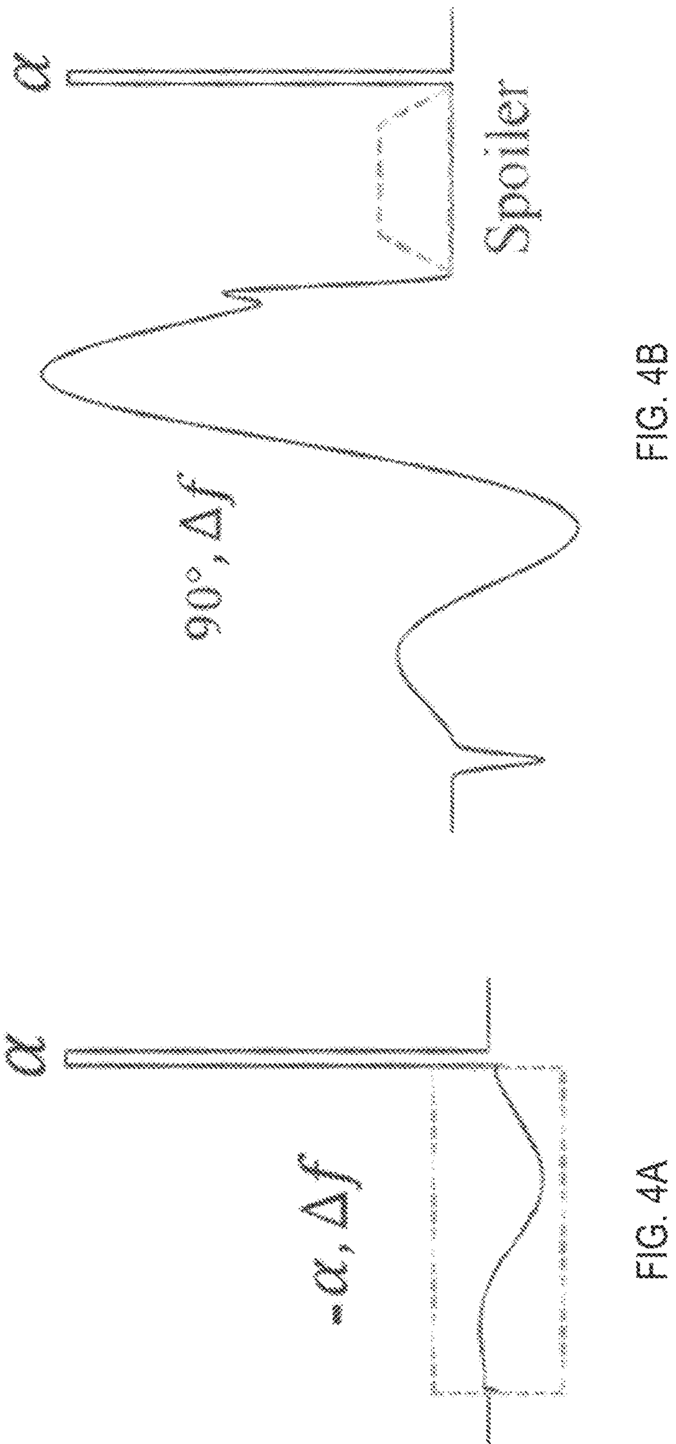
FIG. 4A shows an example of a soft-hard composite pulse in accordance with some implementations of the disclosed technology and FIG. 4B shows a conventional FatSat module.

An example of a newly designed soft-hard composite pulse and the conventional FatSat module are shown in FIGS. 4A and 4B, respectively. FIG. 4A shows an example of a new fat suppression RF pulse for UTE imaging of short T2 tissues, including cortical and trabecular bone, with well-preserved short T2 signals using a soft-hard composite pulse. The proposed fat suppression pulse or water excitation pulse consists of two RF pulses: one soft pulse and one hard pulse. The soft pulse centers on fat on-resonance frequency (Δf) with a negative flip angle (−α). The soft pulse is used to flip the fat magnetization only, then followed by a short hard pulse with a same flip angle as the soft pulse, which flips both water and fat magnetizations in the opposite direction. Since the fat magnetization experiences both tipping down and tipping back with an identical flip angle, most of the fat magnetization returns to the equilibrium state. Subsequently, most of the fat signals are not received by the following UTE acquisitions. In addition, the soft pulse has been designed with a narrow bandwidth of several hundred Hz and with pulse duration of several milliseconds; thus, the RF power of the soft pulse is relatively low. The soft pulse excitation is therefore expected to have little saturation effect on the water magnetizations. This makes it possible for the water signals to be effectively excited by the following hard pulse. FIG. 4B shows the commonly used FatSat module for comparison. The conventional FatSat technique consists of a saturation pulse centered on the fat peak with a flip angle no less than 90°, followed by a gradient spoiler to crush all the excited transversal magnetizations. Then, a short hard pulse is employed for signal excitation. Typically, the flip angle of the soft pulse (the same as the excitation flip angle) in the soft-hard composite pulse is typically much lower than 90° for UTE imaging. Therefore, both direct and indirect saturations (i.e. MT effect) of the water signals produced by the soft pulse in the proposed soft-hard composite pulse are much less than the water saturations induced by the FatSat module.

To evaluate both the fat suppression and the water saturation for the proposed soft-hard composite pulse and the conventional FatSat module, a signal suppression ratio (SSR, unit in percentage) was used, defined as the division of the subtracted image between non-fat suppression image and fat suppression image by the non-fat suppression image. A higher SSR value corresponded to better fat suppression or a stronger water saturation induced by the used fat suppression technique. Both the pixel-wised SSR maps and region of interest (ROI)-based signal mean and standard deviation values within all the tissues were used for comparison.

Figure 5:
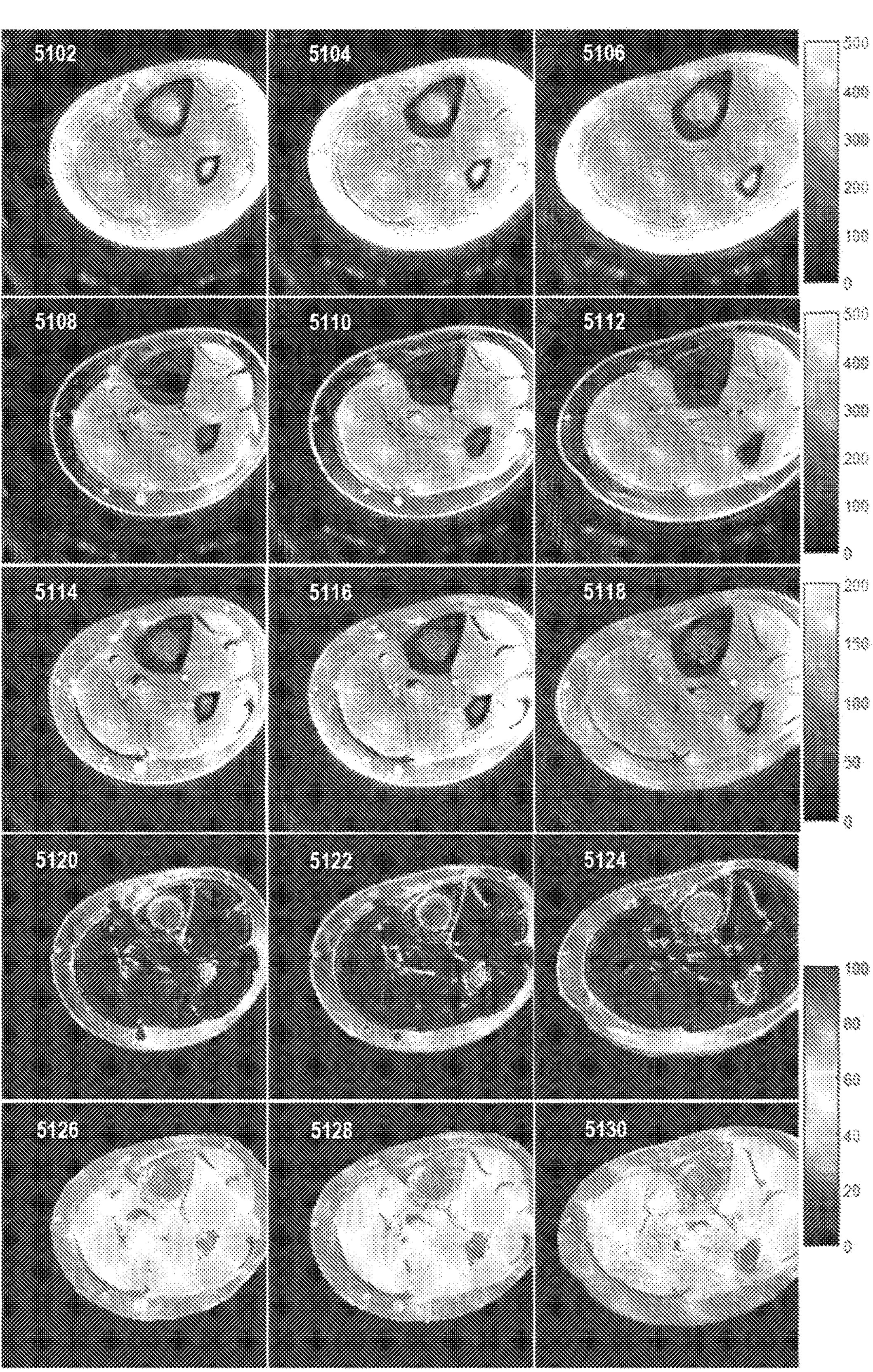
FIG. 5 shows In vivo tibia UTE-Cones imaging results when using excitations with different pulses.

FIG. 5 shows In vivo tibia UTE-Cones imaging results (from a 35-year-old volunteer) using excitations from different pulses. Images 5102 to 5106 are obtained using excitations with a single hard pulse, images 5108 to 5112 are obtained using excitations with the proposed soft-hard water excitation pulse, and the images 5114 to 5118 are obtained using excitations with the conventional FatSat module. Fat was well suppressed by both the proposed soft-hard pulse and the FatSat module. The cortical bone (see the arrows in 5108, 5110, 5112) was much better preserved in the soft-hard excitation images (see 5108 to 5112) compared with FatSat images (see 5114 to 5118). Both fat suppression and water saturation levels can be observed in the SSR images. The images 5120 to 5124 are obtained using excitations with the soft-hard pulse and the images 5126 to 5130 are obtained using FatSat module.

The UTE-Cones images with the proposed soft-hard composite pulse excitation show excellent image contrast and well-preserved cortical bone and muscle signals. In comparison, most of the short T2 signals (i.e. cortical bone and coil elements) were lost in the FatSat UTE-Cones images due to the strong saturation effect of the FatSat module. SSR was 7.7±7.6 for tibia midshaft using the soft-hard composite pulse, which was about ten times lower than the SSR of 68.7±5.5 for tibial midshaft using the conventional FatSat module. The soft-hard composite is highly efficient in water excitation with much reduced fat excitation.

Figures 6A, 6B, 6C, 6D:
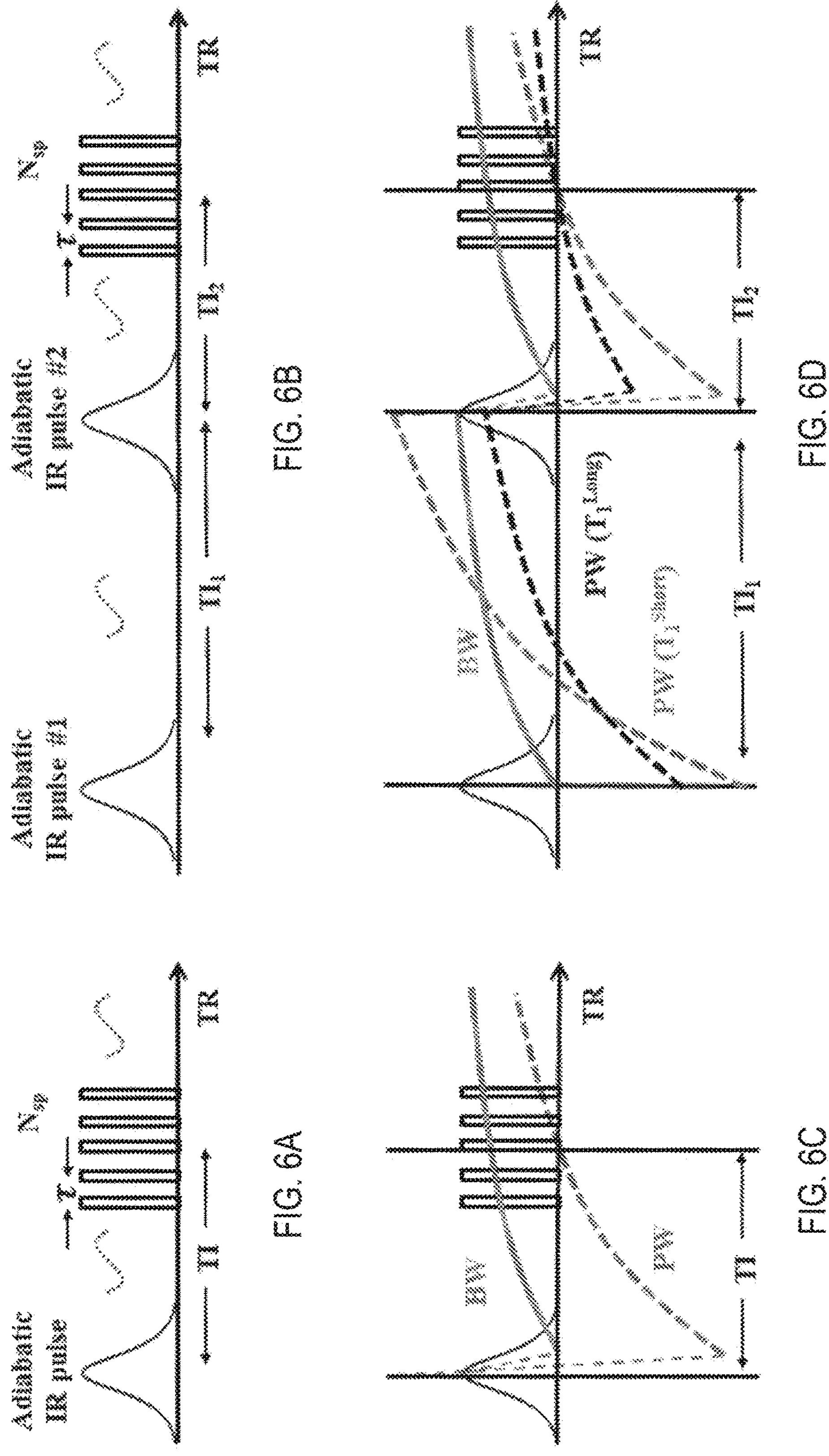
FIGS. 6A to 6D show examples of pulses and signals of cortical and trabecular bone imaging in accordance with some implementations of the disclosed technology.

FIGS. 6A to 6D show examples of pulses and signals of cortical and trabecular bone imaging in accordance with some implementations of the disclosed technology. The 3D UTE-Cones sequence can be combined with a single adiabatic inversion recovery pulse as shown in FIG. 6A. The single adiabatic inversion recovery pulse is used for IR-UTE imaging of bound water (BW), where pore water (PW) is assumed to have a single $T_1$ and can be inverted and nulled with an appropriate TI as shown in FIG. 6C. In some implementations, the UTE sequence can also be combined with a double adiabatic inversion recovery pulse shown in FIG. 6B. The double adiabatic inversion recovery pulse is sued for DIR-UTE imaging of bound water, where pore water is assumed to have a range of $T_1$s and can all be inverted and nulled with an appropriate combination of $TI_1$ and $TI_2$ as shown in FIG. 6D.

Bound water concentration (pBw) can be measured by comparing the 3D IR-UTE or DIR-UTE signal of cortical and trabecular bone with that of a rubber phantom. In IR-UTE, bone signal can be described by Eq. [1], where Q is the inversion efficiency of the adiabatic IR pulse. For bound water with a T2* of ~0.3 ms, Q approximates to zero according to Bloch equation simulation. Since $T_1$ and $T_2$* values are similar for bound water and rubber, WCBw can be simplified as in Eq. [2]. For more accurate suppression of pore water which may have a broad range of $T_1$s due to surface relaxation (i.e., shorter $T_1$ for water near the pore surface, longer $T_1$ for water away from the pore surface), the DIR-UTE sequence is expected to provide more accurate estimation of bound water content using an equation similar to Eq. [2].

$$I_{bone}^{IR-UTE} \propto \frac{\left[1-(1-Q)\times e^{-TI/T_1^{BW}}-Q\times e^{-TR/T_1^{BW}}\right]}{1-Q\times\cos(\theta)\times e^{-TR/T_1^{BW}}}\times\sin(\theta)\times e^{-TE/T_2^*} \quad [1]$$

$$\rho_{BW} \approx \frac{I_{bone}^{IR-UTE}}{I_{rubber}^{IR-UTE}}\times\eta\times\rho_{rubber}^{25} \quad [2]$$

Ex vivo imaging was performed for hip, patellar and shoulder bone samples. Quantitative 3D SIR-UTE was employed for bound water T2* measurement for the hip bone sample (TE=0.032, 0.2, 0.4, 0.8, 1.1, 3.3 and 4.4 ms, TR/TI=82/38 ms). Dual-echo SIR-UTE sequence was used for shoulder bone imaging with TE=0.032/2.2 ms and TR/TI=88/40 ms. The small patellar sample was imaged with a high-resolution SIR-UTE sequence (voxel size=156×156×300 $\mu m^3$, TR/TI=133/58 ms) using a 30 mL birdcage coil. The signal intensity of the patellar sample was also compared with the corresponding μCT (18×18×18 $\mu m^3$) images. Then in vivo spine and hip bone imaging was performed in a coronal scan on four volunteers (26 to 46 years old) following IRB approval with written, informed consent. The sequence parameters of SIR-UTE sequence are shown as follows: FOV=45×45×20.8 $cm^3$, Matrix=180×180×52, TR/TI=183/78 ms, flip angle=25°, $N_{sp}$=5, spoke interval τ=6 ms, sampling BW=166 kHz, IR pulse bandwidth=1.64 kHz, scan time=10 min.

Figure 7A:
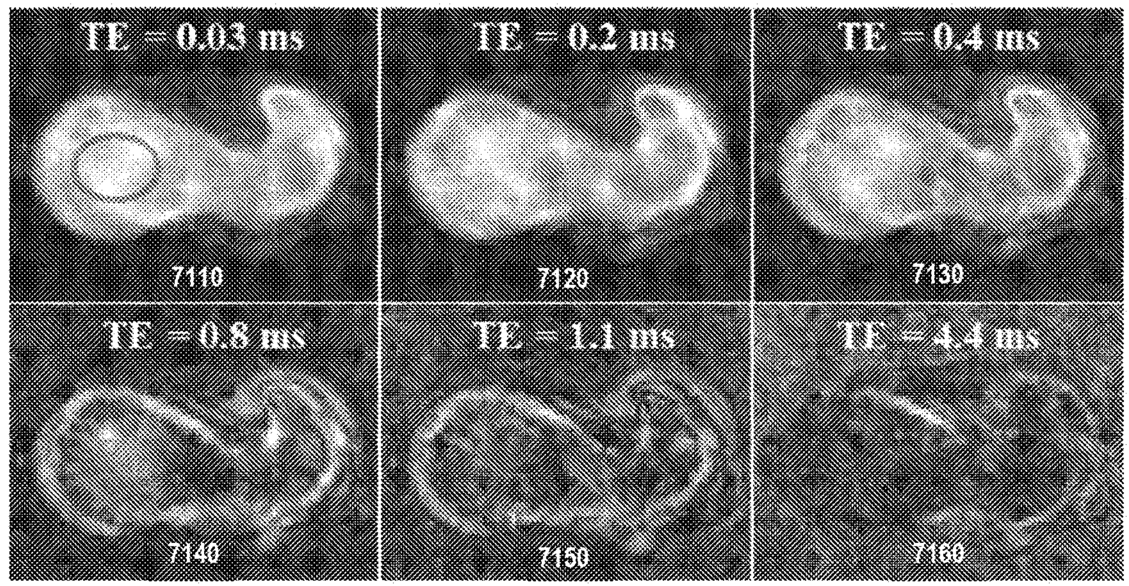
FIG. 7A shows femur sample images with different echo times and FIG. 7B shows a graph of trabecular bone signal.
Figure 7B:
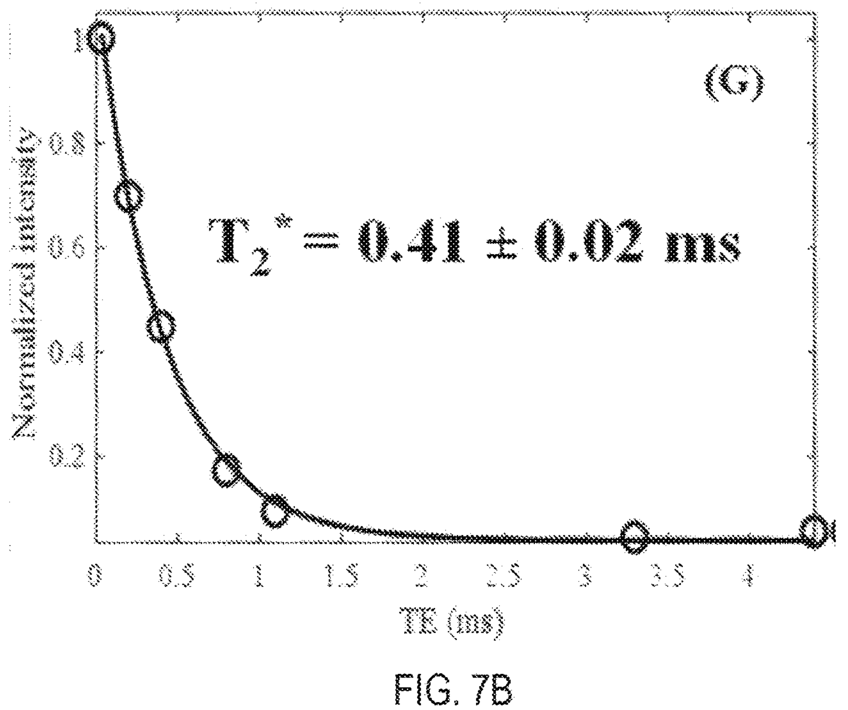

FIG. 7A shows selective SIR-UTE images 7110, 7120, 7130, 7140, 7150, 7160 of a cadaveric human femur sample using the 3D SIR-UTE sequence with different echo time and FIG. 7B shows a graph showing trabecular bone signal. Trabecular bone signals decayed very quickly with longer echo times as shown in FIGS. 7A and 7B. Almost no signal was observed in the image with a TE of 4.4 ms, demonstrating excellent suppression of signals from bone marrow. Excellent T2* fitting was obtained for the trabecular bone with an ultrashort T2* of 0.41±0.02 ms.

Figure 8:
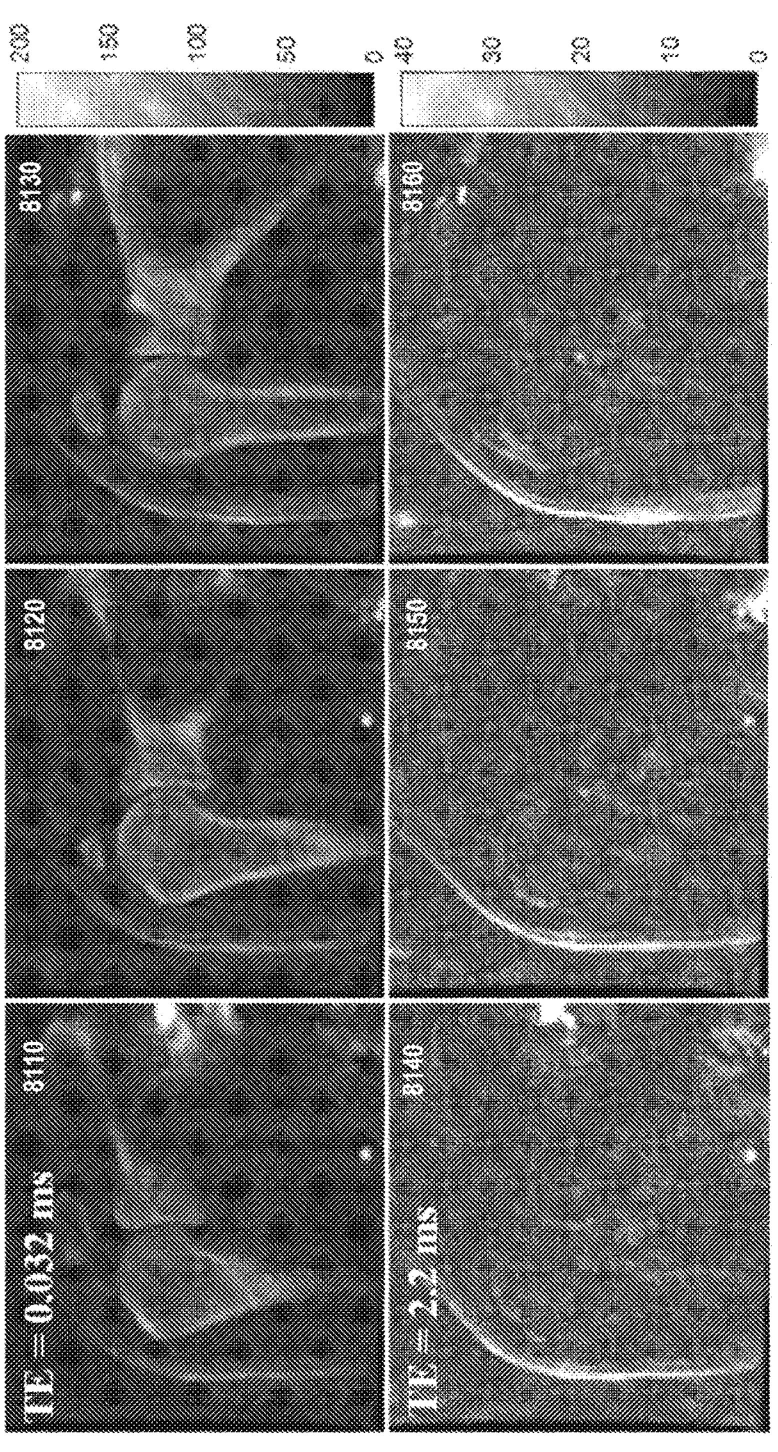
FIG. 8 shows shoulder sample images that are obtained using a dual-echo 3D SIR-UTE sequence.

FIG. 8 shows shoulder sample images that are obtained using a dual-echo 3D SIR-UTE sequence. The first echo images 8110, 820, 8130 show high contrast for cortical and trabecular bone. Almost no signal appeared in the second echo images 8140, 8150, 8160 with a TE of 2.2 ms, suggesting near perfect nulling of long T2 components such bone marrow and muscle. Thus, the second echo images 8140, 8150, 8160 show almost no signals inside of the trabecular bone, which demonstrates excellent suppression of marrow fat.

Figure 9:
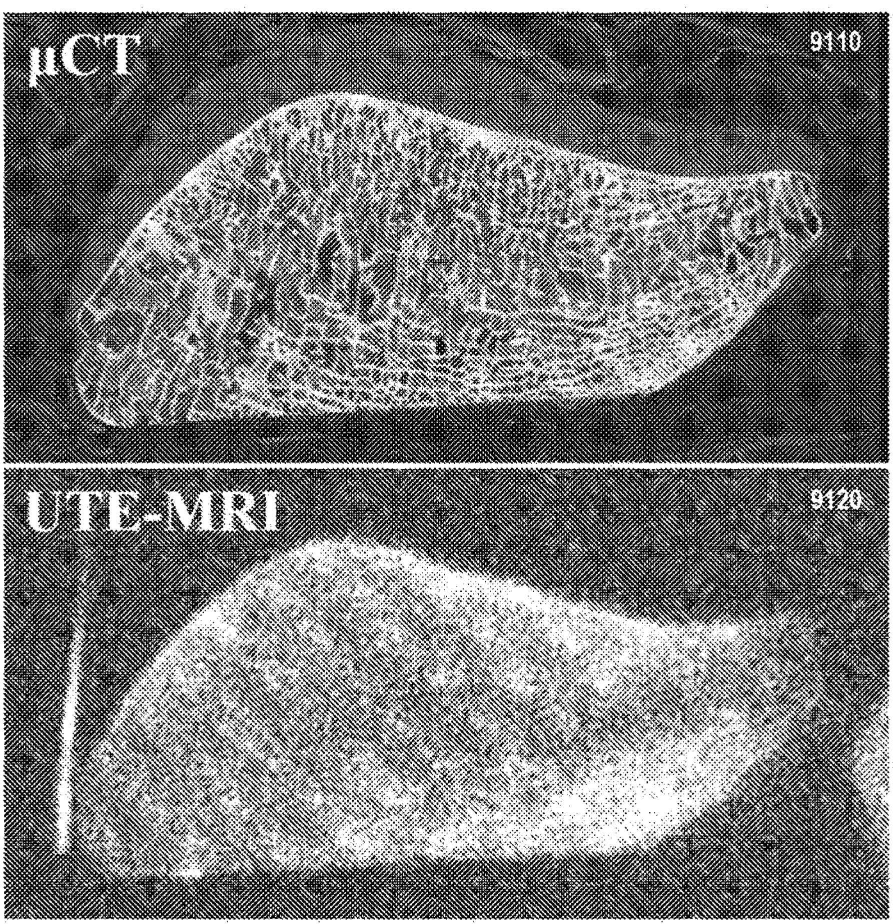
FIG. 9 shows a comparison between SIR-UTE imaging and μCT imaging for a patellar cartilage sample.

FIG. 9 shows a comparison between SIR-UTE imaging and μCT imaging for a patellar cartilage sample. The image 9110 is obtained using co-registered high-resolution μCT and the image 9120 is obtained using SIR-UTE MR. The signal intensity distributions in both images 9110 and 9120 are quite similar, suggesting trabecular bone being selectively imaged with the SIR-UTE sequence. Signal intensity distribution in the SIR-UTE image is highly correlated with that in the μCT image, suggesting that trabecular bone as well as subchondral bone plate were selectively imaged with the 3D SIR-UTE sequence.

Figure 10:
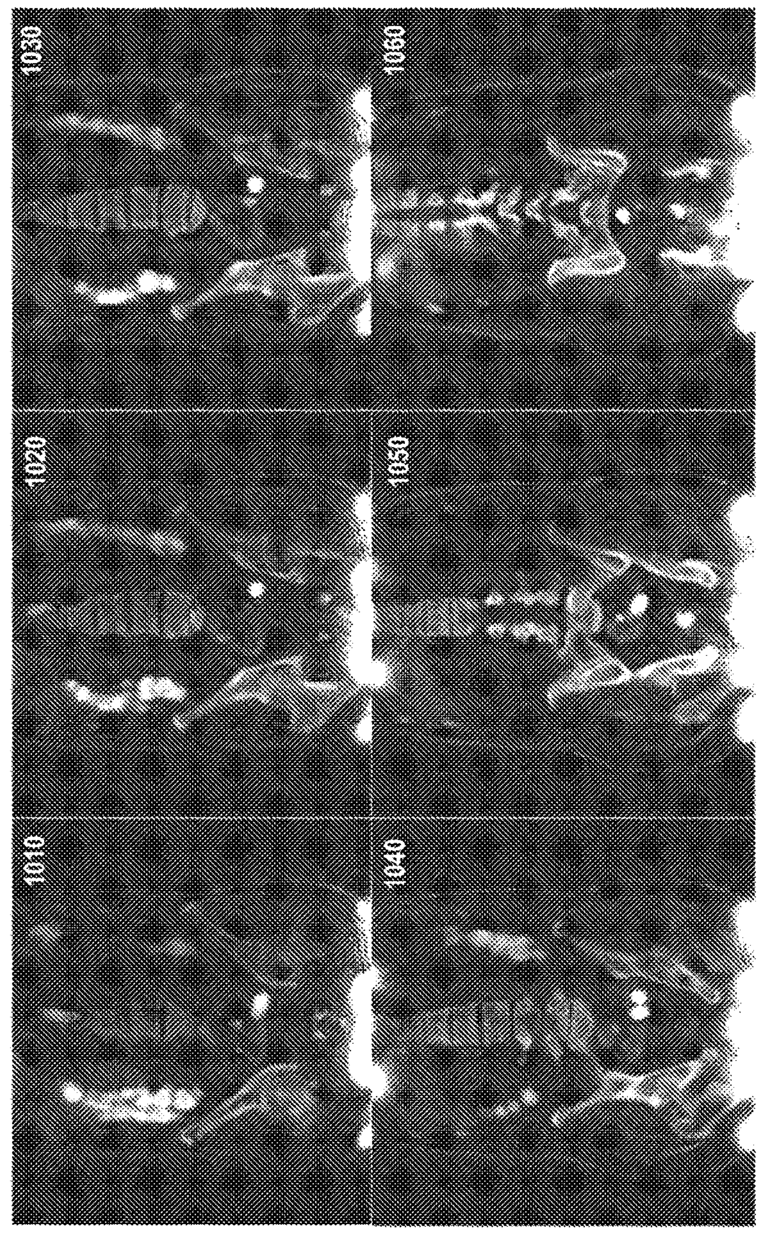
FIG. 10 shows in vivo spine and hip cortical and trabecular bone imaging using the 3D SIR-UTE sequence.

FIG. 10 shows in vivo spine and hip cortical and trabecular bone imaging using the 3D SIR-UTE sequence. The images 1010 to 1060 demonstrate the clinical feasibility of this technique for direct imaging of cortical and trabecular bone in the hip in vivo. using the 3D SIR-UTE sequence.

Figure 11:
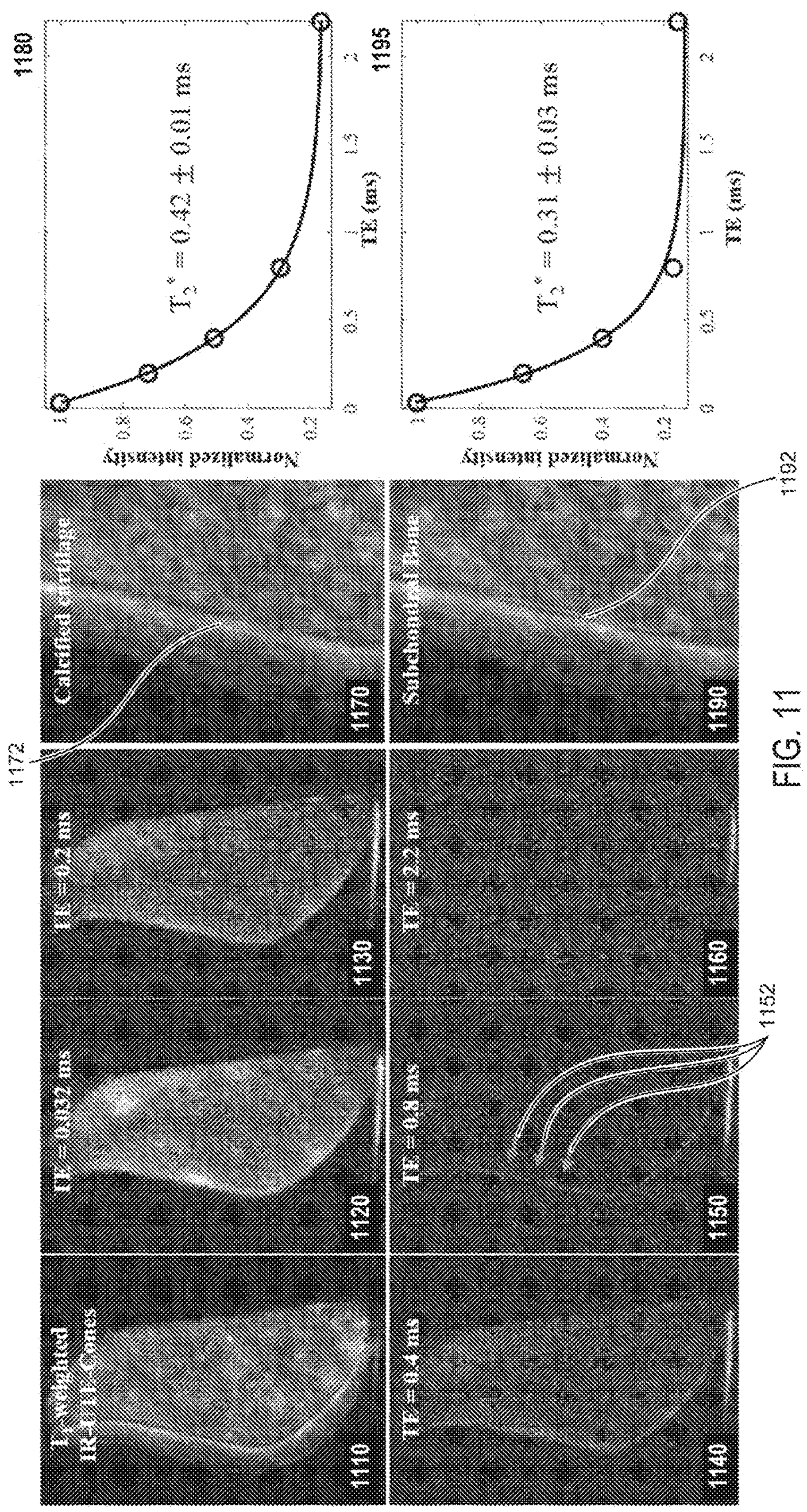
FIG. 11 shows 3D SIR-UTE imaging and quantitative T2* measurements of calcified cartilage and subchondral bone.

FIG. 11 shows 3D SIR-UTE imaging and quantitative T2* measurements of calcified cartilage and subchondral bone. A high contrast OCJ region image 1110 with the T1-weighted SIR-UTE (TR/TI=1200/450 ms) is used to define the position of the calcified cartilage and subchondral bone. Short T2 images (TE=0.032, 0.2, 0.4, 0.8 and 2.2 ms) are shown in the images 1120 to 1160. These can be acquired with a short TR SIR-UTE (e.g., TR/TI=133/58 ms). The T2* s of the calcified cartilage and subchondral bone plate in the short T2 SIR-UTE imaging can be measured. In the example simulation, the T2* of calcified cartilage (line 1172 in the image 1170) and subchondral bone (line 1192 in the image 1190) were 0.42±0.01 ms (see graph 1180) and 0.31±0.03 ms (see graph 1195), respectively. Both tissues have extremely short T2* values (0.42±0.01 ms and 0.31±0.03 ms respectively, see 1180 and 1195). The region in the image 1150 as indicated by the arrows 1152 is the same calcified cartilage which is shown in the line 1172 in the image 1170. Trabecular bone in the patella can also be quantified and its T2* is similar to that of subchondral bone.

Figure 12A:
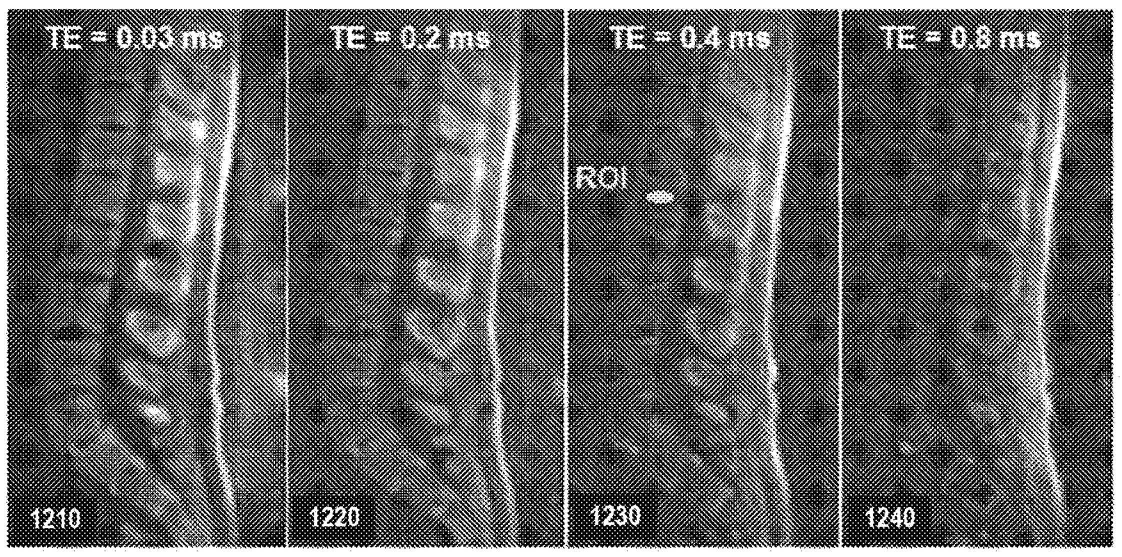
FIG. 12A illustrates 3D SIR-UTE imaging of a spine of a volunteer with a series of TEs.
Figure 12B:
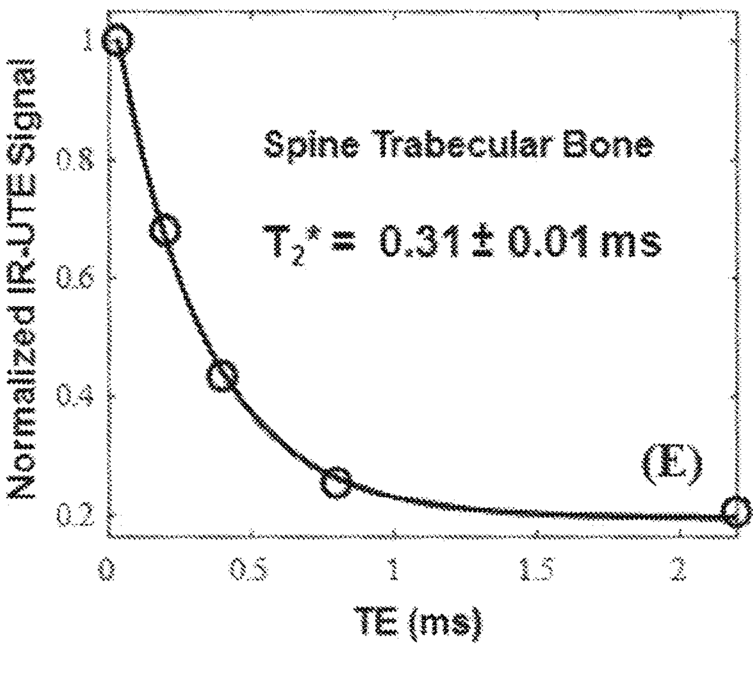
FIG. 12B shows a corresponding T2* fitting curve for an ROI drawn in a spine.

FIG. 12A illustrates 3D IR-UTE imaging of the spine of a volunteer with a series of TEs, which enables to measure T2* of the trabecular bone in the spine. The volunteer is 46-year-old female. Images 1210, 1220, 1230, 1240 correspond to 3D IR-UTE images of the spine of the volunteer in the sagittal plane with a TE of 0.032 m, 0.2 ms, 0.4 ms, and 0.8 ms, respectively. FIG. 12B shows a corresponding T2* fitting curve for an ROI drawn in the spine. A short T2* of 0.31 was demonstrated for trabecular bone, which is consistent with T2* of bound water in cortical bone, suggesting complete suppression of marrow fat and pore water in trabecular bone with the 3D IR-UTE sequence.

Figures 13A, 13B:
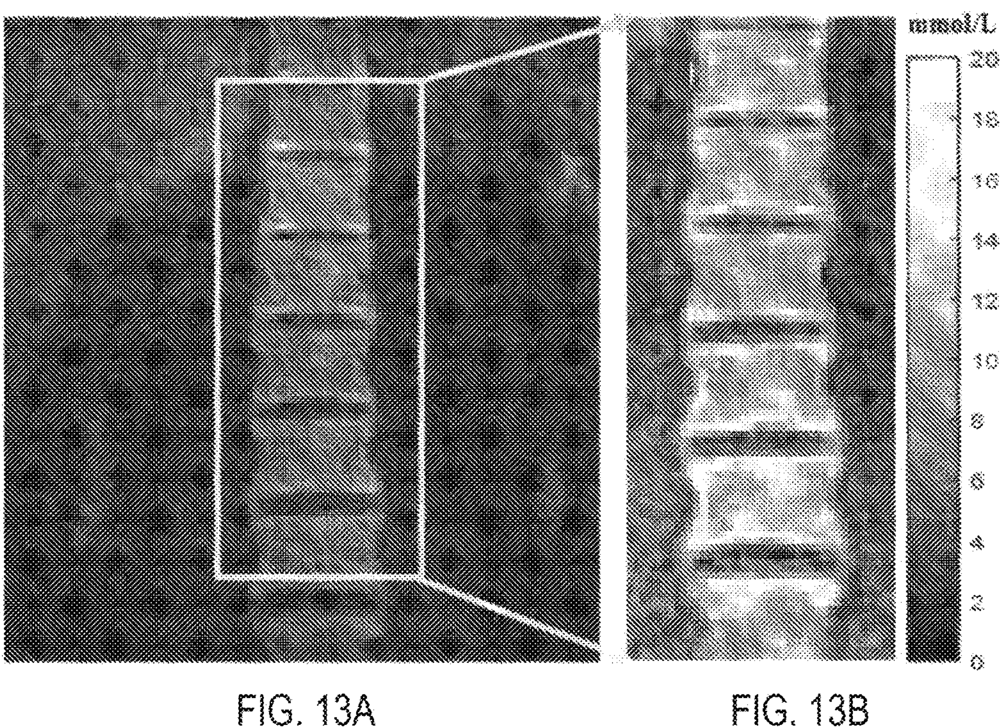
FIGS. 13A to 13D illustrate 3D SIR-UTE imaging and mapping of bound water in a spine.
Figures 13C, 13D:
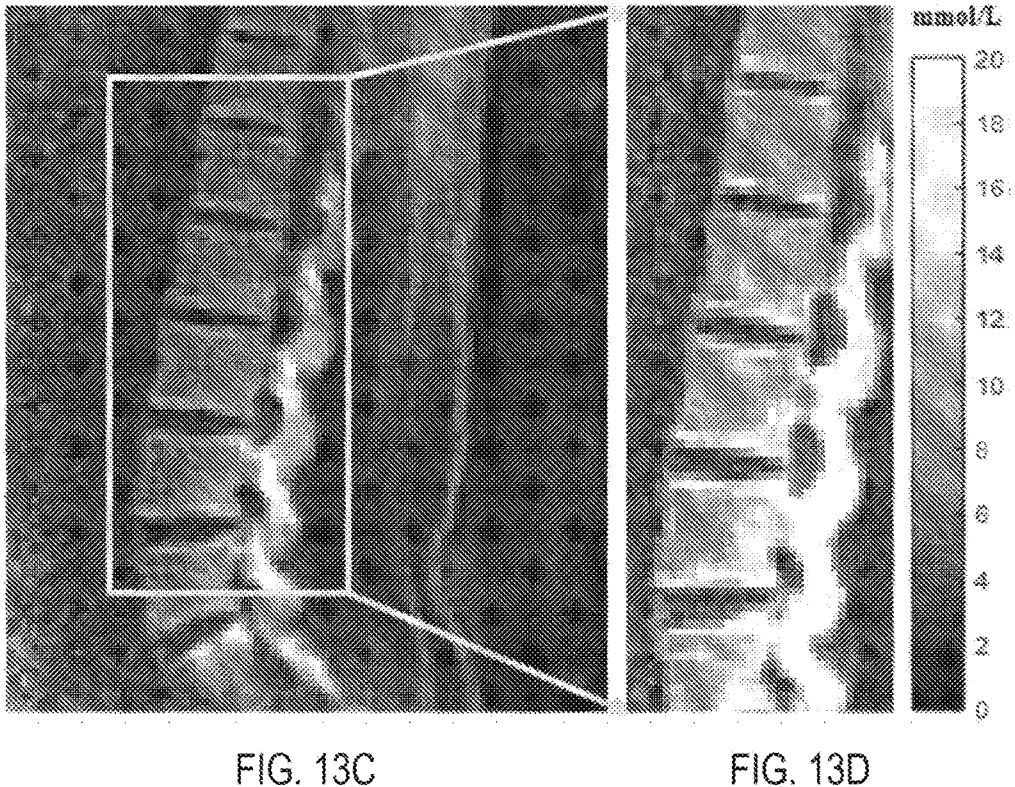

FIGS. 13A to 13D illustrate 3D SIR-UTE imaging and mapping of bound water in the spine of a volunteer. The volunteer is 46-year-old female. FIGS. 13A and 13C show a 3D IR-UTE imaging of the spine in the coronal and sagittal plane, respectively, and FIGS. 13B and 13D show the corresponding bound water mapping for cortical and trabecular bone as well as ligaments. It is possible to apply the same protocol to map bound water in the femoral head and neck. It is also possible to measure total water, bound water and pore water concentrations as well as collagen backbone proton densities for cortical bone ex vivo.

The following descriptions explain the different stages of the aspects of the disclosed technology based on some implementations of the disclosed technology.

Stage 1: IR-UTE Imaging of Cortical and Trabecular Bone

UTE sequences can be used for direct imaging of cortical bone. Adiabatic inversion recovery preparation pulses are proposed for long T2 signal suppression through adiabatic inversion and signal nulling. Due to the very high signal from marrow fat, and muscle which all have long T2 and much higher proton density, it is very challenging to directly image trabecular bone. To address issues on direct imaging of cortical and trabecular bone, using a broad bandwidth single adiabatic inversion recovery (SIR) pulse for robust inversion of marrow fat, and potentially selective imaging of bound water in cortical and trabecular bone are proposed. In some implementations, the use of a broad bandwidth double adiabatic inversion recovery (DIR) pulse for more robust suppression of long T2 tissues such as muscle, marrow fat and pore water with a broad range of T1s is proposed. In some implementations, the use of a soft-hard composite pulse for water excitation, with much reduced fat signal excitation is proposed. This composite pulse together with the SIR and DIR preparation scheme may further improve the robustness of the technique in selective imaging of bound water in cortical and trabecular bone.

Stage 2: Simulation Stage for 3D SIR-UTE and DIR-UTE Imaging of Cortical and Trabecular Bone Computer simulation can be performed regarding long T2 suppression with a broad bandwidth adiabatic inversion recovery preparation pulse, as well as DIR pulse. The results suggest that indeed muscle and marrow fat can be well suppressed with proper combination of TR and TI, and especially TI1 and TI2 in DIR preparation. Computer simulation suggests that the soft-hard composite pulse is very efficient in water excitation with minimal fat signal excitation.

Stage 3: Experimental Data Stage for 3D SIR-UTE and DIR-UTE Techniques

To implement broad band adiabatic inversion pulses, the 3D single adiabatic inversion pulse prepared (SIR) UTE technique on patella specimens can be tested. Through various simulations, outstanding image quality was achieved with the 3D IR-UTE technique, providing high contrast imaging of the calcified cartilage, subchondral bone plate and trabecular bone. T2* was also measured. There was no fat/water oscillation in the T2* decay curve, confirming that marrow fat was selectively and robustly suppressed, and the 3D IR-UTE signal was from bound water in cortical and trabecular bone.

It is expected that the combination of the soft-hard composite pulse with SIR-UTE and DIR-UTE acquisitions can provide high contrast images of bound water in cortical and trabecular bone. The efficiency of fat and pore water excitation would require histology study of trabecular bone specimens (e.g., spine and hip specimens). Related studies are under progress.

Stage 4: Prototype Stage for 3D SIR-UTE and DIR-UTE Imaging of Cortical and Trabecular Bone Some phantoms, ex vivo and in vivo studies can be designed to evaluate the 3D SIR-UTE and DIR-UTE method. Ex vivo and in vivo studies can be used to investigate the accuracy of the proposed method for robust suppression of marrow fat and muscle for high contrast imaging of cortical and trabecular bone on a clinical 3T scanner. All studies show consistent and robust results. The 3D SIR-UTE and DIR-UTE techniques can reliably measure T1 and T2* as well as bound water concentration for cortical and trabecular bone ex vivo and in vivo (preliminary results are shown in FIG. 7A to 12).

The potential commercial applications of the 3D SIR-UTE and DIR-UTE techniques include the following:

1) Osteoporosis: The 3D SIR-UTE and DIR-UTE techniques, especially with potential combination of the soft-hard composite excitation pulse, allows robust suppression of long T2 marrow fat, muscle, and pore water, leaving bound water being selectively imaged. The techniques allow quantitative evaluation of T1 and T2* relaxation times of bound water, providing biomarkers of cortical and trabecular bone quality. The imaging techniques suggested can apply to a bone itself instead of bone marrow. The disclosed techniques may be effectively used to perform imaging of such bones to generate clinical actionable data. The techniques also allow quantitative evaluation of bound water concentration, a biomarker of organic matrix density or bone quantity. The techniques can also be used to quantify cortical bone properties (T1, T2* and bound water content). The techniques can be applied to cortical and trabecular bone at various sites, such as the spine, the hip, the wrist, the shoulder, the ankle, etc. The 3D volumetric information of cortical and trabecular bone quantity and quality is highly likely to be useful for the diagnosis and treatment monitoring of osteoporosis.
2) Osteopenia: The 3D UTE techniques can potentially detect the difference between normal bone, osteoporosis and osteopenia.
3) Osteomalacia: The 3D UTE techniques can potentially differentiate reduced bone content (i.e., reduced organic matrix and mineral) from reduced bone mineralization (i.e., normal organic matrix, reduced bone mineral). Therefore, they can potentially provide more accurate diagnosis of osteomalacia.
4) Renal osteodystrophy (ROD): ROD has been redefined as alterations in bone morphology associated with chronic kidney disease (CKD). A definitive diagnosis of ROD and the identification of histologic subtype requires bone biopsy followed by histomorphometry. Therefore, the diagnosis is invasive and expensive. The UTE MRI techniques developed in this proposal can potentially accurately diagnose ROD, separating it from other metabolic bone diseases such as OP, osteopenia and early stages of chronic kidney disease—mineral bone disorder (CKD-MBD). Compared to the general population, a 2-fold increase in hip fracture risk in patients with moderate-to-severe kidney disease, a 4-fold increase in hemodialysis patients and an 80-fold increase in young dialysis patients (<45 yo) have been observed. The 3D UTE MRI techniques may be especially useful for this group of patients.
5) CKD-MBD: CKD-MBD is used to describe a broader clinical syndrome that develops as a systemic disorder of mineral and bone metabolism due to CKD. CKD-MBD affects more than 22 million Americans. UTE measures can potentially be used to investigate changes in water, collagen and mineral in CKD-MBD patients, thus helping diagnosis and treatment monitoring of CKD-MBD.

Volumetric Mapping of Hydrogen Proton Pools

Some implementations of the disclosed technology relate to techniques for a volumetric mapping of hydrogen proton pools present in bone, e.g., bound water protons, pore water protons, and collagen backbone, or macromolecular protons. Cortical bone assessment using magnetic resonance imaging (MRI) has recently received great attention in an effort to avoid potential harms associated with ionizing radiation-based techniques. Ultrashort echo time MRI (UTE-MRI) techniques can acquire signal from major hydrogen proton pools in cortical bone, including bound and pore water, as well as from the collagen matrix. This study aimed to develop and evaluate the feasibility of a technique for mapping bound water, pore water, and collagen proton densities in human cortical bone ex vivo and in vivo using three-dimensional UTE Cones (3D UTE-Cones) MRI. Eight human tibial cortical bone specimens (63±19 years old) were scanned using 3D UTE-Cones sequences on a clinical 3T scanner and a micro-computed tomography (μCT) scanner. Total, bound, and pore water proton densities (TWPD, BWPD, and PWPD, respectively) were measured using UTE and inversion recovery UTE (IR-UTE) imaging techniques. Macromolecular proton density (MMPD), a collagen representation, was measured using TWPD and macromolecular fraction (MMF) obtained from two-pool UTE magnetization transfer (UTE-MT) modeling. The correlations between proton densities and μCT-based measures were investigated. The 3D UTE-Cones techniques were further applied on ten young healthy volunteers (34±3 years old) and five old female volunteers (78±6 years old) to evaluate the techniques' feasibility for translational clinical applications. In the ex vivo study, PWPD showed the highest correlations with bone porosity and bone mineral density (BMD) (R=0.79 and −0.70, P<0.01). MMPD demonstrated moderate to strong correlations with bone porosity and BMD (R=−0.67 and 0.65, P<0.01). MMPD showed strong correlation with age in specimens from female donors (R=−0.91, P=0.03, n=5). The presented comprehensive 3D UTE-Cones imaging protocol allows quantitative mapping of protons in major pools of cortical bone ex vivo and in vivo. PWPD and MMPD can serve as potential novel biomarkers to assess bone matrix and microstructure, as well as bone age- or injury-related variations.

Cortical bone assessment using magnetic resonance imaging (Mill) has recently received great attention in an effort to avoid potential harms associated with ionizing radiation-based techniques and to investigate the bone's organic matrix. Notably, clinical MRI sequences are not employed for cortical bone imaging because they are not capable of detecting considerable signal from cortical bone. The detected signal intensity of a tissue in MR imaging depends on various factors, including apparent transverse relaxation time (T2*), which is very short in bone. Ultrashort echo time (UTE) MRI can image cortical bone. By employing UTE-MRI techniques, the signal can be acquired a few microseconds after radiofrequency (RF) excitation before a major decay in transverse magnetization.

At least three hydrogen proton pools with different T2* values are present in bone: 1) collagen backbone, or macromolecular, protons, 2) bound water (BW) protons, and 3) pore water (PW) protons. The associated T2* values for the aforementioned proton pools on a 3T MR scanner are <20 μs, 300-400 μs, and >1 ms, respectively. BW content correlates positively with the bone's mechanical properties, while PW content correlates negatively with bone's mechanical properties. The content of macromolecular protons is assumed to be correlated with bone's mechanical and microstructural properties. The T2* of collagen backbone protons is extremely short, so they cannot be imaged directly with UTE sequences on current MRI scanners.

Total water proton density (TWPD) in cortical bone can be estimated by comparing the UTE-MRI signal in cortical bone against an external reference of known water content. The external reference is often a mixture of distilled water and heavy water (e.g., 20% H2O and 80% D2O) doped with $MnCl_2$ and titrated to match the effective T2* of cortical bone. BW proton density (BWPD) in cortical bone has been estimated by comparing the inversion recovery UTE-MRI (IR-UTE-MRI) signal in cortical bone against an external reference. PW proton density (PWPD) can be estimated indirectly by subtracting BWPD from TWPD in cortical bone. In an alternative approach, PWPD can also be estimated using a double adiabatic full passage pulse (DAFP) preparation to saturate the BW signal, followed by UTE acquisition to selectively detect signal from PW.

Magnetization transfer (MT) imaging combined with UTE-MRI has recently been used to indirectly measure the collagen protons' fraction in bone. In UTE-MT, a high-power saturation RF pulse is used with a pre-defined series of frequency offsets from the water protons' resonance frequency to saturate protons mainly in the macromolecular matrix (namely, collagen backbone protons). The saturated magnetization transfers from protons in macromolecules to water protons that can be detected by UTE-MRI. The two-pool model employs UTE-MT data acquired with a series of frequency offsets and MT powers to estimate the macromolecular proton fraction (MMF) and relaxation time, as well as exchange rates. The macromolecular proton density (MMPD) can then be estimated using the MMF derived from UTE-MT modeling and the TWPD derived from UTE imaging.

A comprehensive 3D UTE imaging protocol for volumetric mapping of all the major hydrogen proton pools in bone presented as BWPD, PWPD, TWPD, and MMPD can be developed using the suggested techniques. These proton maps can be generated ex vivo and in vivo in human tibial cortical bone. Such comprehensive proton density mapping could potentially be used to estimate the bone fracture risk in patients. Example materials and methods are discussed in the below.

Proton Density Assessment Theory

Absolute proton density measurement in bone was performed through MRI signal comparison between bone and an external reference of known proton density (20% volume H2O, 80% volume D2O, doped with 24 mmol/L $MnCl_2$, 22 mmol/L $H^1$, T2≈0.35 ms, T1≈6 ms).

Total Water Proton Density (TWPD)

TWPD in cortical bone can be estimated by comparing the UTE signal of cortical bone with that of the external reference. UTE signal can be estimated based on the Ernst equation, as presented in Eq. [3]

$$SI_{Bone}(TE) \propto \frac{1 - e^{-TR/T_{1-TW}}}{1 - \cos\theta \times e^{-TR/T_{1-Tw}}} \times e^{-TE/T_{2-TW}^{*}} \times TWPD \quad [3]$$

where TR, θ, and $T_{1-TW}$ are repetition time, flip angle (FA), and total water longitudinal relaxation time, respectively. A proton density-weighted UTE acquisition can be used to simplify the calculation and minimize potential errors (e.g., a relatively long TR of 100 ms, a short TE of 32 μs, and a low FA of 10° by using a short rectangular excitation pulse of 26 μs). Since T2* Tw and T2* REF are much higher than TE and the rectangular excitation pulse duration, the T2* and T1 effects in Eq.1 can be neglected;

thus, the TWPD can be estimated using Eq. [4] by comparing the UTE signals of bone and external reference.

$$TWPD \approx \frac{SI_{Bone}^{UTE}}{SI_{REF}^{UTE}} \times \eta \times \rho_{REF} \quad [4]$$

where η and $\rho_{REF}$ are coil sensitivity and proton density in the external reference, respectively. When TR is relatively short and FA is not small enough, Eq.1 will be used for more accurate TWPD quantification.

Bound Water Proton Density (BWPD)

BWPD in cortical bone can be estimated by comparing the IR-UTE signal of cortical bone with that of the external reference. The IR-UTE signal can be estimated approximately with Eq. [5], with the assumption of complete saturation of BW, when the pore water nulling is efficient. Thus, BWPD can be calculated using Eq. [6] by comparing the IR-UTE signals of bone and external reference when TE=32 μs, $T2^*_{BW} \approx T2^*_{REF} \approx 350$ μs, and $T_{1\text{-}REF}$=6 ms.

$$SI(t)_{IR-UTE} \propto \left(1 - e^{-TI/T_{1-BW}}\right) \times \sin\theta \times e^{-TE/T_2^*} \times BWPD \quad [5]$$

$$BWPD \approx \frac{SI_{Bone}^{UTE}}{SI_{REF}^{IR-UTE}} \times \eta \times \rho_{REF} \times \frac{1}{1 - e^{-TI/T_{1-BW}}} \quad [6]$$

where $T_{1\text{-}BW}$ is bound water $T_1$.

Pore Water Proton Density (PWPD)

PWPD can be determined by subtracting BWPD from TWPD as shown in Eq. [7].

$$PWPD = TWPD - BWPD \quad [7]$$

Macromolecular Proton Density (MMPD)

MMPD can be calculated using the two-pool MT modeling combined with estimated TWPD (see Eq. [4]). Two-pool MT modeling measures the macromolecular proton fraction, or MMF, which is the ratio between MMPD and all proton densities (TWPD+MMPD). Thus, MMPD can be calculated using Eq. [8].

$$MMPD = \frac{TWPD \times MMF}{1 - MMF} \quad [8]$$

Ex Vivo Proton Density Mapping

Specimen Preparation

Eight cortical bone specimens were harvested from freshly frozen human tibial midshafts (63±19 years old, 5 women, 3 men), provided by a non-profit whole-body donation company (United Tissue Network, AZ, USA). Bone specimens were cut to 30 mm in length using a commercial band saw. Bone marrow that was not trapped in bone pores was removed with a scalpel to avoid later fat dislocation during scans, where the bone specimens are liquid. All bone specimens were immersed in phosphate-buffered saline (PBS) for four hours at room temperature before the MRI scans. Specimens were placed in a plastic container filled with perfluoropolyether (Fomblin, Ausimont, NJ, USA) to minimize dehydration and susceptibility artifacts.

UTE-MR Imaging

The UTE-MRI scans were performed on a 3T MRI (MR750, GE Healthcare Technologies, WI, USA) using an eight-channel knee coil for both RF transmission and signal reception. To measure TWPD, BWPD, and PWPD (Eq.2, 5, and 6), the following imaging protocols were performed to acquire UTE and IR-UTE images: A) a PD-weighted 3D UTE-Cones sequence (TR=100 ms, TEs=0.032 ms, FA=10°, rectangular RF pulse of 26 μs) for TWPD measurement with 3.5 minutes scan time, B) a 3D SIR-UTE sequence (TR=100 ms, TI=45 ms, TEs=0.032 ms, FA=20°, rectangular RF pulse of 56 μs) for BWPD measurement with 3.5 minutes scan time. $T_{1\text{-}BW}$ to be used in Eq.4 was set to 135 ms, as previously measured for eight volunteers. To measure $T_{1\text{-}TW}$ as a prerequisite for the two-pool MT modeling, an actual flip angle-variable TR (AFI-VTR)-based 3D UTE-Cones sequence (AFI: TE=0.032 ms, TRs=20 ms and 100 ms, FA=45°; VTR: TE=0.032 ms, TRs=20, 30, 50, and 100 ms, FA=45°, rectangular RF pulse with a duration of 150 μs) was performed with a total scan time of 20 minutes. Additionally, a 3D UTE-Cones-MT sequence (Fermi saturation pulse power=500°, 1000°, and 1500°; frequency offset=2, 5, 10, 20, and 50 kHz; FA=7°; 9 spokes per MT preparation; rectangular RF excitation pulse of 100 μs) was performed for two-pool MT modelling with a total scan time of 14 minutes. Field of view (FOV), matrix dimension, nominal in-plane pixel size, and slice thickness were 14 cm, 160×160, 0.87 mm, and 2 mm, respectively. At the end, a large homogenous water phantom was imaged using the UTE-MRI protocol to generate the coil sensitivity map (ii) over the selected FOV.

MRI Data Analysis $T_{1\text{-}TW}$ pixel maps were generated based on single-component exponential fittings on the acquired UTE-AFI-VTR data. MMF pixel maps were generated from the acquired MT data using the two-pool MT model. TWPD, BWPD, PWPD, and MMPD pixel maps were generated based on the acquired pixel maps of T1 and MMF, as described in Eq. [2] to [8] using a set of in-house codes developed in MATLAB (version 2017, Mathworks, MA, USA). All maps were smoothed using a Gaussian filter with a 4×4 sub-window.

Micro-Computed Tomography (μCT)

To validate the ex vivo results, the calculated proton densities were compared with intracortical bone porosity (BPO) and mineral density (BMD), which were measured with microcomputed tomography (μCT). All specimens were scanned using a Skyscan 1076 (Kontich, Belgium) μCT scanner at 9 μm isotropic voxel size. For BMD assessment, specimens were scanned in the presence of two hydroxyapatite phantoms (0.25 and 0.5 gr/cm$^3$). Other scanning parameters were as follows: a 0.05 mm aluminum plus 0.038 mm copper filter, 100 kV, 100 mA, 0.4° rotation step, and 5 frame-averaging.

A single gray level threshold was used for μCT image segmentation to distinguish between bone and pores. The threshold was selected for each dataset based on the two major peaks of gray level histograms and visual inspection of the raw images. Thresholding resulted in a stack of binary images. BPO and BMD pixel maps were generated for each specimen by superimposing 222 binary images corresponding to a 2 mm MRI slice.

MRI and μCT Correlations

Proton densities from MRI analyses were compared with BPO and BMD within twelve ROIs per specimen. ROIs were selected by a medical imaging expert at different cortical bone layers and anatomical sites on the UTE images, which provided an adequate range of BPO and BMD. Affine image registration was used to map the ROIs used for MRI analysis on the μCT data. All the data analyses were performed in MATLAB (version 2017, The Mathworks Inc., Natick, MA, USA). Pearson's correlations were calculated between proton densities and μCT-based measures using MATLAB. All ROIs were considered together in statistical correlations in order to examine the UTE-MRI method's capability to detect the variation of bone microstructure regardless of the intracortical bone location. While this does introduce some interdependency between data points, significance levels for all correlations were assessed using non-parametric bootstrap (with resampling by specimen) to adjust for within-specimen dependence. Statistical analyses were performed using a statistical programming language (R, version 3.2.5, R Development Core Team, Vienna, Austria).

In Vivo Proton Density Mapping

Tibial midshafts in ten young (34±3 years old) healthy volunteers and five old (78±6 years old) female volunteers were imaged using the same RF coil and sequences described for ex vivo studies. All in vivo studies were performed with institutional review board approval and written informed consent. Female volunteers were recruited through local advertisement. Pregnant women and unhealthy volunteers were excluded after an initial screening questionnaire. The imaging slab was centered at tibial midshaft localized based on the operator experience. MRI sequences for in vivo imaging were similar to ex vivo imaging, but with higher slice thickness (5 mm) to improve the signal to noise ratio (SNR).

Figure 14:
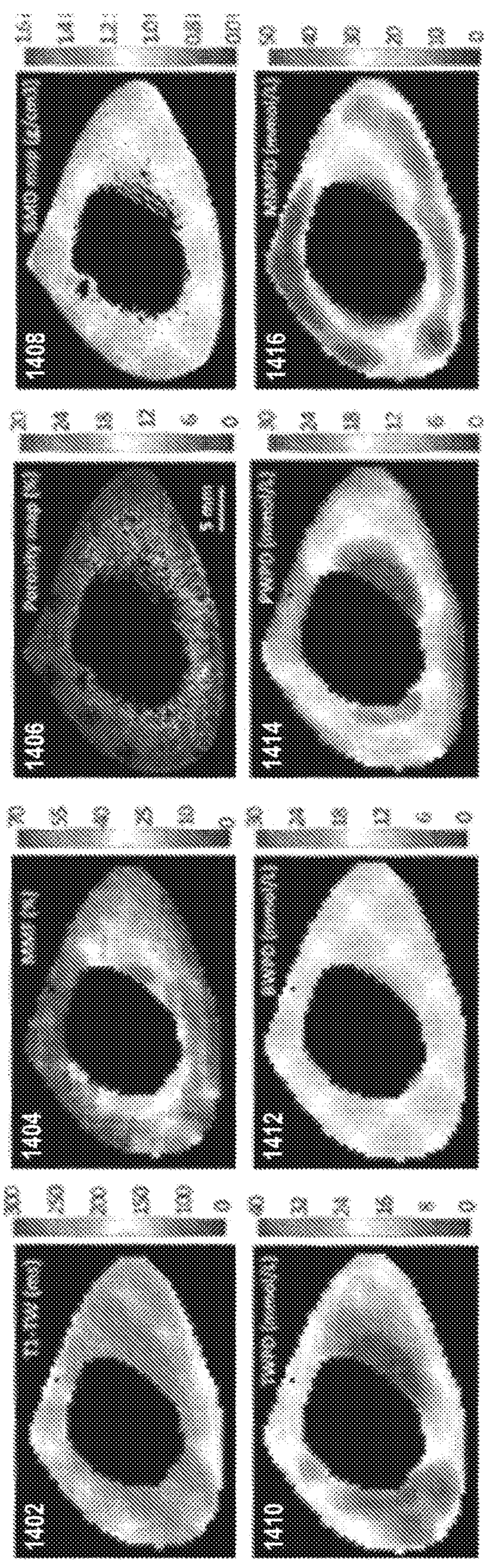
FIG. 14 illustrates sequential steps of a developed method for generating 3D proton density maps and a comparison with μCT for a representative ex vivo tibial specimen.

The following describes the simulation results. FIG. 14 illustrates sequential steps for 3D proton density mapping for a tibial specimen. Steps involved in volumetric proton density mapping for a representative bone specimen includes the image 1402 indicating total water $T_1$ map (T1-TW) derived from 3D UTE-AFI-VTR imaging, the image 1404) indicating macromolecular fraction (MMF) map obtained from MT modeling of Cones-MT imaging, the image 1410 indicating total water proton density (TWPD) map obtained from PD-weighted 3D Cones imaging, the image 1412 indicating bound water proton density (BWPD) map derived from 3D IR-UTE imaging, the image 1414 indicating pore water proton density (PWPD) map derived from the subtraction of TWPD and BWPD, the image 1416 indicating macromolecular proton density (MMPD) derived from TWPD and MMF, the image 1406 indicating bone porosity, the image 1408 indicating mineral density maps were shown for comparison. Volumetric T1 map, macromolecular fraction (MMF) map, total water proton density (TWPD), bound water proton density (BWPD), and pore water proton density (PWPD) maps are generated from various 3D UTE-Cones images. Macromolecular proton density (MMPD) map generated by combining TWPD and MMF is shown in the image 1416. There is a high spatial correlation between 3D UTE-Cones maps of TW, BW, PW, MMF and μCT assessment of cortical porosity and BMD. Total water, bound water and pore water concentrations as well as collagen backbone proton densities for cortical bone in vivo are measured.

Figure 15:
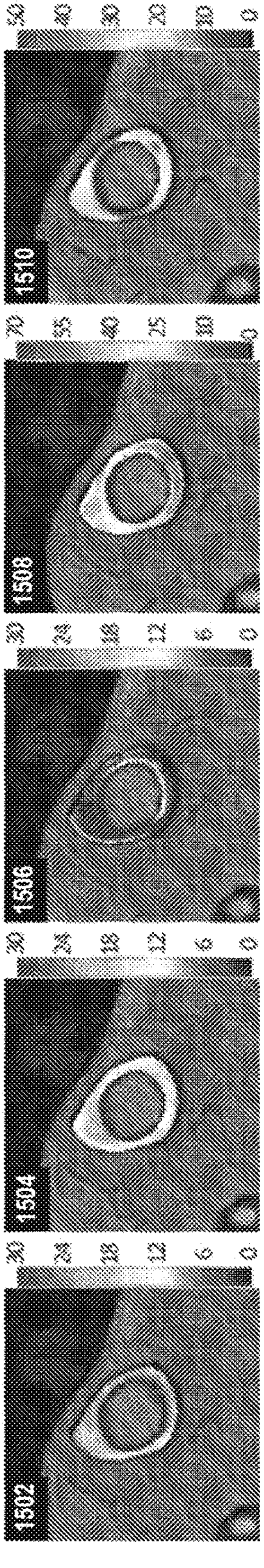
FIG. 15 shows volumetric mapping of total, bound, and pore water and collagen proton concentration for the tibial cortical bone from a healthy volumteer.

Some implementations of the disclosed technology relate to techniques for a volumetric mapping of hydrogen proton pools present in bone, e.g., bound water protons, pore water protons, and collagen backbone, or macromolecular protons. FIG. 15 shows volumetric mapping of total, bound, and pore water as well as collagen proton concentration for a volunteer. The volunteer is a 34-year-old female. The volumetric mapping of hydrogen proton pools presented in bone will be further discussed later in this patent document. FIG. 15 shows some simulation images of volumetric mapping. The images 1502, 1504, 1506, 1508, and 1510 indicate a mapping of total water, bound water, pore water, collagen proton fraction, and collagen proton concentration, respectively. The color bars are in the unit of mmol/L for the images 1502, 1504, 1506, 1510 and in the unit of % for the image 1508.

Figure 16:
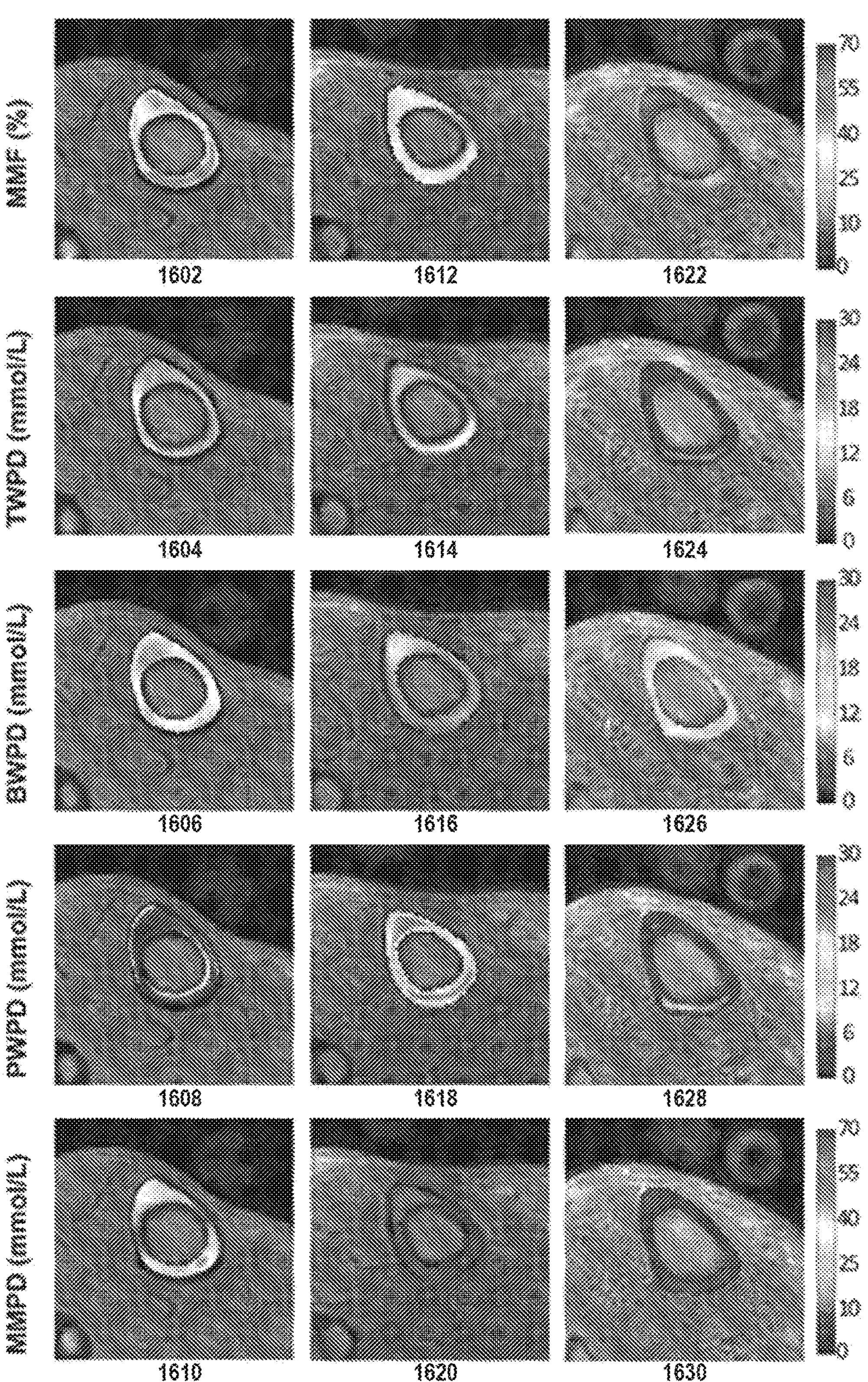
FIG. 16 shows a comparison of volumetric proton density mapping for a young healthy volunteer, female with osteopenia and a patient with renal osteodystrophy.

The 3D UTE MRI allows volumetric mapping of water and collagen in cortical bone in healthy, osteopenia and ROD subjects. FIG. 16 shows volumetric mapping of total, bound and pore water as well as collagen proton density for cortical bone of a 35-year-old healthy female, a 76-year-old female with osteopenia, and a 57 year old female with ROD, respectively. The total scan time including $T_1$ and $T_2$* mapping and MT modeling as well as mapping of total, bound and pore water and collagen protons is around 40 minutes, which is expected to be reduced to less than 30 minutes with further optimization of the acquisition protocols. The images 1602, 1612, 1622 show mapping of total water proton density (TWPD), the images 1604, 1614, 1624 show mapping of bound water PD (BWPD), the images 1606, 1616, 1626 show mapping of pore water PD (PWPD), the images 1608, 1618, 1628 show mapping of macromolecular fraction (MMF), and the images 1610, 1620, 1630 show mapping of macromolecular PD (MMPD) (1610, 1620, 1630) for a 35 year old healthy female ($1^{st}$ row), a 76 year old female with osteopenia ($2^{nd}$ row) and a 57 year old female with ROD ($3^{rd}$ row), respectively. The osteopenia patient ($2^{nd}$ row) and especially the ROD patient ($3^{rd}$ row) show higher PWPD, as well as lower MMF and MMPD. These results demonstrate that 3D UTE sequences allow fast volumetric mapping of total, bound and pore water as well as collagen protons in normal and abnormal bone in vivo on a clinical scanner.

Figures 17A, 17B, 17C, 17D, 17E, 17F:
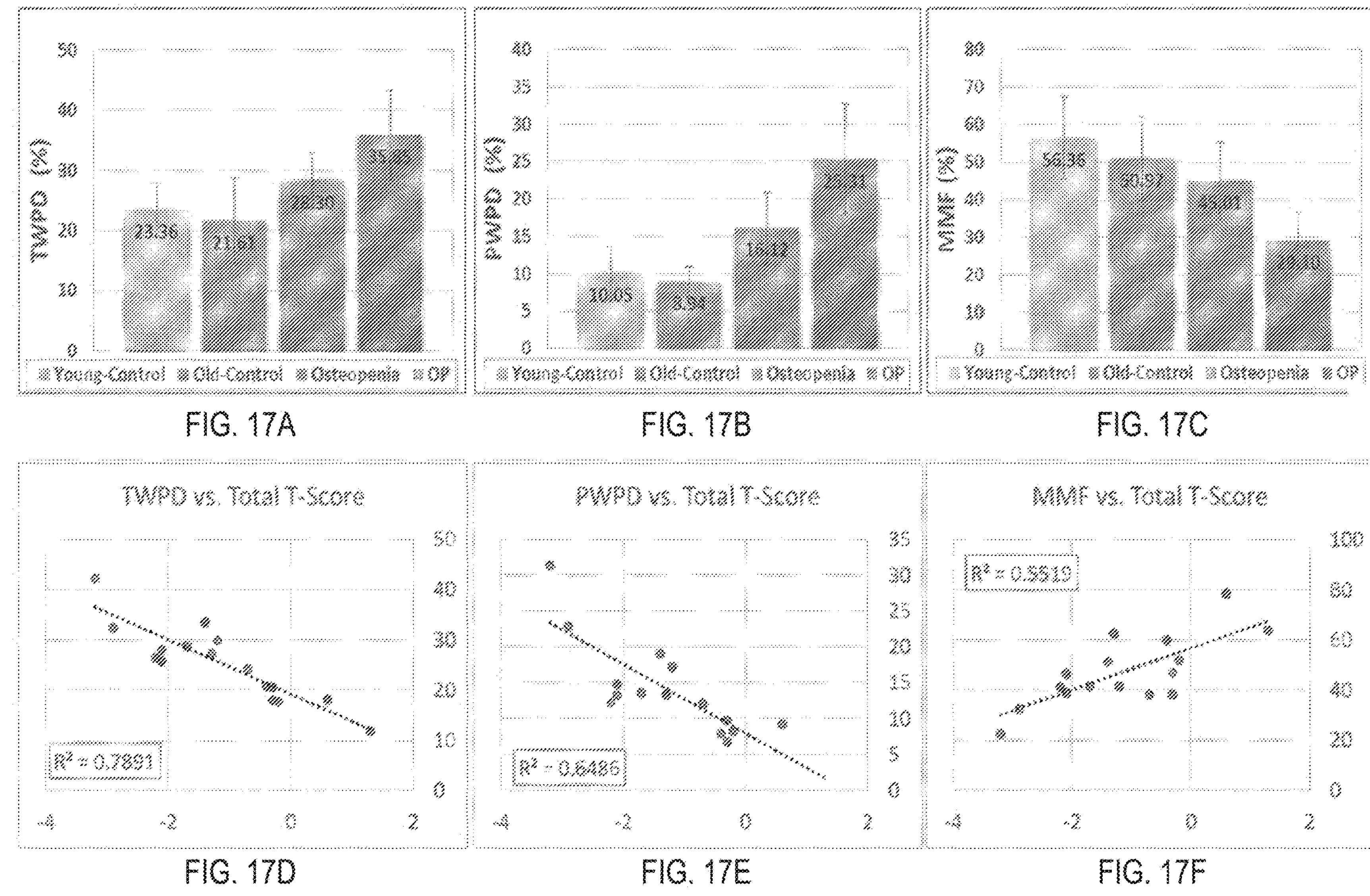
FIGS. 17A to 17C show UTE measured data including total water proton density (TWPD), pore water proton density (PWBD), and macromolecular fraction (MMF).
FIGS. 17D to 17F show the relationship between each UTE measurement and the DEXA T-score.

UTE measured total, bound and pore water as well as collagen proton densities in cortical bone are correlated with DEXA T-score and can differentiate aging and OP, osteopenia and osteomalacia. The simulation has been conducted by applying the bone imaging protocol to 40 female human subjects, including young healthy (n=24, no DEXA score for this group) and older healthy volunteers as well as patients with osteopenia and osteoporosis. There is a clear difference in total, bound and pore water content as well as macromolecular proton fraction and collagen content, as shown in FIGS. 17A to 17F. There is a high correlation between UTE measures with DEXA T-scores. For young (n=24; 28.0±6.3 yo) and old (n=6; 73.7±5.7 yo) healthy women, and women with osteopenia (n=7; 72.7±5.0 yo) and OP (n=3; 82.1±2.5 yo), FIG. 17A shows total water proton density (TWPD), FIG. 17B shows pore water proton density (PWBD), FIG. 17C shows macromolecular fraction (MMF). The results shown in FIGS. 17A to 17C are UTE measured data. There is clear difference between those groups, with higher TWPD and PWPD, and lower MMF for OP patients. As shown in FIGS. 17D to 17F, there is a high linear relationship between UTE measured TWPD ($R^2$=0.7891) (see FIG. 17D), PWPD ($R^2$=0.6486) (see FIG. 17E) and MMF ($R^2$=0.5519) (see FIG. 17F) with DEXA T-score. Those results suggest that cones imaging of cortical bone may be useful in differentiating aging and metabolic bone diseases, including OP, osteopenia and osteomalacia. Improved correlation may be achieved by using a more comprehensive multiparametric analysis since our UTE protocol provides a panel of biomarkers including total water, bound water, pore water, collagen backbone proton fraction, exchange rate and density, $T_1$, $T_2$* and magnetization transfer ratio (MTR). Together the biomarker panel approach may greatly enhance the diagnosis and treatment monitoring of various metabolic bone disease, including but not limited to OP, osteopenia and osteomalacia.

Figure 18:
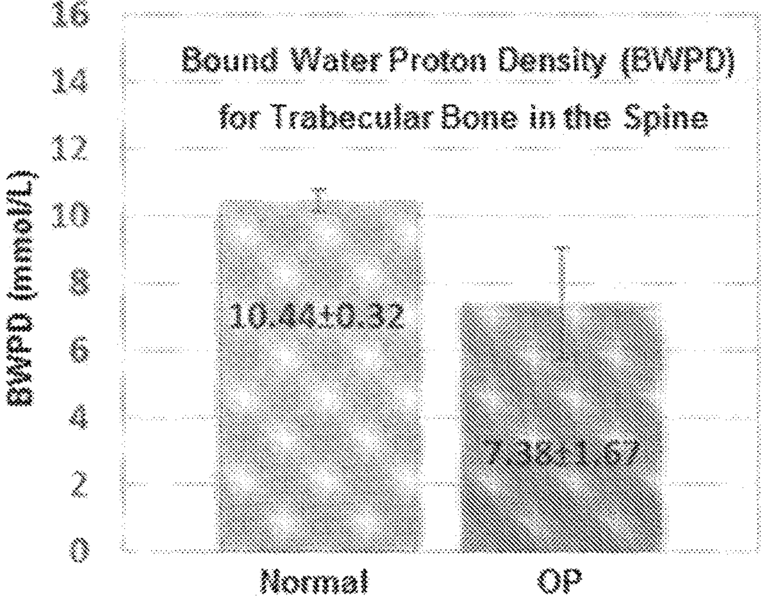
FIG. 18 shows SIR-UTE measured BWPD in the lumbar spine for two groups of women.

UTE measured bound water in trabecular bone of the spine differentiates normal bone from OP. FIG. 18 shows SIR-UTE measured BWPD in the lumbar spine for two groups of women: normal (n=3) and OP (n=3). The normal (n=3) and OP (n=3) groups have different lumbar spine BWPD. The OP group has ~30% reduction in BWPD, consistent with trabecular bone loss as confirmed by DEXA scans. These results demonstrate that SIR-UTE imaging of trabecular bone in the femoral head and neck as well as lumber spine may be used to differentiate aging and metabolic bone diseases, including OP, osteopenia and osteomalacia. Multiparametric analysis of panels of biomarkers for cortical and trabecular bone may further improve the capability of UTE MRI in more accurate diagnosis and treatment monitoring of OP, osteopenia and osteomalacia.

Figures 19A, 19B, 19C:
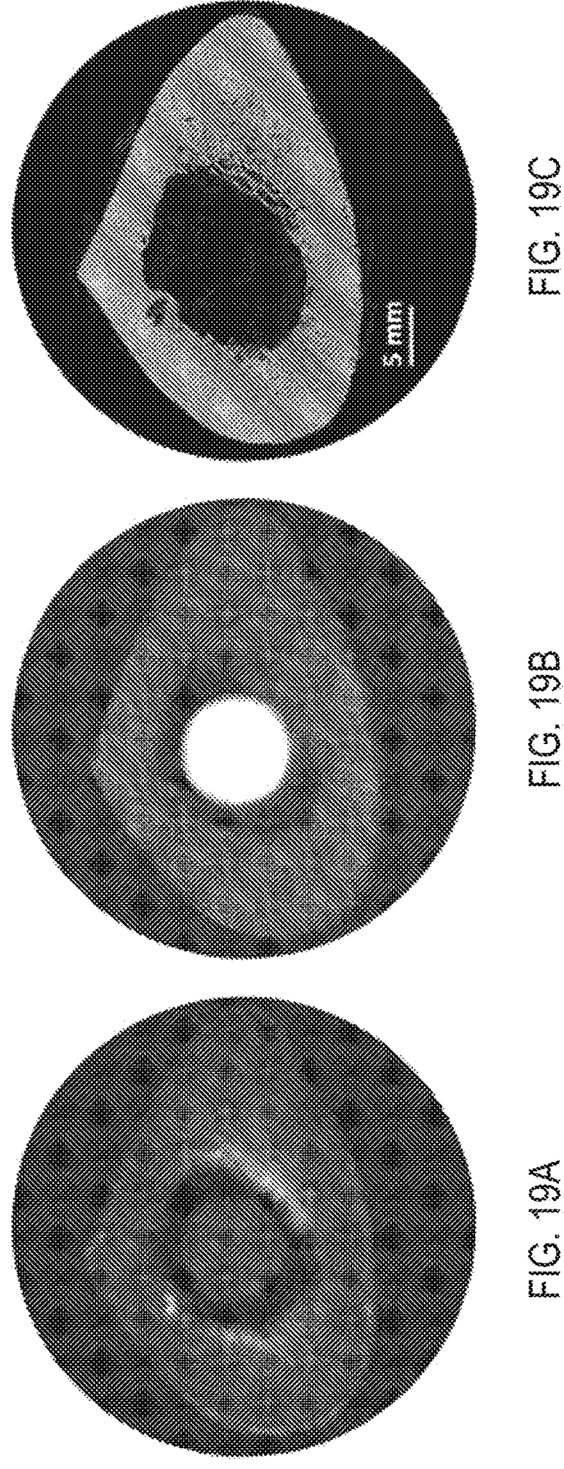
FIGS. 19A to 19C show example images obtained from 3D UTE-Cones imaging, SIR-UTE imaging, and μCT imaging, respectively.

FIGS. 19A to 19C show example images obtained from 3D UTE-Cones imaging, SIR-UTE imaging, and μCT imaging, respectively. FIGS. 19A and 19B show selected 3D UTE-Cones and SIR-UTE imaging of an ex vivo tibial bone specimen from a 73-year-old male donor with marrow removed by scalpel and FIG. 19C shows one of the corresponding μCT images to the selected MRI slice. In external water phantom (20% volume H2O) was placed in the middle of the bone sample for measurement of water and collagen proton densities.

Figure 20:
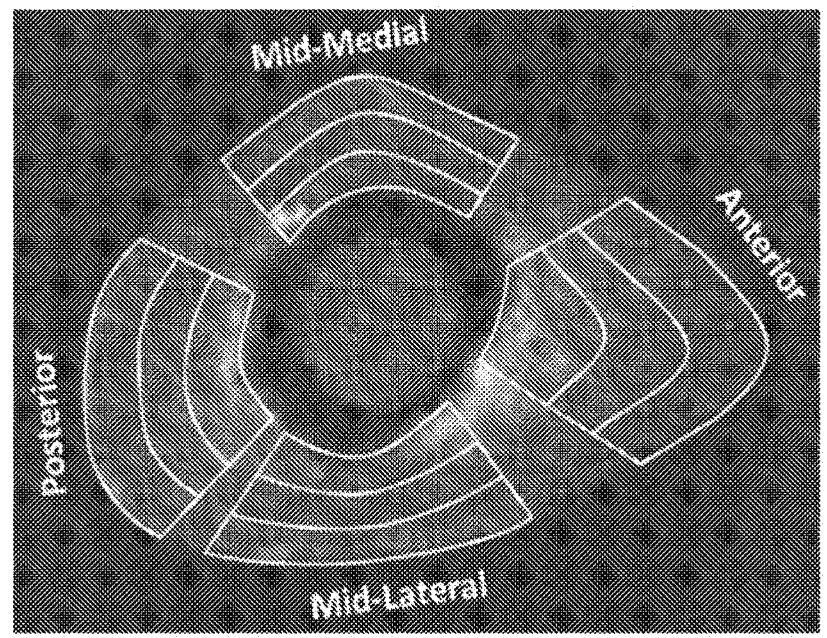
FIG. 20 shows schematic representation of twelve selected ROIs for ex vivo bone specimens.

FIG. 20 shows schematic representation of twelve selected ROIs for ex vivo bone specimens. In FIG. 20, 3 cortical layers and 4 anatomical locations are indicated. The cross-sectional area was divided into three cortical bone layers from endosteum towards periosteum and four anatomical sites including anterior, mid-medial, mid-lateral, and posterior.

Figure 21:
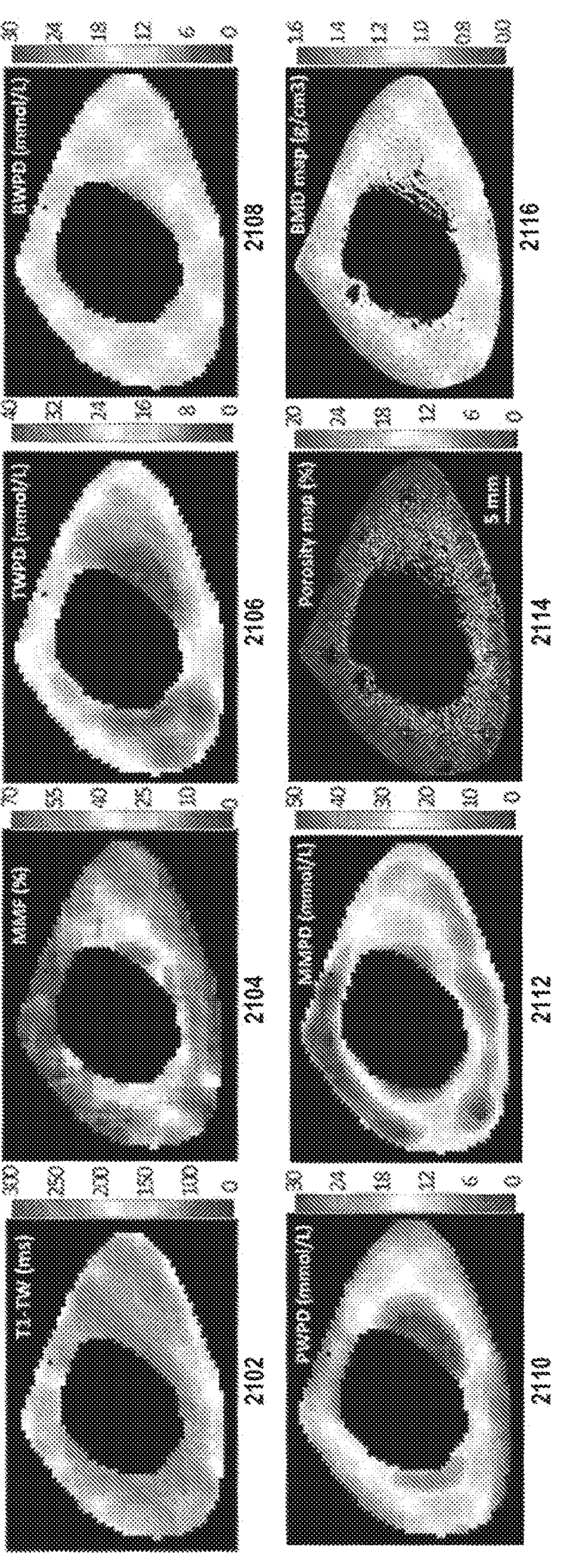
FIG. 21 illustrates sequential steps of the developed method for generating 3D proton density maps for a representative ex vivo tibial specimen.

FIG. 21 illustrates various steps of the developed volumetric proton density mapping method for a representative ex vivo tibial specimen. The image 2102 shows Total water T1 map (T1-TW) derived from 3D UTE-AFI-VTR imaging, the image 2104 shows macromolecular fraction (MMF) map obtained from two-pool MT modeling of 3D UTE-Cones-MT imaging, the image 2104 shows total water proton density (TWPD) map obtained from PD-weighted 3D UTE-Cones imaging, the image 2108 shows bound water proton density (BWPD) map derived from 3D SIR-UTE imaging, the image 2110 shows pore water proton density (PWPD) map derived from the subtraction of TWPD and BWPD, and the image 2112 macromolecular proton density (MMPD) derived from the multiplication of TWPD and MMF. For comparison, the image 2114 showing bone porosity and the image 2116 showing mineral density maps were also generated for 222 corresponding μCT images.

Table 1 below presents the Pearson's correlations, 95% confidence intervals, and p-values between obtained proton densities and μCT-based measures for 96 ROIs in total. Significance for all correlations were assessed using non-parametric bootstrap (with resampling by specimen) to adjust for within-specimen dependence. BPO and BMD demonstrated the highest correlation with PWPD (R=0.79 and R=0.70, p<0.01).

TABLE 1

Pearson's correlations, 95% confidence intervals, and p values between proton densities and μCT results in eight ex vivo tibial cortex (96 ROIs). Significance levels for all correlations were assessed using non-parametric bootstrap (with resampling by specimen) to adjust for within-specimen dependence.

| | TWPD | BWPD | PWPD | MMPD |
|---|---|---|---|---|
| BPO | 0.73 | −0.21 | 0.79 | −0.67 |
| | [0.59, 0.86] | [−0.40, 0.02] | [0.68, 0.89] | [−0.74, −0.55] |
| | P < 0.01 | P = 0.08 | P < 0.01 | P < 0.01 |
| BMD | −0.65 | 0.15 | −0.70 | 0.65 |
| | [−0.82, −0.46] | [−0.08, 0.34] | [−0.86, −0.53] | [0.53, 0.74] |
| | P < 0.01 | P = 0.09 | P < 0.01 | P < 0.01 |

BPO: bone porosity, BMD: bone mineral density.

TWPD, BWPD, PWPD, and MMPD: total water, bound water, pore water, and macromolecular proton densities, respectively.

Figures 22A, 22B, 22C, 22D:
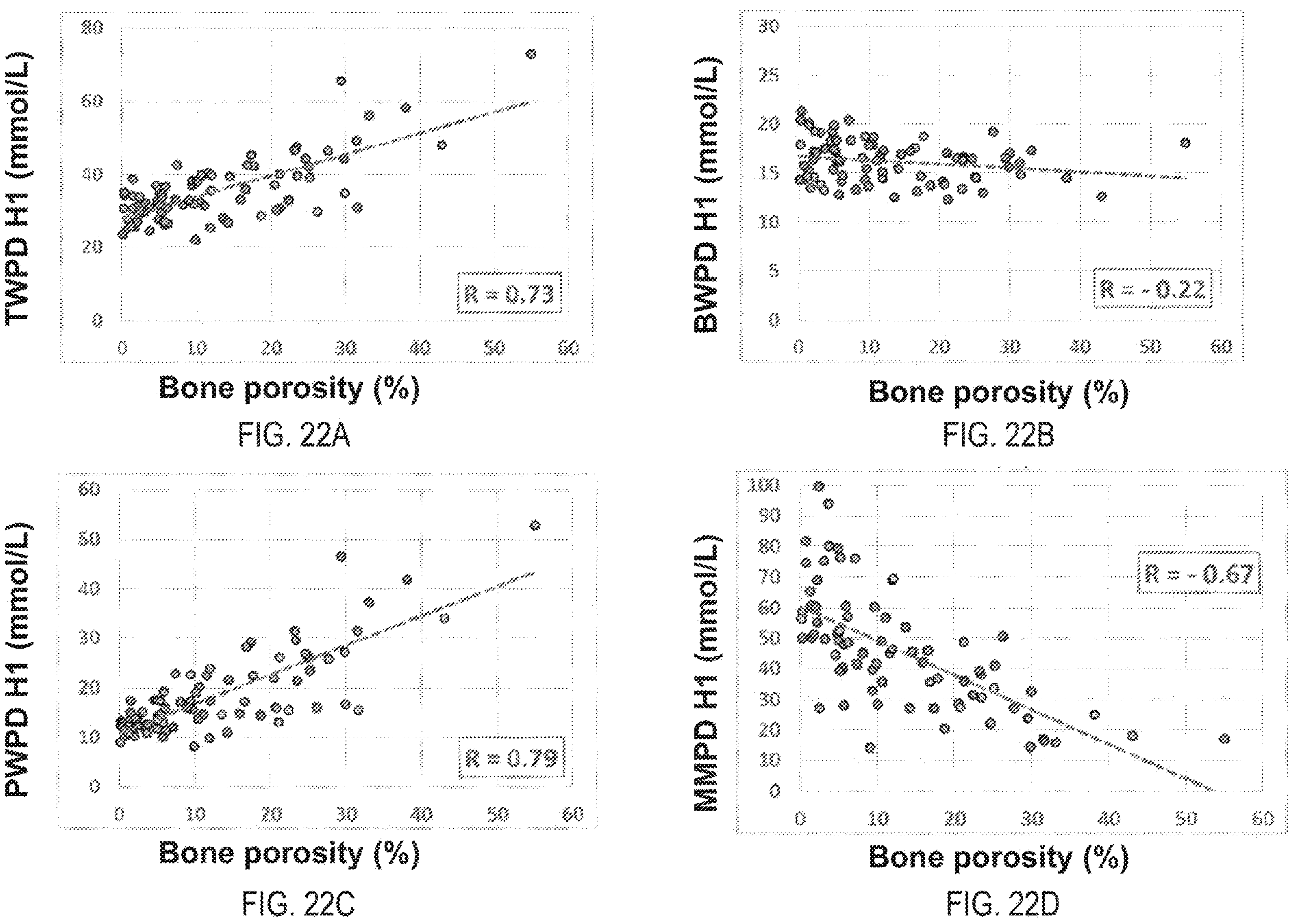
FIGS. 22A to 22D show example scatter plots and linear regression analyses of proton densities and bone porosity (BPO) measured for 96 ROIs from eight bone specimens.

FIG. 22 shows example scatter plots and linear regression analyses of proton densities and bone porosity (BPO) measured for 96 ROIs from eight bone specimens. FIG. 22A shows total water proton density (TWPD) versus μCT-based BPO, FIG. 22B shows bound water proton density (BWPD) versus μCT-based BPO, FIG. 22C shows pore water proton density (PWPD) versus μCT-based BPO, and FIG. 22D shows macromolecular proton density (MMPD) versus μCT-based BPO. While BWPD showed little correlation with BPO, other investigated proton densities showed strong correlations with BPO, with R ranging from 0.67 to 0.79 and P<0.01.

Figure 23:
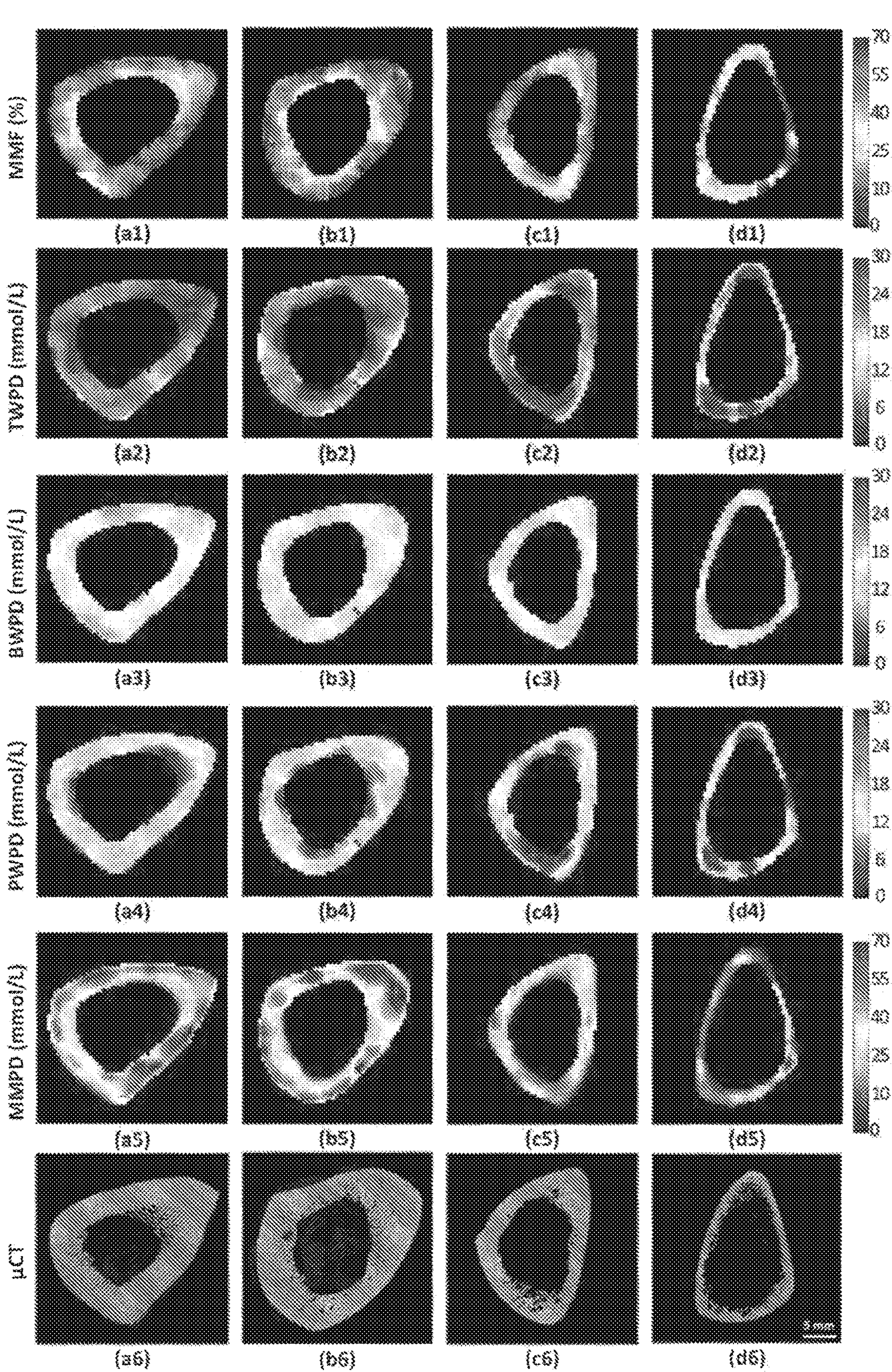
FIG. 23 shows an example of generated proton density maps and corresponding μCT images in four bone specimens.

FIG. 23 shows generated proton density maps and corresponding μCT images in four bone specimens from female donors with various ages at death (i.e., 45, 49, 86, and 95 years old). The images a1 to a6 are from the female volunteer at age of 45, the images b1 to b6 are from the female volunteer at age of 49, the images c1 to c6 are from the female volunteer at age of 95, and the images d1 to d6 are from the female volunteer at age of 86. The images a1 to d1 show macromolecular fraction (MMF) derived from 3D UTE-Cones-MT modeling. The images a2 to d2 show total water proton density (TWPD) maps calculated from PD-weighed 3D UTE-Cones imaging. The images a3 to d3 show bound water proton density (BWPD) maps calculated from 3D SIR-UTE imaging. The images a4 to d4 show pore water proton density (PWPD) maps derived from subtraction of TWPD from BWPD. The images a5 to d5 show macromolecular proton density (MMPD) maps derived from TWPD combined with MMF. The images a6 to d6 show corresponding μCT images of the four studied specimens. Local maxima in PWPD corresponds to the sites of higher porosities in μCT images. MMPD in older specimens were significantly lower. Local maxima of PWPD corresponded to higher porosities and large pores presented in μCT images. This indicates strong correlation between PWPD and BPO, as presented in Table 1 and FIGS. 22A to 22D. PWPD was slightly higher on average for the older bone specimens (R=0.43, P=0.47). MMPD was obviously lower for bone specimens from elderly donors. Considering all eight studied bone specimens, average MMPD was found to be moderately correlated (R=0.58, P=0.13) with age. MMPD and age correlation was much stronger (R=0.91, P=0.03) when counting only the limited female specimens (n=5).

Figure 24:
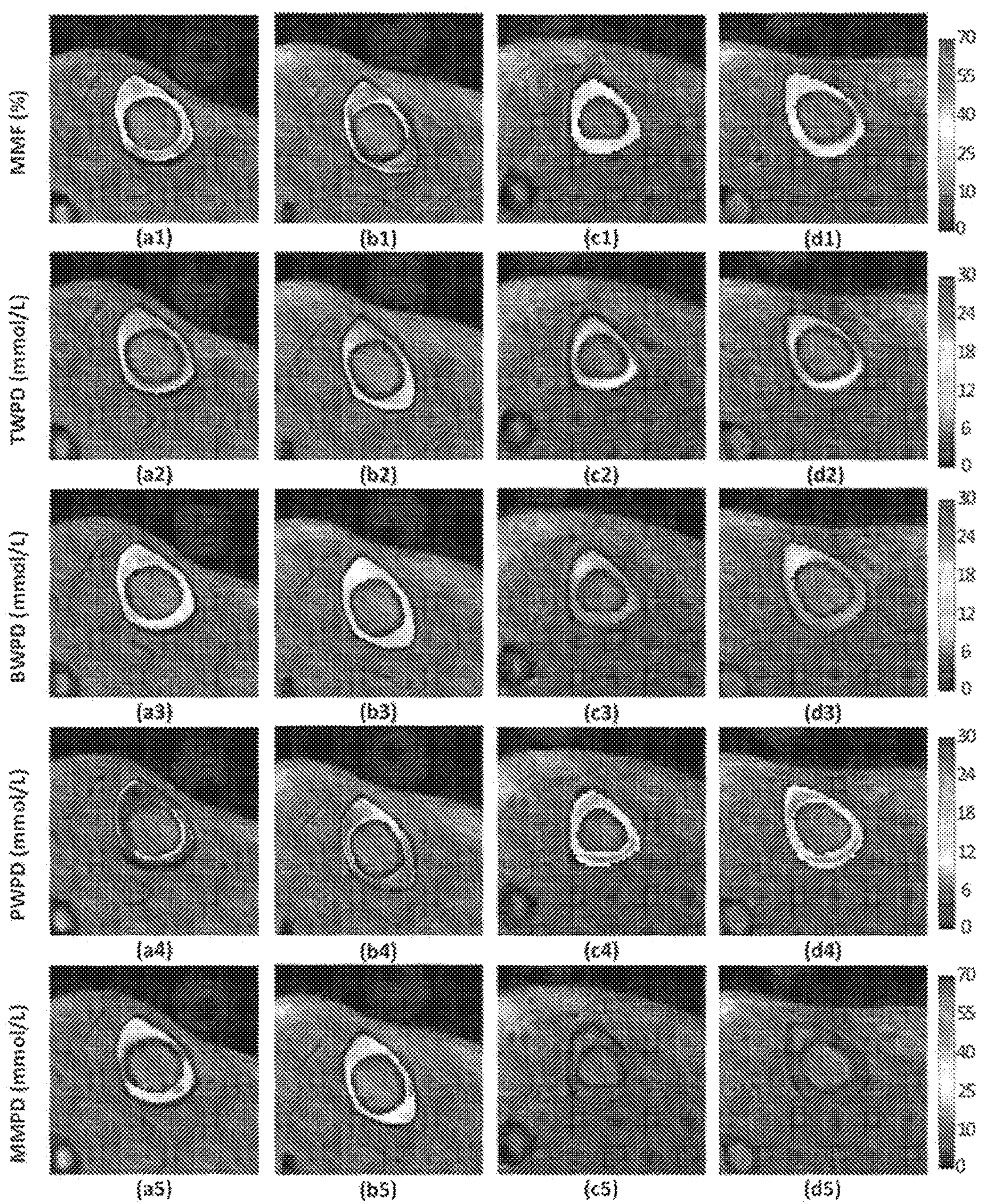
FIG. 24 shows an example of generated proton density maps.

FIG. 24 shows generated proton density maps for two young (33 and 36 years old) healthy and two old (75 and 76 years old) female volunteers. The images a1 to a5 are from 34-year-old female volunteer, the images b1 to b5 are from 35-year-old female volunteer, the images c1 to c5 are from 75-year-old female volunteer, and the images d1 to d5 are from 76-year-old female volunteer. The images a1 to d1 show MMF from 3D UTE-Cones-MT modeling. The images a2 to d2 show total water proton density (TWPD) maps from PD-weighted 3D UTE-Cones imaging. The images a3 to d3 show bound water proton density (BWPD) maps from 3D SIR-UTE imaging. The images a4 to d4 show pore water proton density (PWPD) maps from the subtraction of TWPD from BWPD. The images a5 to d5 show macromolecular proton density (MMPD) maps from TWPD combined with MMF. In older individuals, PWPDs were higher, while BWPDs and MMPDs were lower compared with the younger group.

Table 2 presents the average proton densities from ex vivo (n=8), young in vivo (n=10), and old in vivo (n=5) studies. On average, TWPD and PWPD were higher for old individuals compared with the young groups and the ex vivo scans. Conversely, BWPD and MMPD were lower for the old group compared with the young group and ex vivo study.

TABLE 2

Average proton densities from ex vivo (eight specimens, 63 ± 19 years old) and in vivo (ten young healthy and five old women) studies

| | TWPD (mmol/L) | BWPD (mmol/L) | PWPD (mmol/L) | MMPD (mmol/L) |
|---|---|---|---|---|
| Ex vivo | 35.0 ± 3.2 | 16.0 ± 1.6 | 18.1 ± 2.4 | 44.7 ± 10.2 |
| Young in vivo | 29.3 ± 6.3 | 14.8 ± 2.2 | 14.8 ± 5.3 | 45.8 ± 12.4 |
| Old in vivo | 36.4 ± 8.3 | 13.0 ± 1.7 | 23.4 ± 8.7 | 29.8 ± 14.8 |

TWPD, BWPD, PWPD, and MMPD: total water, bound water, pore water, and macromolecular proton densities, respectively.

This study focused on generating proton density maps for bound and pore water pools as well as for collagen matrix of cortical bone. Density maps of protons in macromolecules (i.e., MMPD) were presented for the first time in this study by combining the two-pool 3D UTE-Cones-MT modeling and TWPD measured using PD-weighted 3D UTE-Cones imaging. MMPD mapping can be potentially used to localize bone injury and weak spots in the bone matrix that are prone to fracture. It is assumed that MMPD represents the bone collagenous matrix spatial distribution and that it potentially correlates with the bone's viscoelastic properties, such as mechanical toughness. Parameters of UTE-MT technique have demonstrated good correlation with human bone porosity.

The accurate estimation of bone water protons requires the consideration of i) different relaxation times between cortical bone and the reference water phantom, ii) variation in coil sensitivity, and iii) RF pulse duration and inhomogeneity (or actual flip angles). Due to short $T_{1\text{-}TW}$ in cortical bone and to the use of a relatively low FA and relatively high TR in the PD-weighted 3D UTE-Cones sequence, the T1 effect on the TWPD calculation could be neglected. Because the T2* s of the external water phantom and bone were similar and because of the use of an ultrashort TE of 32 μs, the T2* term in the proton density measurement could also be neglected (Eq. 1). The IR-UTE signal in cortical bone is typically uniform and smooth; therefore, using a constant value for T1-BW based on the literature was assumed to be practical and accurate ($T_{1\text{-}BW}$=135 ms). For accurate $T_{1\text{-}TW}$ measurement required for MT modeling, the B1 inhomogeneity was corrected to consider the actual FA instead of the nominal FA. Utilizing such pixel maps, rather than the constant values from the literature, will enable more accurate localization of bone matrix variation using MMPD in future translational and longitudinal studies. Furthermore, cortical bone T1 varies significantly between subjects, as well as between different bone sites within certain subjects depending on the bone porosity.

Investigating 96 ROIs from eight specimens revealed significant statistical correlations between μCT-based microstructural measures and proton densities. As expected, bone porosity revealed strong correlation with PWPD (see Table 1, FIGS. 22A to 22D). The PWPD and TWPD correlations with μCT porosity were higher than reported values in previous studies. PWPD showed slightly higher values on average for the two older bone specimens (FIG. 23). Interestingly, MMPD demonstrated more significant differences between the young and old female donors (FIG. 23). Remarkably, MMPD and age correlation was strong within bone specimens from female donors (R=0.91, P=0.03), even though a limited number of specimens was analyzed (n=5). Such a high correlation may weaken when investigating a higher number of specimens.

To investigate the feasibility of the techniques and to initiate the techniques' translation to clinical studies, ten young healthy and five old female volunteers were scanned using the same 3D UTE-Cones MRI sequences and RF coil. For In vivo scans, the slice thickness was higher to provide adequate SNR in images. On average, TWPD and PWPD were significantly higher for old individuals compared with the young group (Table 2). However, MMPD was significantly lower for the old group compared with young group and the ex vivo study. BWPD did not show significant variation between the studied groups.

The ratio between BWPD to PWPD in this study was lower than the reported values in previous studies for tibia. Higher BWPD may have resulted from high $T_{1\text{-}BW}$ values (290 ms) used in previous studies. In the current study, $T_{1\text{-}BW}$ was set to 135 ms based on eight previously scanned subjects.

This study enriches the bone imaging literature currently focused on MRI-based proton density mapping in cortical bone. Here, the technique for mapping MMPD is presented for the first time as a potentially crucial tool for evaluating bone matrix and as a potentially sensitive and novel biomarker of aging. Incorporating the MMPD mapping in cortical bone to the current imaging standard may provide a more comprehensive tool for future bone disease evaluation. Further, the use of 3D UTE-Cones sequences greatly facilitates translational studies due to the much higher efficiency of Cones trajectories over 2D or 3D radial trajectories in sampling k-space data.

For the simulations and experiments discussed, the presented techniques were translated to in vivo applications, only a limited number of healthy and old volunteers were recruited for this feasibility study. However, the techniques and the protocol can be applied to examine a larger cohort of volunteers, especially in patients with osteoporosis and other bone diseases. While the total scan time was approximately 40 minutes in the simulations and experiments, employing different accelerating techniques such as stretching the readout trajectory could be used to accelerate the 3D UTE-Cones sequences and limit the scans to 20 minutes with negligible resulted errors. While the presented technique did not take fat presence in cortical bone into account, particularly in layers near the endosteum, the fat signal contribution may be similar to PW in the UTE-images. The possibility of chemical shift impacting the estimated proton densities needs to be studied in a future investigation. Different fat suppression techniques, such as multi-echo acquisition with IDEAL, Dixon processing, or water excitation, could be an option for those studies. It is suggested that 3D-UTE quantitative susceptibility mapping (3D-UTE-QSM) can be used to measure bone susceptibility, which is highly correlated with BMD. The addition of 3D UTE-Cones-QSM to the current protocol may enable detection of all the components in cortical bone, including bound water, pore water, organic matrix, and bone mineral.

In some implementations, a comprehensive protocol can be presented to map proton densities as exist in water pools and bone matrix in cortical bone. MMPD mapping, based on recently developed two-pool UTE-MT modeling, can be presented. MMPD represents proton density in collagenous bone matrix, which likely varies by aging and by bone injuries. Mapping proton densities is feasible for studied bone specimens and for volunteer subjects. Strong correlations between proton densities and bone microstructure, as measured with high resolution μCT, can validate the presented technique for water proton density measurement. As expected, PWPD showed the highest correlation with bone porosity. Strong correlation between MMPD and donor age, as well as significant differences between young and old in vivo groups, demonstrates the potential of this technique to assess age-related variations in bone matrix. The presented technique can improve and extend the previously reported proton mapping in cortical bone. This technique can potentially serve as a novel tool to assess bone matrix and microstructure, as well as bone age- or injury-related variations in patients.

In some embodiments, a method for imaging cortical and trabecular bones may include suppressing signals from certain tissues in the cortical and trabecular bone using an adiabatic inversion recovery pulse, and performing data acquisition using multiple spokes. For example, the certain tissue may be marrow (fat) or muscle tissue surrounding the bone. The tissue typically may have a large T2 and the bone has a relatively large T2. Example numerical ranges are provided in the description. The signals from the image target may be suppressed by using additional (one or more) adiabatic inversion recovery pulses. Using the method, one of the spokes will be used to null tissue magnetization. In some embodiments, the suppression of signals is performed using techniques including at least one of three-dimensional single adiabatic inversion recovery prepared Ultrashort Echo Time (3D SIR-UTE) or three-dimensional double adiabatic inversion recovery prepared UTE (3D DIR-UTE).

Further Discussion on Numerical Simulation

In the below, the numerical simulations are discussed in more detail. Numerical simulation suggests that the IR technique with a short TR/TI combination provides sufficient suppression of long T2 tissues with a wide range of T1s. High contrast imaging of trabecular bone can be achieved ex vivo and in vivo, with fitted T2* values of 0.3 to 0.45 ms and proton densities of 5-9 mol/L. The 3D SIR-UTE sequence with a short TR/TI combination provides robust suppression of long T2 tissues and allows both selective imaging and quantitative (T2* and proton density) assessment of short T2 water components in trabecular bone in vivo.

As already discussed above, some implementations of the disclosed technology propose a broadband adiabatic inversion recovery prepared three-dimensional UTE Cones (3D SIR-UTE) sequence for direct volumetric imaging of trabecular bone in the human spine and hip (16,17). The combination of a short repetition time (TR) and inversion time (TI) is chosen in order for the SIR-UTE sequence to obtain robust suppression of a variety of long $T_2$ tissues with different Tis. Using the adiabatic full passage (AFP) pulse with a relatively wide bandwidth (~1.6 kHz), the proposed IR preparation is insensitive to both $B_1$ and $B_0$ inhomogeneities (18). Furthermore, multispoke acquisition per IR preparation can be incorporated, allowing time-efficient volumetric imaging and $T_2$* quantification of trabecular bone (17,19). Proton density can also be quantified by comparing 3D SIR-UTE signal of trabecular bone with that of a calibration phantom. Numerical simulations, ex vivo studies, and in vivo studies are conducted to validate the feasibility of the proposed SIR-UTE sequence to directly image and quantify trabecular bone.

Referring back to FIGS. 1A to 1G, it has been discussed that the adiabatic IR pulse can effectively invert the longitudinal magnetizations of long T2 tissues, such as marrow fat and muscle. However, the longitudinal magnetizations of short T2 tissues such as bone are typically saturated, not inverted, by the relatively long adiabatic inversion pulse. Thus, an inversion efficiency factor Q is introduced for the adiabatic IR pulse with a range of −1 (signifying full inversion) to 1 (signifying no disturbance to the z-magnetization). Q is equal to zero in the condition of complete saturation.

To simplify the signal equation, a rectangular pulse is considered for excitation. At steady state, the longitudinal magnetization of the $j^{th}$ spoke is expressed as follows:

$$M_z^j = A(j)M_p + B(j), \quad [9]$$

where $$A(j) = E_1(e_1 f_z)^{j-1}, \quad [10]$$

$$B(j) = M_0(1-E_1)(e_1 f_z)^{j-1} + M_0(1-e_1)\left[1-(e_1 f_z)^{j-1}\right]/(1-e_1 f_z), \quad [11]$$

$$M_p = \frac{Q\left[E_2 B_{N_{sp}} f_z + M_0 E_1(1-E_2)\right]}{1 - Q E_2 A_{N_{sp}} f_z}, \quad [12]$$

using the following definitions: $A_{N_{sp}}=A(N_{sp})$, $B_{N_{sp}}=B(N_{sp})$, $E_1=\exp\{-[TI-\tau(N_{sp}-1)/2]/T_1\}$, $E_2=\exp\{-[TR-TI-\tau(N_{sp}-1)/2]/T_1\}$, and $e_1=\exp(-\tau/T_1)$. $M_0$ is the signal intensity in the equilibrium state. $M_p$ is the longitudinal magnetization after the IR pulse; its explicit derivation can be found in the Appendix section. $f_z$ is the longitudinal magnetization mapping function that describes the response of the magnetization to the RF pulse, with $$f_z(\alpha, \tau, T_2) = M_z^+/M_z^- \cdot M_z^- \text{ and } M_z^+$$

are defined as the longitudinal magnetizations before and after RF excitation. $f_z$ is introduced to account for the signal loss during the RF excitation when tissue $T_2$ is close to or less than RF pulse duration. The expression of the longitudinal magnetization mapping function is shown as follows (23):

$$f_z(\alpha, d, T_2) = e^{\frac{d}{2T_2}}\left(\cos\left(\sqrt{\alpha^2-\left(\frac{d}{2T_2}\right)^2}\right) + \frac{d}{2T_2} sinc\left(\sqrt{\alpha^2-\left(\frac{d}{2T_2}\right)^2}\right)\right), \quad [13]$$

where $\alpha$ is the excitation flip angle and d is the pulse duration. For the tissue with a $T_2 >> d$, the $T_2$ decaying during excitation can be neglected; thus, $f_z$ can be simplified to the conventional cos ($\alpha$).

For short $T_2$ tissues (e.g. $T_2 < 1$ ms), both Q and $M_p$ approach 0. Therefore, Eq. [9] can be simplified to $$M_z^j = B(j).$$

The signal of the $j^{th}$ acquisition from the short $T_2$ component can be expressed as follows:

$$M_{z,S}^j = M_0(1-E_1)(e_1 f_z)^{j-1} + M_0(1-e_1)\left[1-(e_1 f_z)^{f-1}\right]/(1-e_1 f_z). \quad (14)$$

Long $T_2$ Signal Suppression

It is difficult to completely suppress all the long $T_2$ tissues with different $T_1$s using a single IR pulse. However, when the TR is shorter, the nulling TIs for all the tissues get closer. Moreover, for long $T_2$ tissues with longer $T_1$ relaxation times, it is easier to achieve sufficient signal suppression with a broader range of TIs. More details can be found in the simulation section. When several spokes near the nulling point are acquired, the excited transverse magnetizations before the nulling point are of opposite polarity to those acquired after the nulling point. Then, long $T_2$ signal suppression can be achieved because these transverse magnetizations cancel each other out in the regridding process during image reconstruction.

The magnetizations of short $T_2$ tissues (such as trabecular bone) are not inverted, but instead largely saturated by the adiabatic IR pulse. They typically have a short $T_1$ and quickly recover to positive longitudinal magnetizations at TI. The signal intensities of short or long $T_2$ tissues are both proportional to the magnetization averaging of the multi-spoke acquisitions:

$$M_z = \sum\nolimits_{j=1}^{N_{sp}} M_z^j / N_{sp}. \quad [15]$$

A general framework to minimize signals from long $T_2$ tissues for the IR-prepared sequence is expressed as follows:

$$TI = \arg\min\left\{\sum_{i=1}^{N_{T_1}} \left[M_z(TI, TR, \alpha, \tau, N_{sp}, T_{1i})\right]\right\}, \quad [16]$$

where $N_T$ is the number of long $T_2$ tissues. $T_{1i}$ (i=1, 2, . . . , $N_{T_1}$) is the $T_1$ value of the $i^{th}$ long $T_2$ tissue. When TR, $\alpha$, $\tau$, and $N_{sp}$ are given, TI can be determined by Eq. [16] to achieve optimized long $T_2$ suppression. This framework can apply for suppressing either a single tissue component with an individual $T_1$ or a group of long $T_2$ tissues with a range of $T_1$s.

Methods

The 3D SIR-UTE sequence as shown in FIG. 1A can be implemented on a 3T clinical scanner (MR750, GE Healthcare Technologies, Milwaukee, WI). The Cones sequence sampled data along evenly spaced twisting paths in the shape of multiple cones. Data sampling started from the center of k-space as soon as possible after the RF excitation with a minimal nominal TE of 32 μs. The adiabatic IR pulse with a pulse shape of commonly used hyperbolic secant function, duration of 6.048 ms, bandwidth of 1.643 kHz, and maximum $B_1$ amplitude of 17 μT was used to invert or saturate tissues. The adiabatic IR pulse was centered on −220 Hz in the middle of the water and fat peak at 3T.

Simulation

Numerical simulation was performed to investigate the efficiency of the IR preparation scheme in the suppression of long $T_2$ signals with different TRs (i.e. 50, 100, 150, 200, 250, and 1000 ms). The simulated $T_1$ values of the long $T_2$ tissues ranged from 200 to 2000 ms. $\alpha$, $\tau$, and $N_{sp}$ were set to 20°, 4 ms, and 5, respectively, for all simulations. The excitation pulse duration d was 60 μs, which is much shorter than typical bone $T_2$* (i.e. around 300 μs). Thus, the longitudinal magnetization mapping function $f_z$ can be simplified to cos ($\alpha$).

Additionally, the contrast between trabecular bone and long $T_2$ tissues was also investigated for the SIR-UTE sequence with different TRs. The TI was determined by Eq. [16] in order to minimize the marrow fat signal since it is relatively difficult to suppress due to its relatively short $T_1$ and since it is a dominant component in trabecular bone. The $T_1$ values of marrow fat are assumed to be in the range of 320-350 ms, and the $T_1$ value of trabecular bone is set to 140 ms. The proton density of trabecular bone is assumed to be 12 percent of the long $T_2$ tissues.

Trabecular Bone Sample Study

Two hip bone samples (65-year-old female and 71-year-old male donors) were individually embedded in agarose gel (3 w/v %) to simulate human tissues. An 8-channel transmit/receive knee coil was used for both RF transmission and signal reception. Both clinical $T_1$-FSE and the proposed SIR-UTE sequences were used for the hip-agarose phantom experiment; the sequence parameters are listed as follows: 1) 2D $T_1$-FSE: TR/TE=550/8.1 ms, FOV=15×15 cm$^2$, slice thickness=5 mm, acquisition matrix=320×256, slice number=32, and scan time=59 s; 2) 3D SIR-UTE: TR/TI=82/37 ms, flip angle=20°; $N_{sp}$=3; $\tau$=7 ms; FOV=16×16×21 cm$^3$; matrix=160×160×42; and five separate scans with TEs=0.032/3.3, 0.2/4.4, 0.4, 0.8, and 1.1 ms to measure $T_2$*, each with scan time=4 min 20 sec.

In Vivo Trabecular Bone Study

In vivo spine imaging was performed on six healthy volunteers (24-38 years of age, 5 males and 1 female). Informed consent was obtained from all subjects in accordance with guidelines of the institutional review board. A rubber band with a $T_2$* around 0.3 ms was placed between the volunteer and the spine coil during scanning to serve as a reference to calibrate the proton density of trabecular bone. The proton density of trabecular bone can be calculated by the following equation:

$$\rho_{bone} = \rho_{ref}\frac{I_{bone}F_{ref}}{I_{ref}F_{bone}}, \quad [17]$$

$$\text{with } F = f_{xy}e^{\frac{TE}{T_2^*}}\left(1-e^{-TI/T_1}\right), \quad [18]$$

where $f_{xy}$ is the mapping function that describes the response of the transverse magnetization to a constant-amplitude RF pulse. It is a function of $T_2$ and pulse duration. $f_z$ is expressed in Eq. [13]. If the pulse duration and tissue $T_2$ are known, $f_{xy}$ and $f_z$ can be calculated directly. $I_{bone}$ and $I_{ref}$ are the signal intensities of trabecular bone and rubber band, respectively. To measure the proton density of the rubber band used in this study, an $H_2O$-$D_2O$ phantom was made with 20% $H_2O$ and 80% $D_2O$ by volume. It was doped with $MnCl_2$ to achieve a $T_2$* of 0.34 ms and a $T_1$ of 6.5 ms. The $T_2$* and $T_1$ of the rubber band are 0.38 ms and 200 ms, respectively. The $T_1$ relaxation was measured with our previously developed 3D UTE AFI-VTR method. The $H_2O$-$D_2O$ phantom and rubber band were put together and scanned with the proposed SIR-UTE sequence with TR/TI=150/64 ms. Together with the measured $T_1$ and $T_2$* values of the $H_2O$-$D_2O$ phantom and rubber band, the proton density of the used rubber band calculated by Eq. [17] was around 19 mol/L. In addition, $T_1$ values of the trabecular bone was set to 140 ms.

To correct the signal intensity bias due to the coil sensitivity inhomogeneity of the spine coil, the regular 3D UTE-Cones sequence was applied twice using spine and body coils, respectively, for signal reception. Then, with the assumption that the body coil has a homogeneous reception profile, the coil sensitivity map of the spine coil was calculated by dividing UTE-Cones images acquired with the spine coil by UTE-Cones images acquired with the body coil. The final spine trabecular bone images were generated by dividing the 3D SIR-UTE images by the obtained coil sensitivity map. The sequence parameters used for imaging of the spine were as follows: 1) $T_2$-FSE: TR/TE=4370/103 ms, FOV=34×34 $cm^2$, slice thickness=3.2 mm, matrix=360×270, slice number=14, and scan time=1 min 5 sec; 2) 3D SIR-UTE: TR/TI=150/64 ms, TE=0.032 ms, flip angle=18°, $N_{sp}$=5, i=3.8 ms, FOV=34×34×16 $cm^3$, matrix=160×160×32, oversampling factor=4 (the center of k-space was oversampled by a factor of 4 to reduce artifacts), and scan time=10 min; 3) 3D UTE-Cones: TR=6 ms, TE=0.032 ms, flip angle=2°, FOV=34×34×16 $cm^3$, matrix=160×160×32, oversampling factor=4, and scan time=1 min. $T_2$* measurement was used to evaluate the efficiency of long $T_2$ suppression in 3D SIR-UTE imaging of trabecular bone. A single-component short $T_2$* means a sufficient suppression of pore water and fat in trabecular bone is achieved, and that only bound water in trabecular bone is detected by the 3D SIR-UTE sequence. Four separate scans with TEs=0.032/2.2, 0.2, 0.4, and 0.8 ms were employed to measure $T_2$* in three of the volunteer experiments.

In vivo hip imaging was performed on six healthy volunteers (24-36 years of age, three males and three females). A routine cardiac coil was used for the hip scan. The sequence parameters used for hip imaging were as follows: 1) $T_2$-FSE: TR/TE=10000/92 ms, FOV=38×38 $cm^2$, slice thickness=3 mm, matrix=320×320, slice number=24, nex=2, scan time=3 min; 2) 3D SIR-UTE: TR/TI=150/64 ms, TE=0.1 ms, flip angle=18°, $N_{sp}$=5, i=4.1 ms, FOV=38×38×20 $cm^3$, matrix=160×160×40, oversampling factor=3.2, and scan time=9 min 32 sec.

Data Analysis

The trust-region-reflective algorithm was used to solve the non-linear minimization of Eq. [16]. A single exponential function was employed for $T_2$* fitting of the multiple-TE SIR-UTE data. The 3D UTE-Cones images acquired with both spine and body coils were smoothed using a 3D Gaussian kernel with standard deviation of 2 before the coil sensitivity calculation. All analysis algorithms were written in Matlab (The MathWorks Inc., Natick, MA, USA) and were executed offline on the DICOM images obtained by the acquisition protocols described above.

Results

Numerical simulations of the signal variations in the IR-UTE sequence (i.e. $|M_z|$) for a wide range of Tis (i.e., [200, 2000] ms) are shown in FIGS. 25A to 25F. The TI ranges from 0 to TR for each $T_1$. The best signal null point for each $T_1$ is located in the region 2502, 2504, 2506, 2508, 2510, 2512. The region 2502, 2504, 2506, 2508, 2510, 2512 becomes wider when $T_1$ is longer, demonstrating that the signal suppression for long $T_1$ tissues is less sensitive to the choice of TI. Thus, sufficient signal suppression of longer $T_1$ tissues can be achieved with a wider range of TIs. If there are several long $T_2$ tissues to be suppressed, it is a good choice to set the TI at the null point of the shortest $T_1$ tissue. Moreover, the null points get closer for all the Tis when the TR is shorter. Therefore, it is much easier to sufficiently suppress long $T_2$ tissues with a wide range of $T_1$s when a short TR is used in the single IR type sequences.

Figure 26:
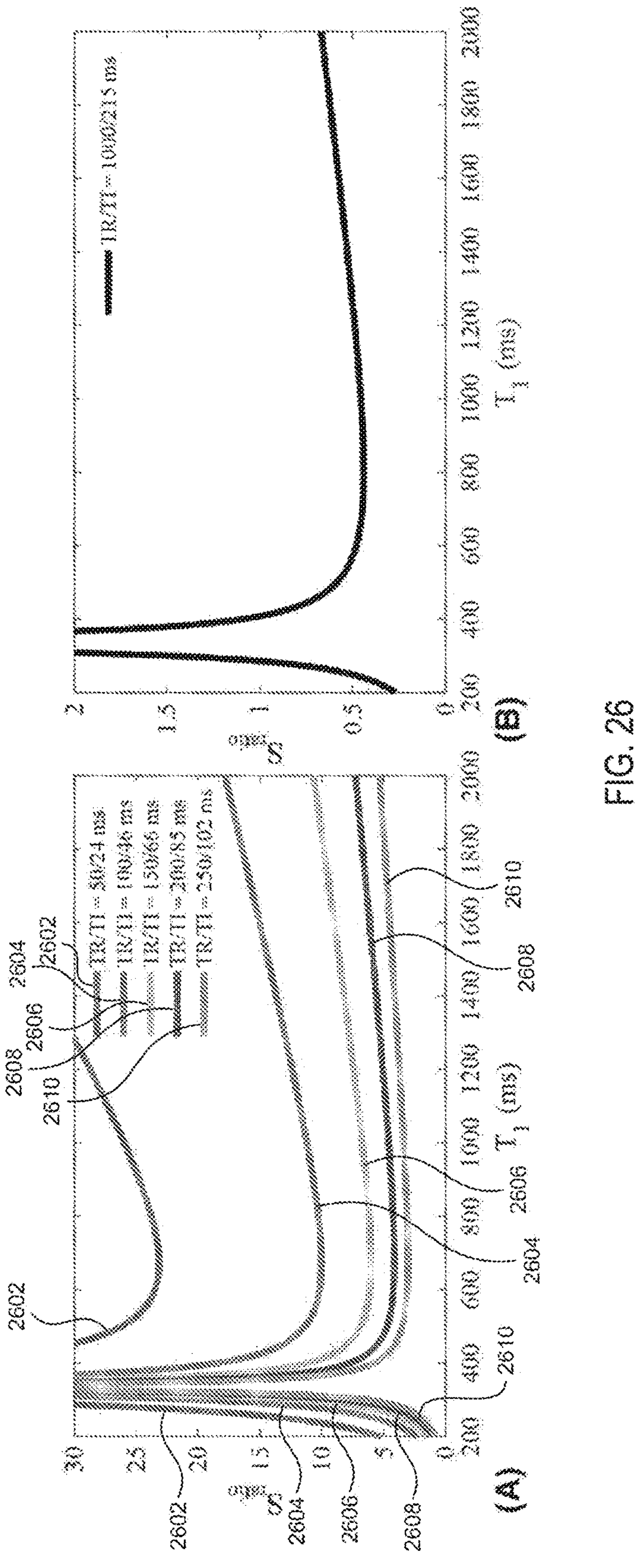
FIGS. 26A and 26B show the simulation results of the contrast between bone and long T2 tissues in IR-UTE imaging.

FIGS. 26A and 26B show the simulation results of the contrast between bone and long $T_2$ tissues in IR-UTE imaging. The Sratio is defined as the signal intensity ratio between trabecular bone and long T2 tissue. The T1s of long T2 tissues ranged from 200-2000 ms and the T1 of trabecular bone was assumed to be 140 ms. The Sratio curves with relatively short TRs of 50, 100, 150, 200, 250 ms are shown as 2602, 2604, 2606, 2608, 2610, respectively, in FIG. 26A and the curve with a much longer TR of 1000 ms is shown in FIG. 26B. The optimal TI for each TR was determined by minimizing Eq [16] to null marrow fat. Improved trabecular bone contrast is achieved when a shorter TR is used in the IR-UTE sequence Similar to the findings in FIGS. 26A and 26B, the contrast between bone and long $T_2$ tissues is higher when a shorter TR is used. Even with a TR of 250 ms, moderate bone contrast is still obtained. In the case of long TR (e.g., 1000 ms), only a small range of Tis could be well suppressed, suggesting that the signal suppression efficiency is very sensitive to the choice of TI.

Figure 27:
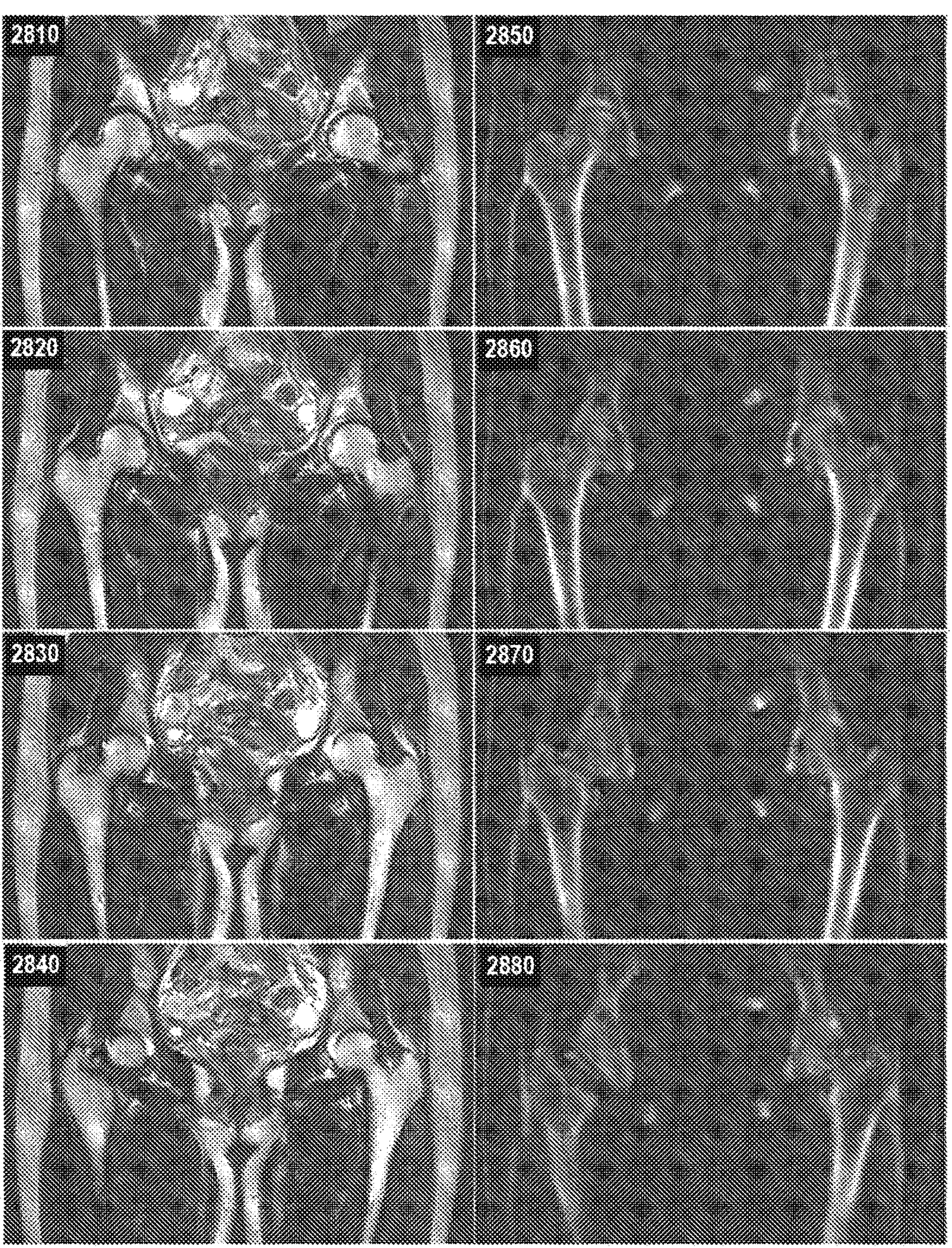
FIG. 27 shows in vivo images of a hip of a volunteer, which are obtained using imaging techniques suggested in this patent document.

FIG. 27 shows in vivo images of the hip of a 24-year-old female volunteer. In contrast to the conventional $T_2$-weighted FSE images, soft tissues are well-suppressed, but cortical bone is bright in the corresponding SIR-UTE images. Trabecular bone of the hip shows lower proton density compared with cortical bone. In vivo imaging of the hip of a 24-year-old female volunteer with a clinical 2D T2-weighted FSE (see images 2810, 2820, 2830 and 2840) and 3D IR-UTE-Cones (see images 2850, 2860, 2870 and 2880) sequences. The long T2 muscle and fat are bright in the clinical T2-FSE images. In comparison, the soft tissues are well-suppressed in the 3D IR-UTE-Cones images, demonstrating a high contrast for cortical and trabecular bone in the hip.

Figure 28:
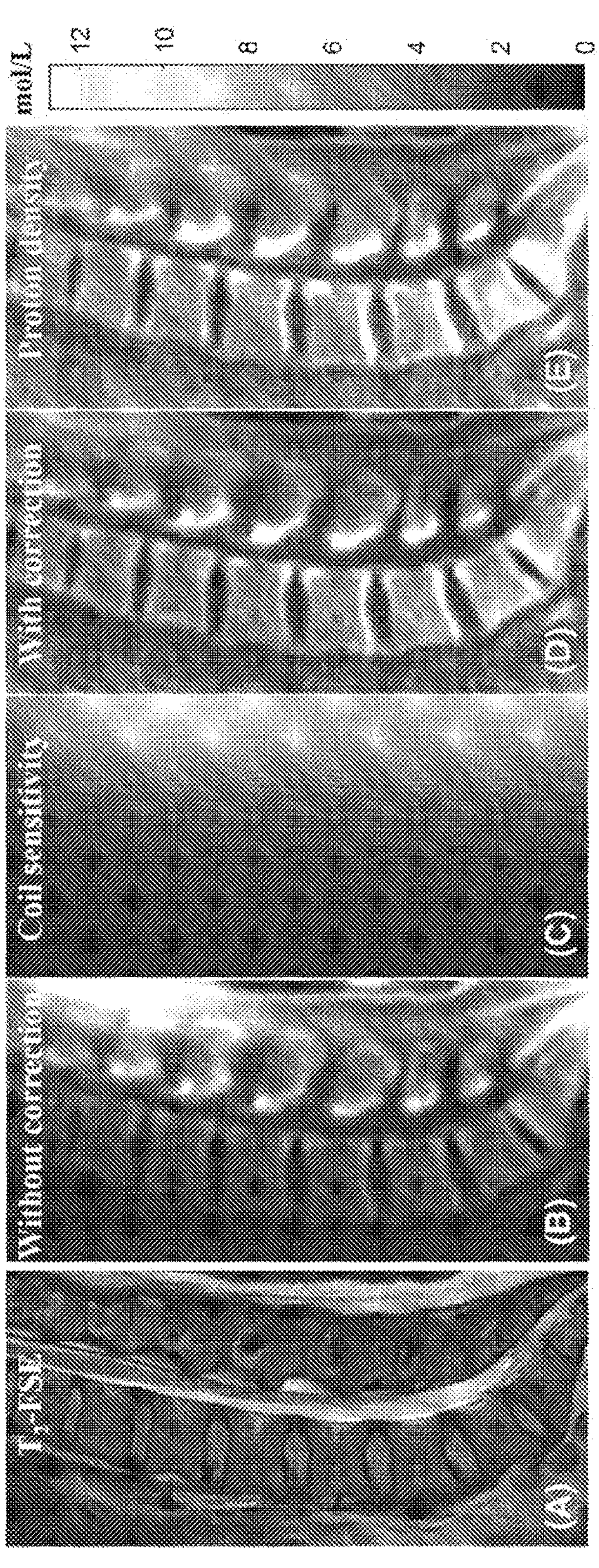
FIGS. 28A to 28E show the bound water proton density map of vertebrae of a volunteer that is obtained using imaging techniques suggested in this patent document.

FIGS. 28A to 28E show the bound water proton density map of vertebrae in a 31-year-old male volunteer. In vivo qualitative and quantitative imaging of the spine of a 31-year-old male volunteer using the 3D IR-UTE-Cones sequence. The long T2 muscle and fat are bright in the clinical T2-FSE image shown in FIG. 28A, the original 3D IR-UTE-Cones image shown in FIG. 28B shows non-uniform signal intensity distribution because of the inhomogeneous coil sensitivity of the spine coil (see FIG. 28C). After the coil sensitivity correction, the spine bone image demonstrates a more uniform signal intensity distribution (see FIG. 28D). The proton density map of the spine trabecular bone as shown in FIG. 28E is calculated based on the coil sensitivity corrected 3D IR-UTE-Cones image as shown in FIG. 28D. Since the coil sensitivity of the spine coil is quite inhomogeneous, signal intensity correction is critical for accurate quantitative proton density mapping. It can be found that images of the vertebrae are much more uniform after coil sensitivity correction. Proton densities of the vertebrae calculated by Eq. [18] range from 5 to 9 mol/L.

It is demonstrated that the 3D SIR-UTE sequence with a short TR/TI combination can suppress signals from long $T_2$ water and fat simultaneously and can provide high image contrast for short $T_2$ trabecular bone. It is suggested that the TI needs to be selected close to the null point of short $T_1$ tissues since the long $T_1$ tissue suppression is less sensitive to the selection of TI. It is observed that the shorter the TR of the IR-UTE sequence, the better to suppress long $T_2$ tissues with a wide range of $T_1$s since their signal null points were getting closer. Our ex vivo and in vivo studies demonstrated the robustness of the 3D SIR-UTE sequence in suppressing long $T_2$ water and fat signals in the spine and hip. Furthermore, the 3D SIR-UTE sequence allowed quantitative proton density mapping and $T_2$* measurement of the short $T_2$ water component in trabecular bone.

UTE techniques can provide direct imaging of short $T_2$ bone, which is invisible with conventional sequences. The majority of bone studies using qualitative and quantitative UTE imaging are focused on cortical bone. However, evaluation of trabecular bone may be even more valuable since most osteoporotic fractures occur at locations that are rich in trabecular bone. WASPI and UTE with SPIR preparation have been proposed for trabecular bone imaging. However, these two techniques are sensitive to $B_1$ and $B_0$ inhomogeneities, making them perhaps unsuitable for in vivo spine and hip imaging. In comparison, an adiabatic IR pulse with a relatively broad spectral coverage of 1.643 kHz is used in the proposed 3D SIR-UTE sequence, and the long $T_2$ suppression is less sensitive to $B_1$ and $B_0$ inhomogeneities. Together with a short TR and a short TI, the proposed SIR-UTE sequence is more robust in suppressing both water and fat. In some simulations, a TR of 150 ms was used in 3D SIR-UTE imaging of the spine and hip in vivo to balance the effectiveness of long $T_2$ suppression and specific absorption rate (SAR) limitation. Compared with DEXA, which is a 2D projection imaging technique that cannot distinguish between cortical and trabecular bone, the proposed 3D SIR-UTE MR imaging technique can provide volumetric information of cortical and trabecular bone separately. Since the bound water proton density in cortical bone is typically much higher than that in trabecular bone (36,37), a threshold-based method can potentially be used to separate cortical and trabecular bone in 3D SIR-UTE images. Therefore, the proposed 3D SIR-UTE MR imaging technique may have significant advantages over the current gold standard, DEXA, which is a 2D projection imaging technique that cannot distinguish between cortical and trabecular bone.

The $T_2$* values measured in both ex vivo and in vivo studies were in the range of 0.3-0.45 ms, which are similar to the $T_2$*s of bound water in cortical bone. Thus, the proton density measured by the proposed 3D SIR-UTE technique is likely collagen-bound water proton density with effective suppression of pore water components. The collagen bone matrix provides tensile strength and elasticity in bone. Thus, it would be useful to obtain information from the collagen bone matrix to evaluate bone quality. MR imaging of collagen matrix-bound water has been studied by several groups in recent years as a possible surrogate measure of collagen bone matrix (36,40,41). For example, the bound water proton density is highly correlated with collagen matrix density, with $R^2$=0.74, as reported in a previous study of cortical bone samples. A lower bound water proton density may indicate a more degenerative collagen matrix with less tensile strength/elasticity in bone. We expect that the measured volumetric proton density in this study can be used as a potential biomarker to evaluate the bone quality in early osteoporosis and osteoporotic fracture risk.

Long $T_2$ signal contamination is typically a major source of error in quantitative UTE imaging. Since the SIR-UTE sequence allows for selective imaging of short $T_2$ tissues, it can also be used for quantitative evaluation of proton density and $T_2$*, as well as for $T_1$ relaxation times. In some simulations, the SIR-UTE acquisition together with a reference rubber phantom provided volumetric mapping of proton density for the trabecular bone, which may be a useful biomarker to evaluate the bone quality. A relatively high data oversampling factor was used in both in vivo spine and hip imaging with the SIR-UTE sequence, which can increase the image signal to noise ratio (SNR) and simultaneously reduce the motion (as a result of motion averaging) and aliasing artifacts. Respiratory gating is also an effective strategy to reduce motion artifacts due to breathing. Since the marrow fat has a relatively short $T_2$* between 5 and 15 ms, the inversion efficiency Q may not reach −1. To account for this imperfect inversion and to achieve a sufficient nulling of marrow fat, a smaller TI with 1-2 ms less than the TI calculated by the Eq. [16] was used in our study. The proposed 3D SIR-UTE sequence can also be used for cortical bone imaging both morphologically and quantitatively (e.g., $T_2$* and proton density).

Both the rubber band and the manganese-doped water (which has an extremely short $T_2$) can serve as the reference to calibrate the trabecular bone proton density. The rubber band has closer $T_1$ and $T_2$* relaxations to the bound bone water than the manganese-doped water (which has a $T_1$ that is much shorter than that of bound bone water). Thus, the rubber band has a contrast more similar to the bound bone water. Using the rubber band as the reference may be more resistant to the error in bound bone water quantification than using the manganese-doped water within a wide range of sequence parameters. On the other hand, there is a problem with the rubber band (a polybutadiene type elastomer), which may have more than one resonance (due to chemical shift), leading to errors in bound bone water quantification. The robustness and accuracy of bound bone water quantification using the two references in our future investigations can be compared.

Figure 25:
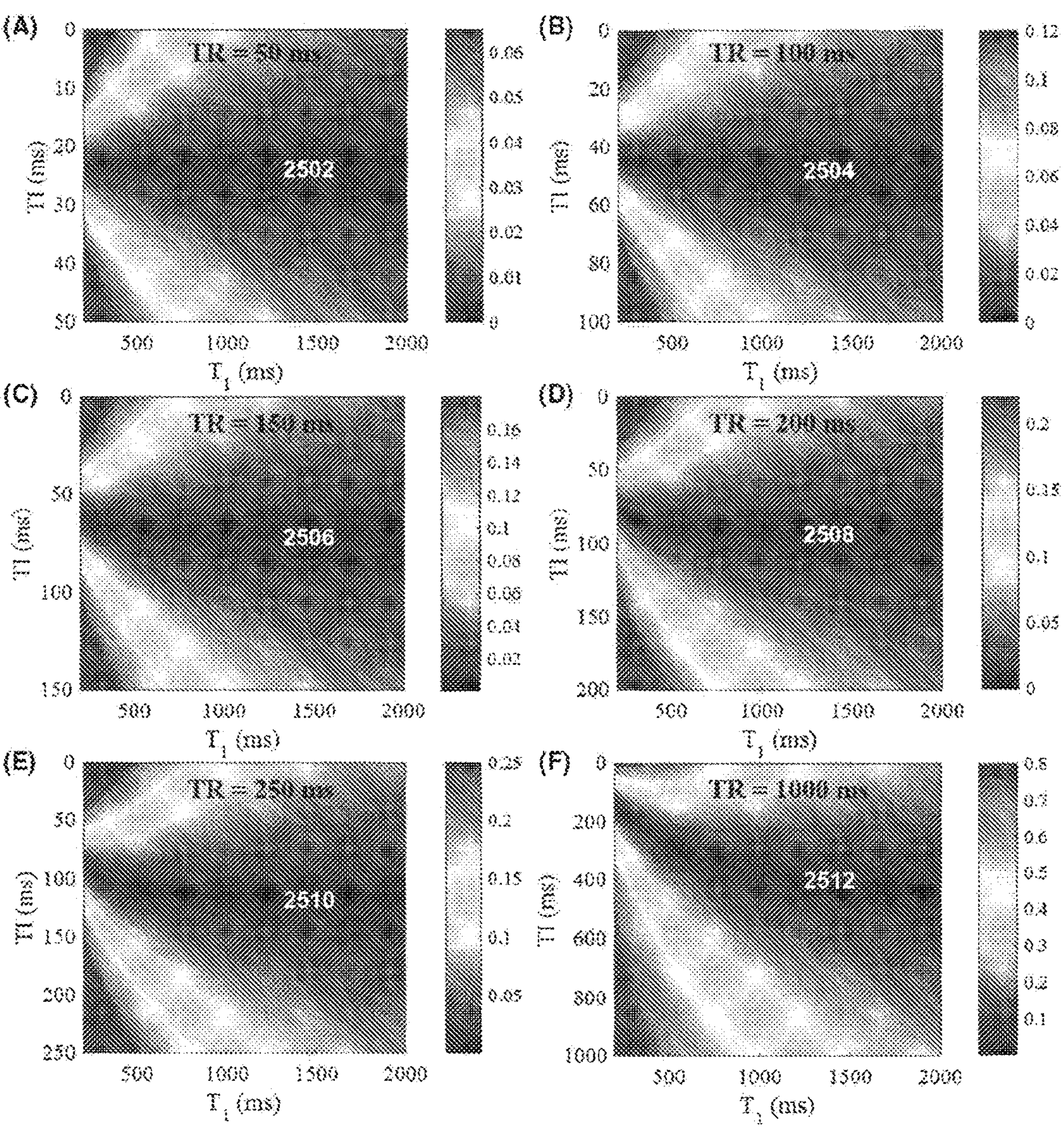
FIGS. 25A to 25F show numerical simulations of signal variations in an IR-UTE sequence for a wide range of Tis.

The SIR-UTE sequence with a short TR/TI combination can be readily used for imaging of other short $T_2$ species, such as for direct imaging of myelin protons in the white matter of the brain. There are several groups of water protons, such as those in cerebrospinal fluid, extra- and intra-cellular water, and water trapped in the myelin bilayers, which may have different $T_1$s; therefore, efficient suppression of all kinds of water protons is essential for selective imaging of myelin protons. The 3D SIR-UTE sequence with a short TR/TI combination can largely suppress various water groups with different $T_1$s as shown in FIG. 25 and may thusly be used for more robust imaging of myelin where water components with various Tis may exist in white matter of the brain.

Figure 29:
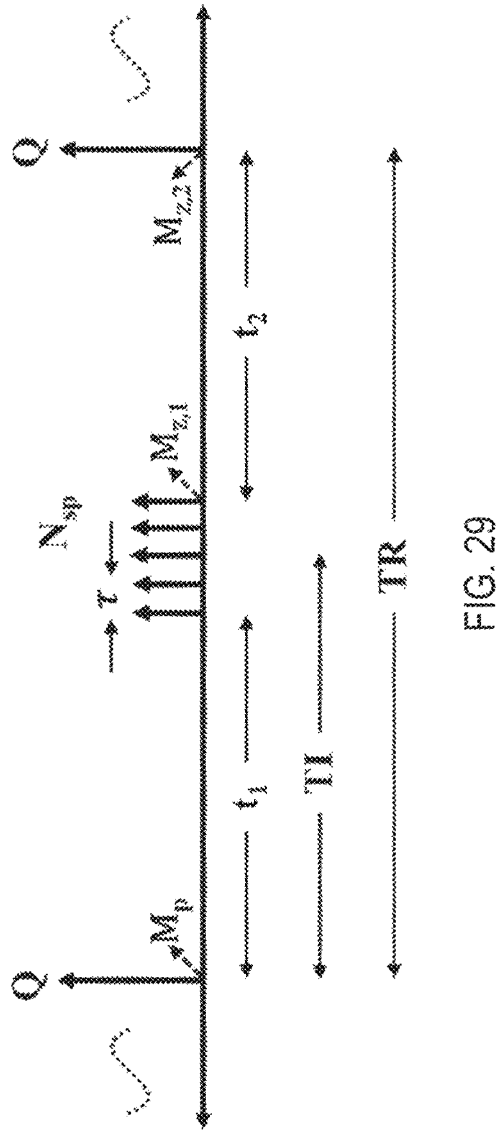
FIG. 29 shows steady state magnetization and timing for the 3D SIR-UTE sequence.

FIG. 29 shows steady state magnetization and timing for the 3D SIR-UTE sequence. The short and long arrows represent the excitation and inversion pulses respectively. Q is the inversion efficiency of the used inversion pulse. $t_1$ is the duration from the center of the IR pulse to the first excitation pulse. $t_2$ is the duration from the last excitation pulse to the center of the IR pulse. $M_p$, $M_{z,1}$, and $M_{z,2}$ are the longitudinal magnetizations after the IR pulse, after the last excitation pulse and before the IR pulse, respectively. The relations of above three magnetizations according to Bloch equations, which are expressed as follows:

$$M_{z,1} = (M_p A_{N_{sp}} + B_{N_{sp}}) f_z, \quad [19]$$

$$M_{z,2} = M_{z,1}\exp(-t_2/T_1) + M_0[1 - \exp(-t_2/T_1)], \quad [20]$$

$$M_p = QM_{z,2}, \quad [21]$$

where $t_1$=TI−0.51τ($N_{sp}$−1) and $t_2$=TR−TI−0.5τ($N_{sp}$−1). $A_{N_{sp}}$ and $B_{N_{sp}}$ can be found in the Theory section. $M_p$ is determined from Eq. [19] to [21] and its final expression is shown in Eq. [12].

Figure 30:
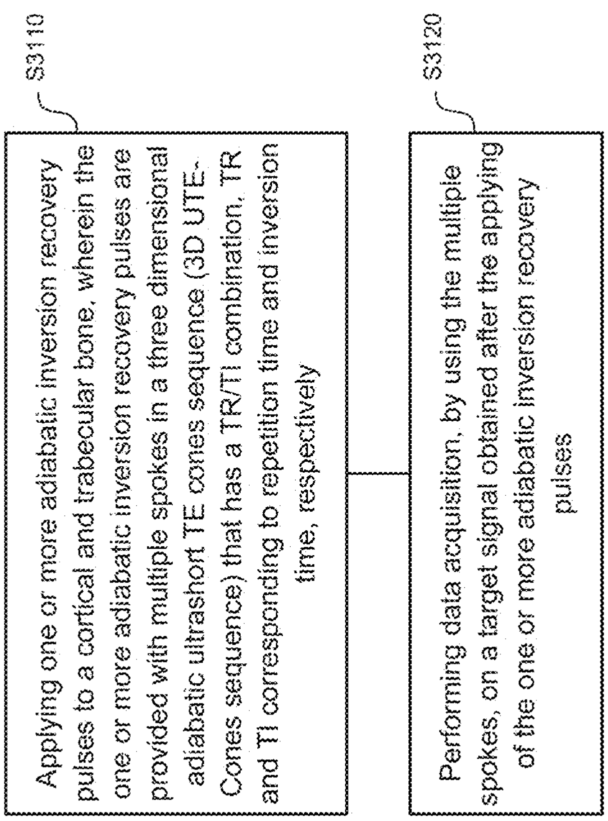
FIGS. 30 and 31 show example methods for imaging cortical and trabecular bone based on some implementations of the disclosed technology.

FIG. 30 shows an example flowchart of a method for imaging cortical and trabecular bone. The method includes, at operation 3110, applying one or more adiabatic inversion recovery pulses to the cortical and trabecular bone, wherein the one or more adiabatic inversion recovery pulses are provided with multiple spokes in a three dimensional adiabatic ultrashort TE cones sequence (3D UTE-Cones sequence) that has a TR/TI combination, TR and TI corresponding to repetition time and inversion time, respectively. The method further includes, at operation 3120, performing data acquisition, by using the multiple spokes, on a target signal obtained after the applying of the one or more adiabatic inversion recovery pulses.

Figure 31:
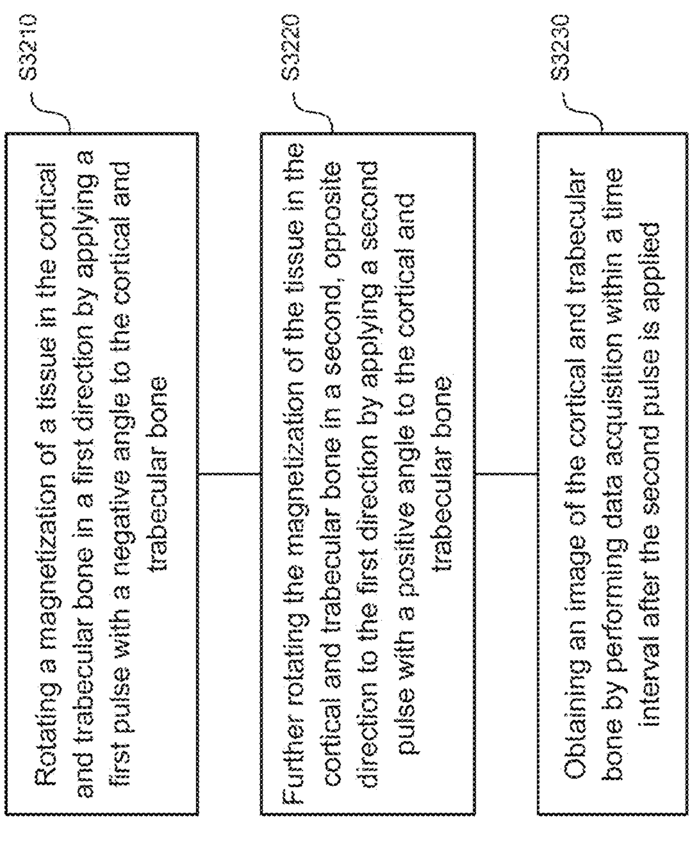

FIG. 31 shows another example flowchart of a method for imaging cortical and trabecular bone. The method includes, at operation 3210, rotating a magnetization of a tissue in the cortical and trabecular bone in a first direction by applying a first pulse with a negative angle to the cortical and trabecular bone. The method further includes, at operation 3220, further rotating the magnetization of the tissue in the cortical and trabecular bone in a second, opposite direction to the first direction by applying a second pulse with a positive angle to the cortical and trabecular bone. The method further includes, at operation 3230, obtaining an image of the cortical and trabecular bone by performing data acquisition within a time interval after the second pulse is applied.

Figure 32:
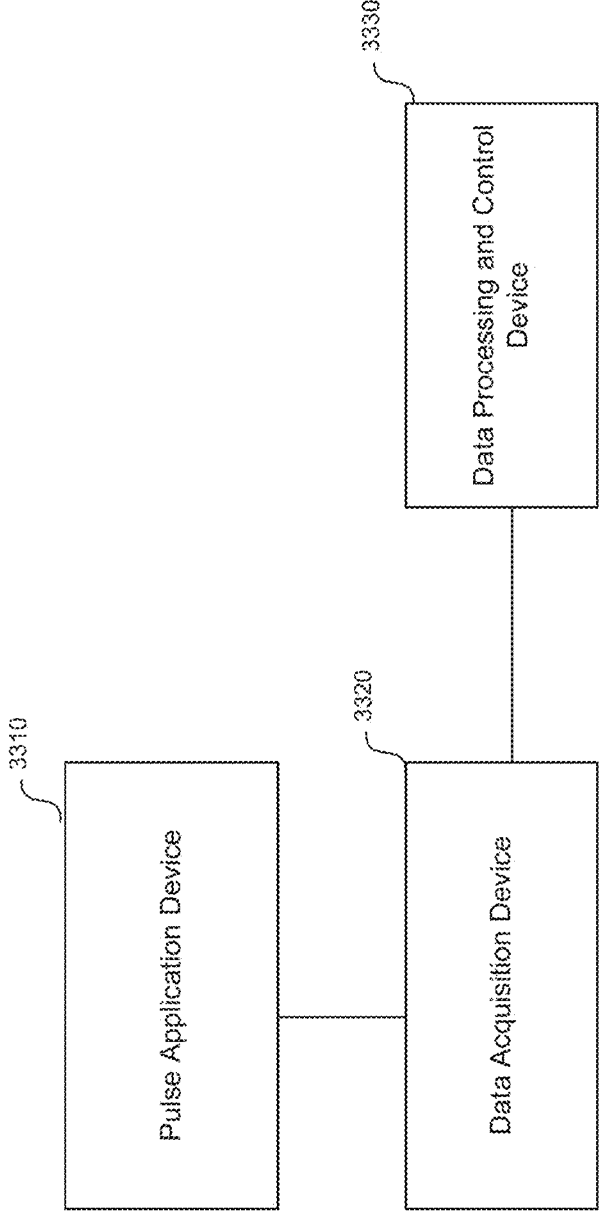
FIG. 32 shows an example system for imaging cortical and trabecular bone based on some implementations of the disclosed technology.

Some implementations of the disclosed technology can provide a system for imaging cortical and trabecular bone. FIG. 32 shows an example system for imaging cortical and trabecular bone. The system may include a pulse application device 3310 structured to apply, to the cortical and trabecular bone, one or more adiabatic inversion recovery pulses. The pulse application device 3310 may be, for example, a radio frequency (RF) coil that is coupled to a pulse generation circuit that generates a pulse using electromagnetic circuitry that is driven by a processor that controls the circuitry to generate a desired waveform which is amplified and applied to the RF coil.

The system may further include a data acquisition device 3320 interfaced with the pulse application device 3310 and operable to obtain image data associated with the cortical and trabecular bone and perform data acquisition on the obtained image data. The data acquisition device 3320 is configured to interwork with the pulse application device 3310 to provide at least one of a 3D SIR-UTE sequence, 3D DIR-UTE sequence, or a soft-hard composite pulse, which are discussed in this patent document. The data acquisition device 3320 may further include a processor and a memory that stores data and information that can be used to cause the processor to implement a method for imaging a cortical and trabecular bone imaging and signal characterization method as shown in FIGS. 30 and 31. The memory of the data acquisition device 3320 may store processing parameters, processed parameters, and other data that can be used in the implementation of the imaging of cortical and trabecular bone.

The system may further include a data processing and control device 3330 in communication with the data acquisition device 3320, the data processing and control device including a processor configured to process the image data obtained by the data acquisition device to provide, based on the processed image data, mapping information of one or more properties associated with the cortical and trabecular bone. The data processing and control device 3330 can further include memory that stores processor-executable code, which when executed by the processor, configures the data processing and control device 3303 to perform various operations, e.g., such as receiving information, commands, and/or data, processing information and data, and transmitting or providing information/data to another device. The memory of the data processing and control device 3300 can store other information and data, such as instructions, software, values, images, and other data processed or referenced by processor of the data processing and control device 3300. For example, various types of Random Access Memory (RAM) devices, Read Only Memory (ROM) devices, Flash Memory devices, and other suitable storage media can be used to implement storage functions of memory unit 122. The memory of the data processing and control device 3300 can store imaging data and information, which can include spatial and spectral data, hardware parameters, data processing parameters, and processed parameters and data that can be used in the implementation of data processing and controlling techniques in accordance with the disclosed technology.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms “a”, “an” and “the” are intended to include the plural forms as well, unless the context clearly indicates otherwise. Additionally, the use of “or” is intended to include “and/or”, unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

The invention claimed is:

1. A method for imaging a cortical and trabecular bone, comprising:

applying to the cortical and trabecular bone one or more adiabatic inversion recovery pulses configured to suppress unwanted signals from a tissue surrounding the cortical and trabecular bone and from pore water in the cortical and trabecular bone having a range of T1 relaxation times, wherein the one or more adiabatic inversion recovery pulses are provided with multiple spokes in a three dimensional adiabatic ultrashort TE cones sequence (3D UTE-Cones sequence) that has a TR/TI combination, TR and TI corresponding to a repetition time and an inversion time, respectively;

applying a soft-hard composite pulse to the cortical and trabecular bone, wherein the soft-hard composite pulse comprises:

a soft pulse with a negative flip angle, wherein the soft pulse is configured to further suppress the unwanted signals from the tissue, and a hard pulse, applied after the soft pulse, with a positive flip angle that has a same absolute value as the negative flip angle;

performing data acquisition, by using the multiple spokes, on a target signal obtained after the applying of the one or more adiabatic inversion recovery pulses and the applying of the soft-hard composite pulse; and obtaining mapping information on at least one of total water, bound water, pore water, or collagen proton based on image data associated with the cortical and trabecular bone, wherein the image data is obtained using the 3D UTE-Cones sequence.

2. The method of claim 1, wherein the tissue has a relatively longer transverse relaxation time than that of the cortical and trabecular bone.

3. The method of claim 2, wherein the TR/TI combination is pre-selected to suppress the unwanted signal from the tissue in the cortical and trabecular bone.

4. The method of claim 1, wherein the one or more adiabatic inversion recovery pulses include at least one of a single adiabatic inversion recovery pulse or a double adiabatic inversion recovery pulse.

5. The method of claim 2, wherein the tissue corresponds to at least one of a marrow fat or a muscle.

6. The method of claim 2, wherein the one or more adiabatic inversion recovery pulses are applied after the applying of the soft-hard composite pulse.

7. The method of claim 6, wherein the soft pulse is centered on a fat on-resonance frequency.

8. The method of claim 1, further comprising, before the performing the data acquisition:

exciting the target signal by applying a short rectangular pulse having a duration less than 100 μs.

9. The method of claim 1, wherein the multiple spokes are obtained after each of the one or more adiabatic inversion recovery pulses.

10. A system for imaging a cortical and trabecular bone, comprising:

a pulse application device structured to apply, to the cortical and trabecular bone, one or more adiabatic inversion recovery pulses configured to suppress unwanted signals from a tissue surrounding the cortical and trabecular bone and from pore water in the cortical and trabecular bone having a range of T1 relaxation times;

a data acquisition device interfaced with the pulse application device and operable to obtain image data associated with the cortical and trabecular bone and perform data acquisition on the obtained image data, wherein the data acquisition device with the pulse application device is configured to apply a soft-hard composite pulse to the cortical and trabecular bone, wherein the soft-hard composite pulse comprises:

a soft pulse with a negative flip angle, wherein the soft pulse is configured to further suppress the unwanted signals from the tissue, and a hard pulse, applied after the soft pulse, with a positive flip angle that has a same absolute value as the negative flip angle; and a data processing and control device in communication with the data acquisition device, the data processing and control device including a processor configured to process the image data obtained by the data acquisition device to provide, based on the processed image data, mapping information on at least one of total water, bound water, pore water, or collagen proton associated with the cortical and trabecular bone, wherein the data acquisition device is configured to perform data acquisition using multiple spokes, wherein the one or more adiabatic inversion recovery pulses and the multiple spokes are provided during a three dimensional adiabatic ultrashort TE cones sequence (3D UTE-Cones sequence) that has a TR/TI combination to sufficiently suppress an unwanted signal from a tissue in the cortical and trabecular bone, TR and TI corresponding to repetition time and inversion time, respectively, wherein the image data is obtained using the 3D UTE-cones sequence.

11. The system of claim 10, wherein the one or more adiabatic inversion recovery pulses include at least one of a single adiabatic inversion recovery pulse or a double adiabatic inversion recovery pulse.

12. The system of claim 10, the soft pulse is centered on a fat on-resonance frequency.

13. The system of claim 10, wherein a channel of the pulse application device is configured to apply the one or more adiabatic inversion recovery pulses toward the cortical and trabecular bone in a hip or a spine.

14. The system of claim 10, wherein the tissue has a relatively longer transverse relaxation time than that of the cortical and trabecular bone.

* * * * *